US011667899B2

(12) United States Patent
Pyle et al.

(10) Patent No.: US 11,667,899 B2
(45) Date of Patent: Jun. 6, 2023

(54) REVERSE TRANSCRIPTASE AND METHODS OF USE

(71) Applicant: YALE UNIVERSITY, New Haven, CT (US)

(72) Inventors: Anna Marie Pyle, Guilford, CT (US); Chen Zhao, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 121 days.

(21) Appl. No.: 16/626,008

(22) PCT Filed: Jun. 27, 2018

(86) PCT No.: PCT/US2018/039738
§ 371 (c)(1),
(2) Date: Dec. 23, 2019

(87) PCT Pub. No.: WO2019/005955
PCT Pub. Date: Jan. 3, 2019

(65) Prior Publication Data
US 2021/0155910 A1 May 27, 2021

Related U.S. Application Data

(60) Provisional application No. 62/525,337, filed on Jun. 27, 2017.

(51) Int. Cl.
C12N 9/12 (2006.01)
C12P 19/34 (2006.01)

(52) U.S. Cl.
CPC ............ C12N 9/1276 (2013.01); C12P 19/34 (2013.01); C12Y 207/07049 (2013.01)

(58) Field of Classification Search
CPC C12N 9/1276; C12P 19/34; C12Y 207/07049
See application file for complete search history.

(56) References Cited

U.S. PATENT DOCUMENTS 9,506,045 B2 11/2016 Suko
9,637,726 B2 5/2017 Bauer

OTHER PUBLICATIONS

Earl ("The Genome Sequence of Lachnosiracaea bacterium 1_4_56AA", The Broad Institute, Sumitted to EMBL/GenBank/DDBJ, 2011, sequence alignment provided, results in SCORE) (Year: 2011).*
Zhao, C., & Pyle, A. M. (2016). Crystal structures of a group II intron maturase reveal a missing link in spliceosome evolution. Nature structural & molecular biology, 23(6), 558-565 (Year: 2016).*
Hoffman, A. D., Banapour, B., & Levy, J. A. (1985). Characterization of the AIDS-associated retrovirus reverse transcriptase and optimal conditions for its detection in virions. Virology, 147(2), 326-335 (Year: 1985).*

"SubName: Full=Retron-type reverse transcriptase {ECO:0000313|EMBL:CBK92290.1}", UniProtKB, (20100518), Database accession No. D4JMT6, URL: UniProt, XP055556552.
Agrawal RK et al., "Forks in the tracks: Group II introns, spliceosomes, telomeres and beyond," RNA Biol, Dec. 2016, 13 (12):1218-1222.
Baranauskas A et al., "Generation and characterization of new highly thermostable and processive M-MuLV reverse transcriptase variants," Protein Eng Des Sel, Oct. 2012;25(10):657-68.
Blocker FJ et al., "Domain structure and three-dimensional model of a group II intron-encoded reverse transcriptase," RNA, Jan. 2005;11(1):14-28.
Candales et al., "Database for bacterial group II introns," Nucleic Acids Res, Jan. 2012;40(Database issue):D187-90.
Dai et al., "A three-dimensional model of a group II intron RNA and its interaction with the intron-encoded reverse transcriptase," Mol Cell, May 23, 2008;30(4):472-85.
Enyeart PJ, et al. "Biotechnological applications of mobile group II introns and their reverse transcriptases: gene targeting, RNA-seq, and non-coding RNA analysis," Mob DNA. Jan. 13, 2014;5(1):2.
Gu et al., "Genetic identification of potential RNA-binding regions in a group II intron-encoded reverse transcriptase", RNA, (Feb. 23, 2010), vol. 16, No. 4, pp. 732-747, XP055556554 [A] 18-21, 23/(18-21), 34-37 *. Especially Abstract *.
Jamburuthugoda et al., "Identification of RNA binding motifs in the R2 retrotransposon-encoded reverse transcriptase," Nucleic Acids Res, Jul. 2014;42(13):8405-15.
Kew Y et al., "Insertions into the beta3-beta4 hairpin loop of HIV-1 reverse transcriptase reveal a role for fingers subdomain in processive polymerization," J Biol Chem, Mar. 27, 1998;273(13):7529-37.
Matsuura et al., "A bacterial group II intron encoding reverse transcriptase, maturase, and DNA endonuclease activities: biochemical demonstration of maturase activity and insertion of new genetic information within the intron", Genes and Development, (19971101), vol. 11, No. 21, pp. 2910-2924, XP055556553.
Matsuura et al., "Mechanism of maturase-promoted group II intron splicing," Embo J, Dec. 17, 2001;20(24):7259-70.
Mohr S et al., "Thermostable group II intron reverse transcriptase fusion proteins and their use in cDNA synthesis and next-generation RNA sequencing," RNA, Jul. 2013;19(7):958-70.
Nilsen TW et al., "Expansion of the eukaryotic proteome by alternative splicing," Nature, Jan. 28, 2010;463 (7280):457-63.
Qu G et al., "Structure of a group II intron in complex with its reverse transcriptase," 2016, Nat Struct Mol Biol, Jun. 2016;23(6):549-57.
Siegfried NA et al., "RNA motif discovery by SHAPE and mutational profiling (SHAPE-MaP)," Nat Methods,. Sep. 2014;11(9):959-65.
Nank H et al., "A reverse transcriptase/maturase promotes splicing by binding at its own coding segment in a group II ntron RNA," Mol Cell, Aug. 1999;4(2):239-50.
Xiao et al., "Improvement of the thermostability and activity of a pectate lyase by single amino acid substitutions, using a strategy based on melting-temperature-guided sequence alignment," Appl Environ Microbiol, Feb. 2008;74(4):1183-9.

(Continued)

Primary Examiner — Louise W Humphrey
Assistant Examiner — Trevor L Kane
(74) Attorney, Agent, or Firm — Riverside Law LLP

(57) ABSTRACT

The present invention provides compositions, methods, and kits related to reverse transcriptases derived from E.r. maturase.

17 Claims, 17 Drawing Sheets
Specification includes a Sequence Listing.

(56) References Cited

OTHER PUBLICATIONS

Zhao et al., "An ultraprocessive, accurate reverse transcriptase encoded by a metazoan group II intron", RNA, (Nov. 6, 2017), vol. 24, No. 2, pp. 183-195, XP055556555 [AP] 3, 4, 18-21, 23/(3, 4,18-21), 34-37 * . Entire documenl *.

Zimmerly S et al., "Group II intron mobility occurs by target DNA-primed reverse transcription," Cell, Aug. 25, 1995;82 (4):545-54.

Zubradt M et al., "DMS-MaPseq for genome-wide or targeted RNA structure probing in vivo," Nat Methods, Jan. 2017;14(1):75-82.

* cited by examiner

Fig. 1A
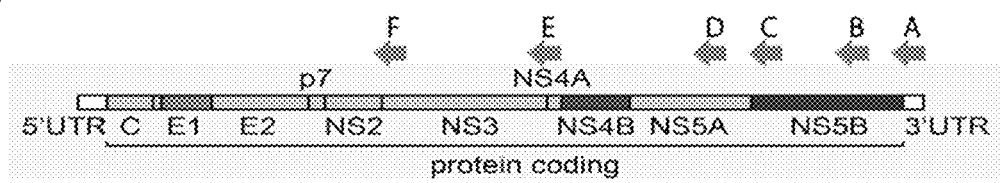
Fig. 1B
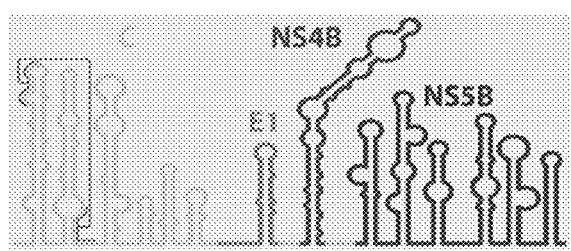
Fig. 1C
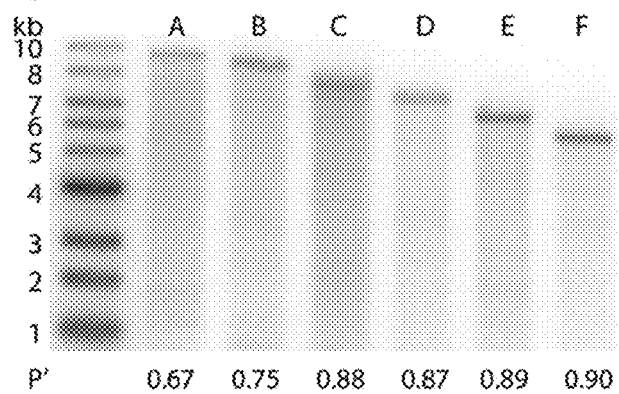
Fig. 1A – 1C

Fig. 2A
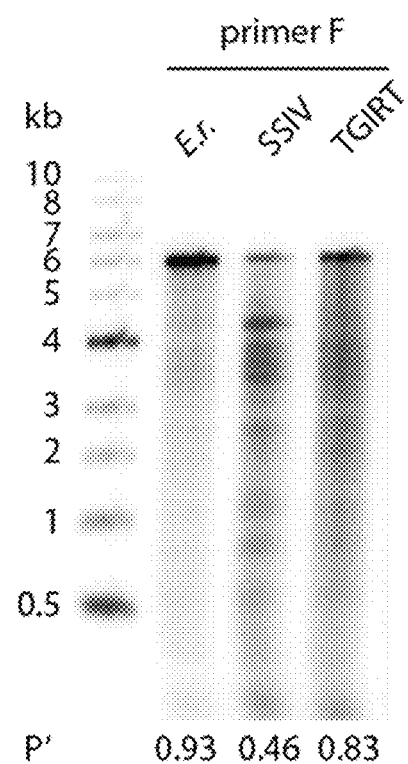
Fig. 2B
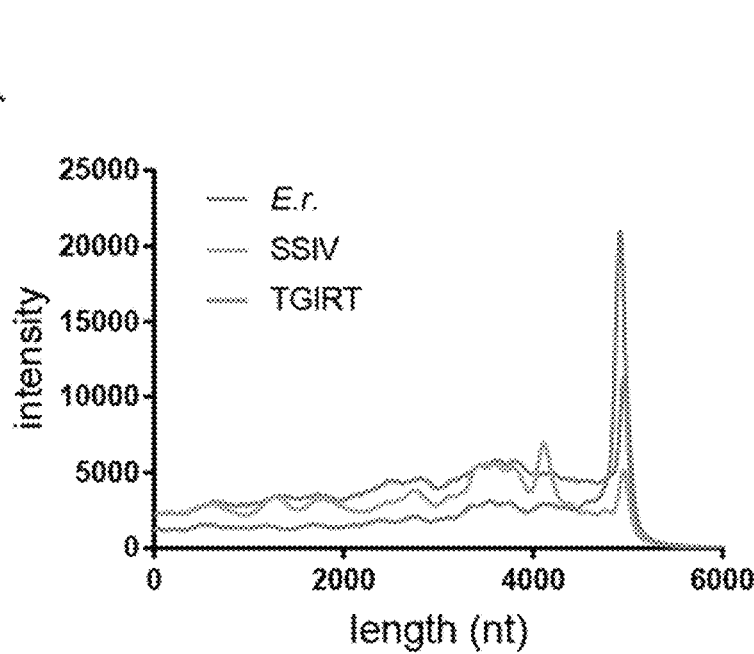
Fig. 2A- 2B

Fig. 3A
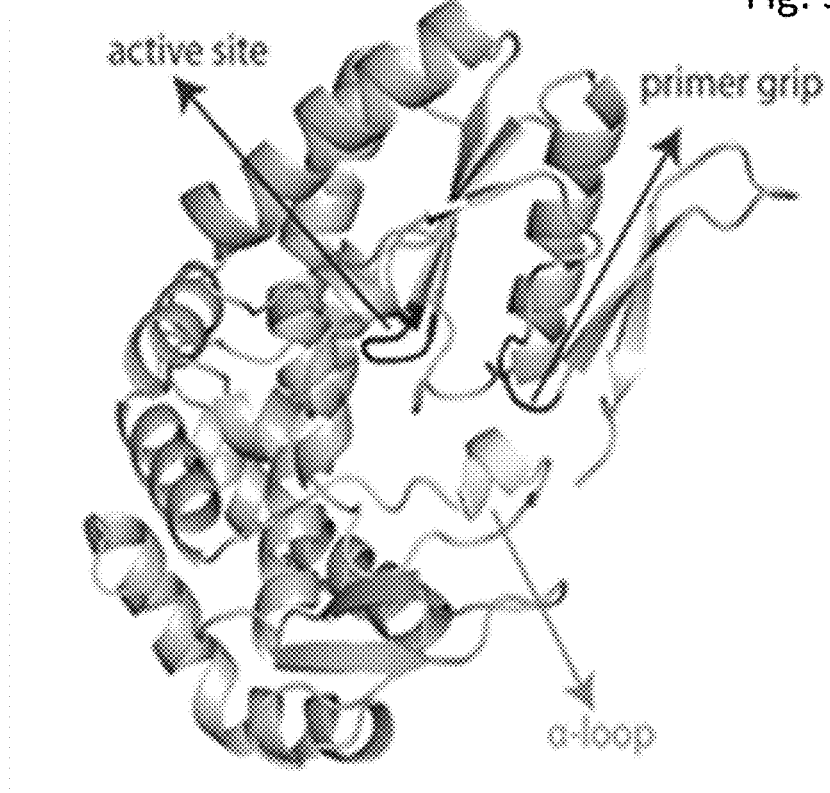
Fig. 3B
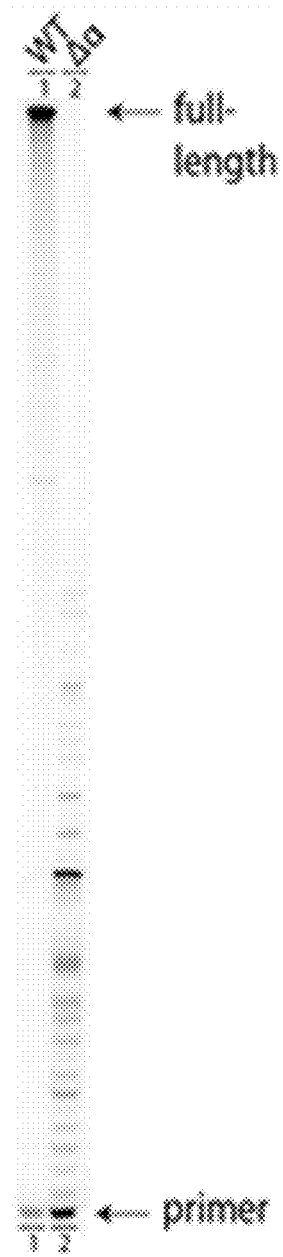
Fig. 3A- 3B

Fig. 4A
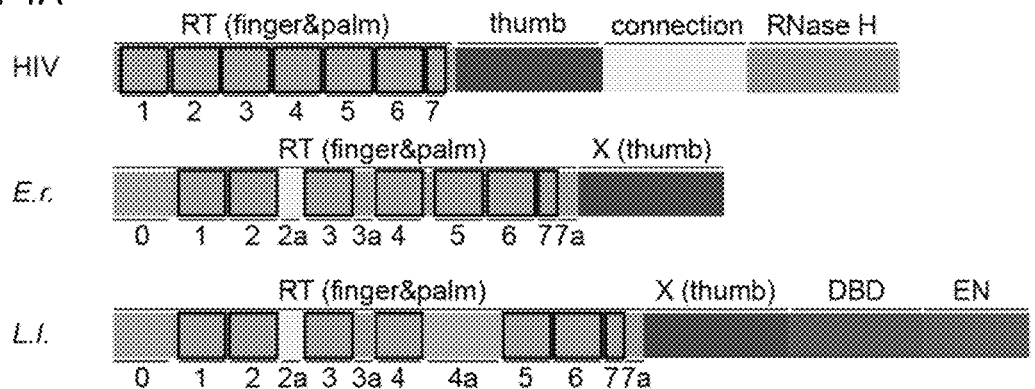
Fig. 4B
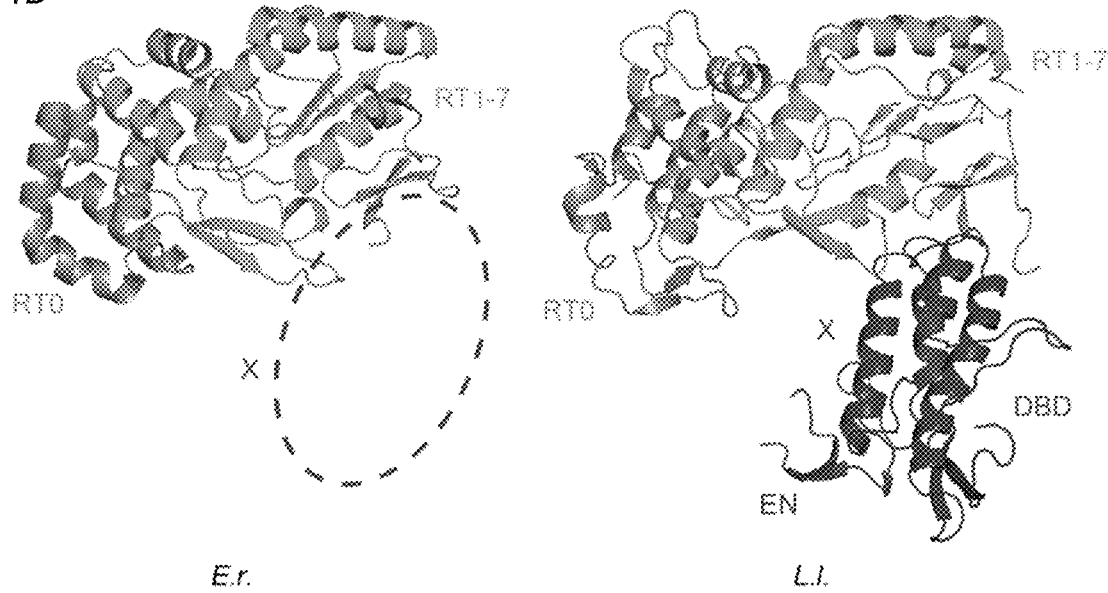
Fig. 4A- 4B

Fig. 5A
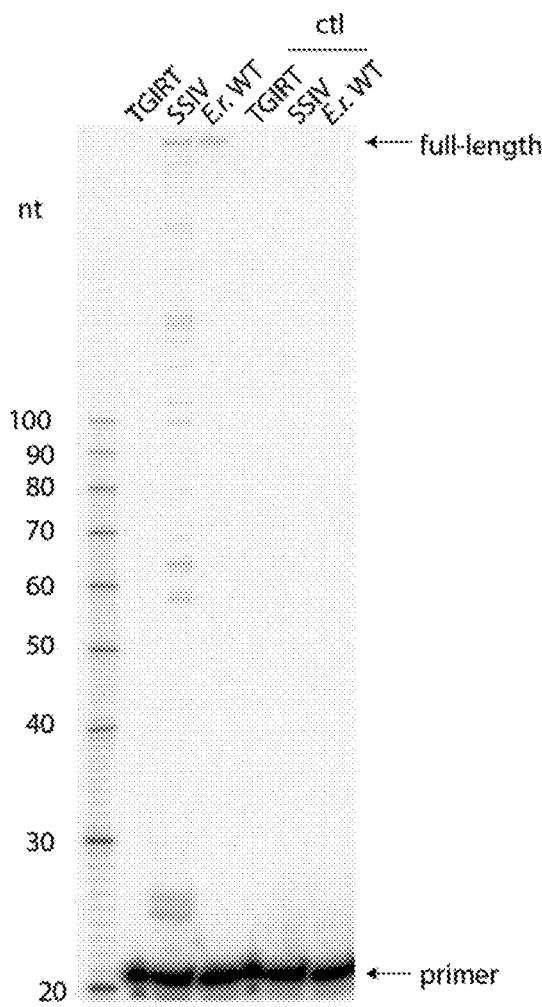
Fig. 5B
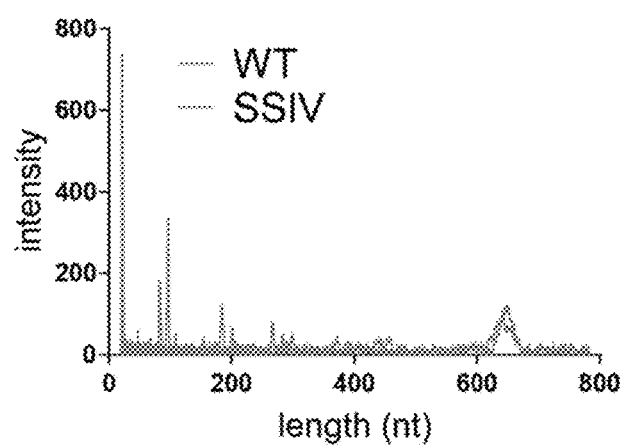
Fig. 5A- 5B

Fig. 7A
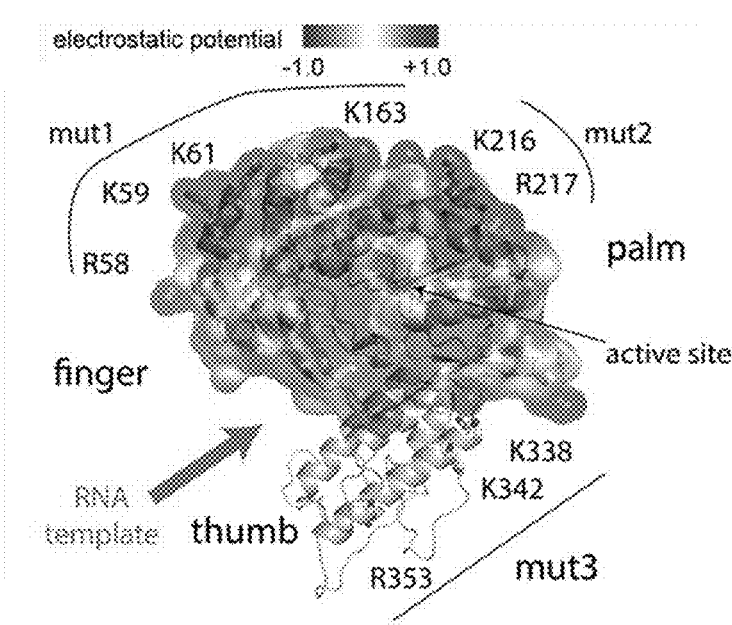
Fig. 7B
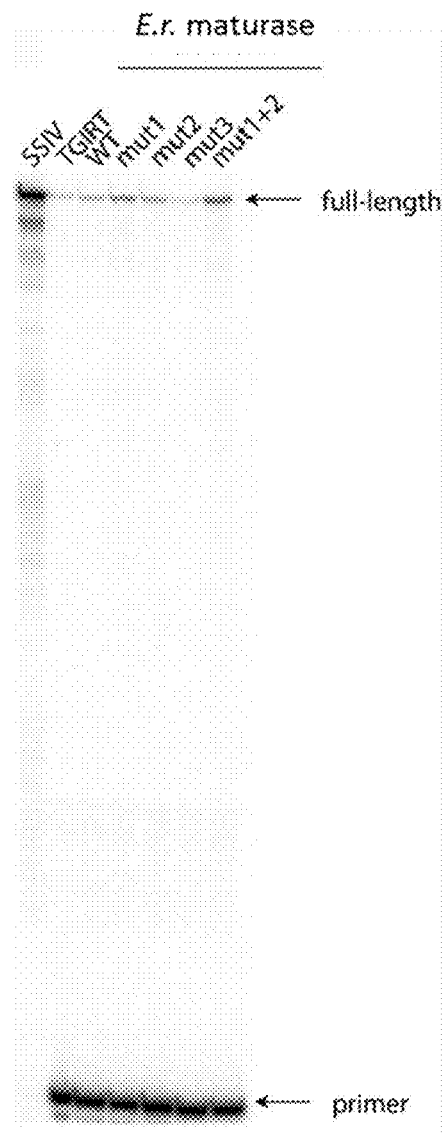
Fig. 7C
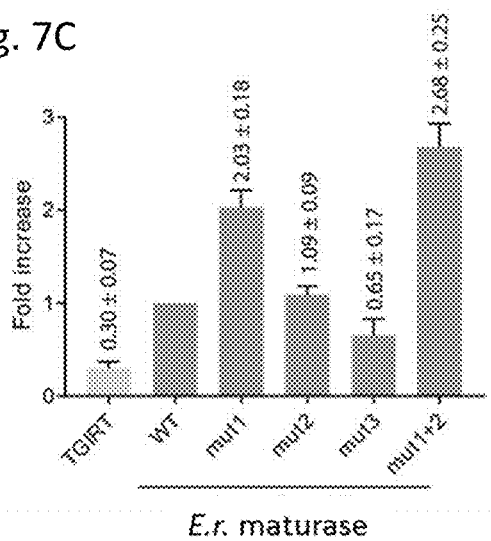
Fig. 7A- 7C

Fig. 8A
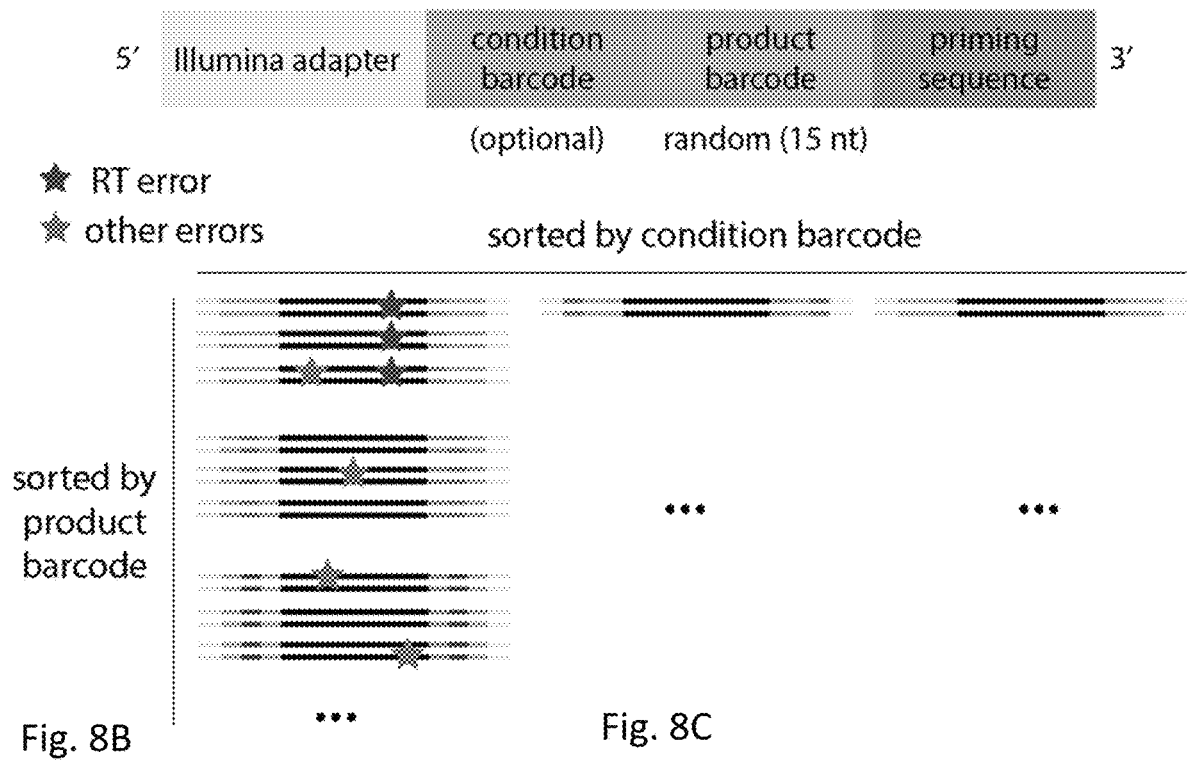
Fig. 8B
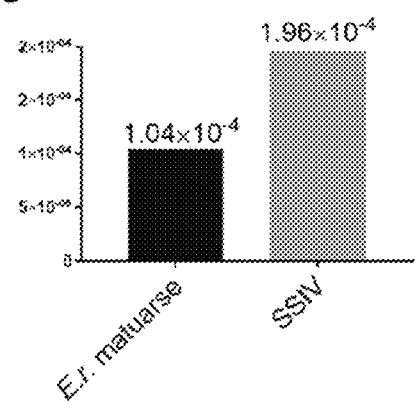
Fig. 8C
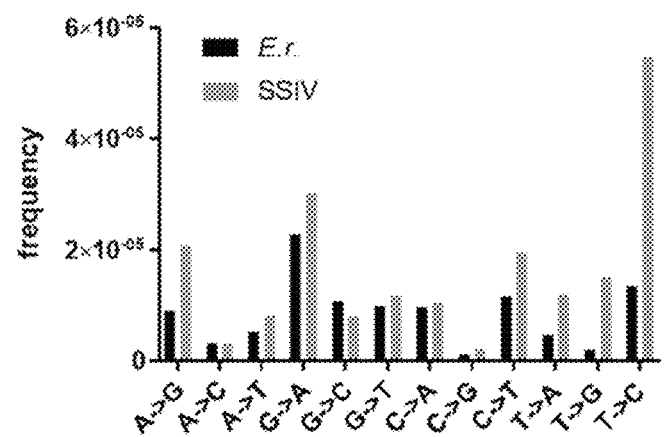
Fig. 8A- 8C

Fig. 12A
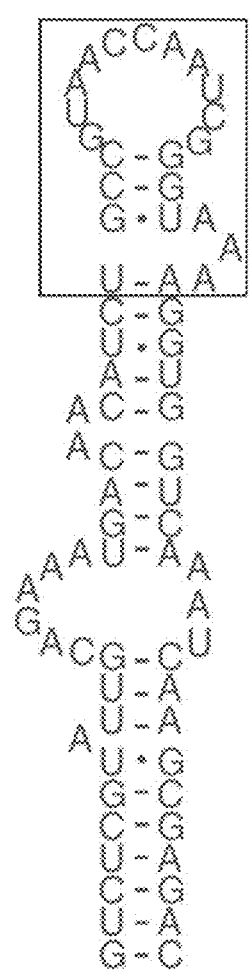
D4A
SEQ ID
NO: 23
Fig. 12B
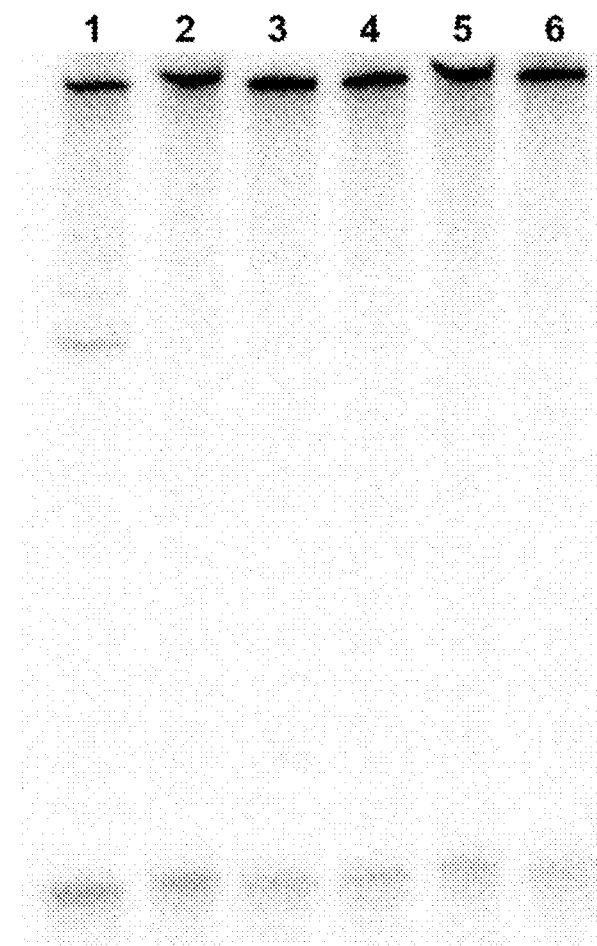
Fig. 12A- 12B

Fig. 14A
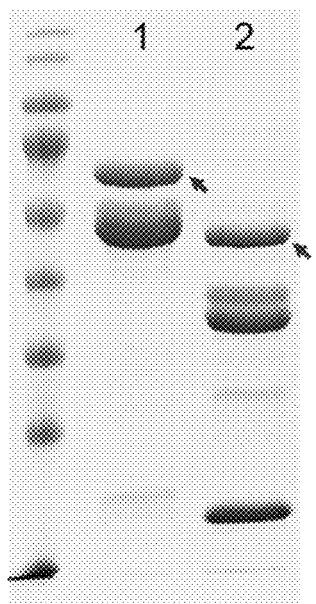
Fig. 14B
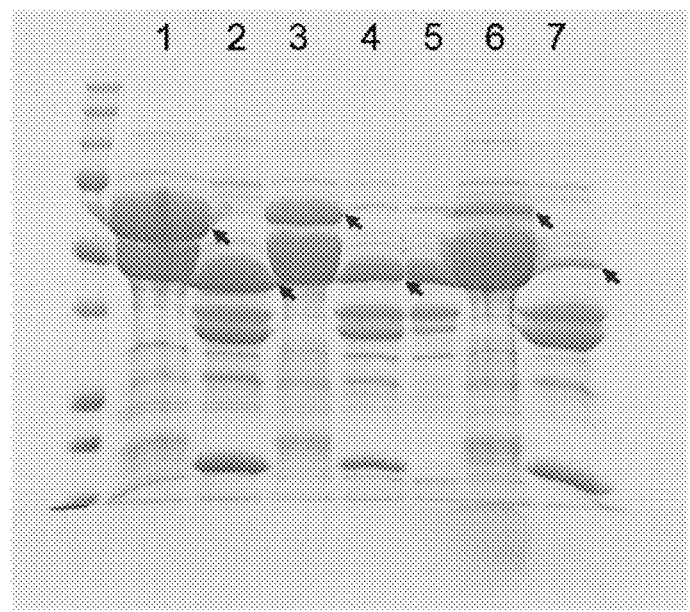
Fig. 14A- 14B

# REVERSE TRANSCRIPTASE AND METHODS OF USE

REFERENCE TO A "SEQUENCE LISTING," A TABLE, OR A COMPUTER PROGRAM LISTING APPENDIX SUBMITTED AS AN ASCII TEXT FILE

The Sequence Listing written in the ASCII text file: "047162_5243_00US_SequenceListing_ST25.TXT"; created on Dec. 18, 2019, and 43107 bytes in size is hereby incorporated by, reference.

CROSS-REFERENCE TO RELATED APPLICATIONS

This application is a U.S. national phase application filed under 35 U.S.C. § 371 claiming priority to International Patent Application No. PCT/US18/39738, filed Jun. 27, 2018, which is entitled to priority under 35 U.S.C. § 119(e) to U.S. Provisional Application No. 62/525,337, filed Jun. 27, 2017, the contents of each of which are incorporated by reference herein in their entireties.

STATEMENT REGARDING FEDERALLY SPONSORED RESEARCH OR DEVELOPMENT

This invention was made with government support under GM050313 and HG009622 awarded by National Institutes of Health. The government has certain rights in the invention.

BACKGROUND OF THE INVENTION

It is becoming increasingly important to monitor the complete sequences of long RNA molecules, such as viral genomes, regulatory noncoding RNAs, and mixtures of alternatively spliced messages in healthy and diseased tissues. In these cases, it is essential to sequence an entire transcript to link and monitor effects of multiple mutations, splice site choices, and other diversifications that influence downstream function. Unfortunately, accurate end-to-end Next-Generation Sequencing (NGS) of long transcripts is compromised by a paucity of robust, highly processive, accurate reverse-transcriptase (RT) enzymes to produce full-length complementary DNA (cDNA) transcripts for sequencing. As a result, RNA sequences are typically compiled from "short reads" that are joined to yield an average RNA sequence, which confounds the ability to monitor the linkage between multiple structural and sequence-related changes that occur within single transcripts. Continued advances in genomics research depend on the ability to solve this problem, and there is a need for the development of fundamentally new technologies for improving RNA sequencing, as it is a specific area of interest and a major unmet need.

Most commercial RT enzymes are derived from retroviral RTs, such as the SuperScript™ series that originated from MLV RT (Thermo Fisher Scientific™). A second family of commercial RTs was developed from thermophilic group II intron retrotransposons (TGIRT™ enzymes (InGex™)). While these enzymes were extensively optimized to achieve longer reads, they have not been shown to effectively copy very long or structured templates (>4000 nucleotides (nts)), and in no case has processivity or fidelity of these enzymes been quantitatively assessed, particularly on long templates.

Thus, there is a need in the art for an improved reverse transcriptase. The present invention addresses this unmet need.

SUMMARY OF THE INVENTION

In one aspect, the present invention provides a composition comprising a reverse transcriptase comprising a variant of *Eubacterium rectale* (E.r.) maturase. In one embodiment, the reverse transcriptase comprises one or more mutations relative to wildtype E.r. maturase, wherein the wildtype E.r. maturase comprises the amino acid sequence set forth in SEQ ID NO:14. In one embodiment, the reverse transcriptase comprises an amino acid sequence having greater than about 90% homology to the amino acid sequence set forth in SEQ ID NO: 14, further comprising one or more mutations relative to SEQ ID NO: 14.

In one embodiment, the reverse transcriptase comprises at least one mutation selected from the group consisting of: R58X, K59X, K61X, K163X, K216X, R217X, K338X, K342X, and R353X relative to SEQ ID NO: 14, wherein X denotes any amino acid. In one embodiment, the reverse transcriptase comprises at least one mutation selected from the group consisting of: R58A, K59A, K61A, K163A, K216A, R217A, K338A, K342A, and R353A relative to SEQ ID NO: 14. In one embodiment, the reverse transcriptase comprises an amino acid sequence selected from the group consisting of SEQ ID NO: 15, SEQ ID NO: 16, SEQ ID NO: 17 and SEQ ID NO: 18.

In one embodiment, the reverse transcriptase comprises at least one mutation selected from the group consisting of: mutation of the C-terminal DNA binding domain, mutation of the α-loop, a mutation to produce increased Lys-Glu pairs within rigid sections of the tertiary structure, addition of an exonuclease domain to enhance fidelity, mutation of the thumb domain, mutation of the catalytic site, and a substitution mutation wherein one or more residues or a domain in E.r. maturase is replaced with one or more residues or a domain derived from a maturase enzyme of an organism other than *Eubacterium rectale*.

In one embodiment, the mutation of the C-terminal DNA binding domain comprises at least one selected from the group consisting of: ΔC-term, K388X, R389X, K396X, K406X, R407X, and K423X, wherein X denotes any amino acid, wherein ΔC-term denotes deletion of the residues corresponding to position 387 to position 427 of SEQ ID NO: 14. In one embodiment, X is selected from the group consisting of: Alanine (A) and Serine (S).

In one embodiment, the mutation of the α-loop is selected from the group consisting of: mutations in the N-terminal portion of the α-loop, and substitution of the α-loop with an α-loop from another maturase reverse transcriptase.

In one embodiment, the mutation to produce increased Lys-Glu pairs within rigid sections of the tertiary structure comprises at least one selected from the group consisting of: L11X, L21X, and 513X. In one embodiment, X is Glutamic acid (E).

In one embodiment, the mutation of the thumb domain comprises at least one selected from the group consisting of: 5315X, E319X, Q323X, K338X, K342X, and R353X, wherein X denotes any amino acid. In one embodiment, the mutation of the thumb domain comprises at least one selected from the group consisting of: S315K, E319K, Q323K, K338A, K342A, and R353A.

In one embodiment, the mutation of the catalytic site comprises at least one selected from the group consisting of:

A225X, R114X, Y224X, I179X, M180X, I181X, E143X, K65X, and L201X, wherein X is any amino acid.

In one embodiment, the substitution mutation wherein a domain in E.r. maturase is replaced with a domain derived from a maturase enzyme of an organism other than *Eubacterium rectale* is selected from the group consisting of: replacement of the finger domain of E.r. maturase with a finger domain of another maturase reverse transcriptase, and replacement of the palm domain of E.r. maturase with a palm domain of another maturase reverse transcriptase. In one embodiment, the substitution mutation wherein one or more residues of E.r. maturase is replaced with one or more residues derived from a maturase enzyme of an organism other than *Eubacterium rectale* comprises at least one selected from the group consisting of: A29X, V82X, E104X, I129X, I137X, T161X, I168X, I170X, V171X, and M337X, where X denotes any amino acid. In one embodiment, the substitution mutation comprises at least one selected from the group consisting of A29S, V82I, E104P, I129Y, I137V, T161R, I168L, I170L, V171I, and M337T.

In one embodiment, the composition further comprises an agent that reduces non-specific binding of primer to the surface of the E.r. maturase. In one embodiment, the agent comprises a RNA stem-loop molecule. In one embodiment, the agent comprises a nucleic acid molecule derived from a group II intron. In one embodiment, the agent comprises D4A or a variant thereof.

In one embodiment, the reverse transcriptase has one or more improved properties selected from the group consisting of enhanced processivity, reduced error rate, reduced turnover, and improved thermocycling ability.

In one aspect, the present invention provides an isolated nucleic acid molecule encoding the reverse transcriptase described herein.

In one aspect, the present invention provides a method of performing reverse transcription, comprising contacting an RNA molecule with a composition comprising a reverse transcriptase comprising *Eubacterium rectale* (E.r.) maturase or a variant of E.r. maturase. In one embodiment, the E.r. maturase comprises an amino acid sequence having greater than about 90% homology to the amino acid sequence set forth in SEQ ID NO: 14.

In one embodiment, the E.r. maturase or a variant of E.r. maturase is used in an optimized reaction buffer, wherein the optimized reaction buffer comprises Tris at a concentration of about 10 mM to about 100 mM, KCl at a concentration of about 100 mM to about 500 mM, $MgCl_2$ at a concentration of about 0.5 mM to about 5 mM, DTT at a concentration of about 1 mM to about 10 mM, and wherein the optimized reaction buffer has a pH of about 8 to 8.5. In one embodiment, the optimized reaction buffer further comprises one or more protein stabilizing agents.

In one embodiment, the E.r. maturase or a variant of E.r. maturase is contacted with agent that reduces non-specific binding of primers to the E.r. maturase or variant of E.r. maturase. In one embodiment, the agent comprises a RNA stem-loop molecule. In one embodiment, the agent comprises a nucleic acid molecule derived from a group II intron. In one embodiment, the agent comprises D4A or a variant thereof.

In one aspect, the present invention provides a kit comprising a polypeptide comprising *Eubacterium rectale* (E.r.) maturase or a variant of E.r. maturase. In one embodiment, the E.r. maturase comprises an amino acid sequence having greater than about 90% homology to the amino acid sequence set forth in SEQ ID NO: 14.

In one embodiment, the kit further comprises an agent that reduces non-specific binding of primers to the E.r. maturase or variant of E.r. maturase. In one embodiment, the agent comprises a RNA stem-loop molecule. In one embodiment, the agent comprises a nucleic acid molecule derived from a group II intron. In one embodiment, the agent comprises D4A or a variant thereof.

In one embodiment, the kit further comprises an optimized reaction buffer, wherein the optimized reaction buffer comprises Tris at a concentration of about 10 mM to about 100 mM; KCl at a concentration of about 100 mM to about 500 mM, $MgCl_2$ at a concentration of about 0.5 mM to about 5 mM, DTT at a concentration of about 1 mM to about 10 mM, and wherein the optimized reaction buffer has a pH of about 8 to 8.5.

BRIEF DESCRIPTION OF THE DRAWINGS

The following detailed description of embodiments of the invention can be better understood when read in conjunction with the appended drawings. It should be understood that the invention is not limited to the precise arrangements and instrumentalities of the embodiments shown in the drawings.

FIG. 1, comprising FIG. 1A through FIG. 1C, depicts results from example experiments, demonstrating reverse transcription of the HCV RNA genome by the E.r. RT. (FIG. 1A) Diagram of the HCV RNA genome (top) and its structured regions (FIG. 1B). The E.r. RT was used to copy sections of this 9.6 kb RNA genome, using the primers shown with green arrows (FIG. 1A). Red arcs and lines in the core region (in yellow) indicate a RNA pseudoknot. (FIG. 1C) First-strand cDNAs synthesized by the E.r. RT. The cDNAs were synthesized from 5'-end labeled primers (as in FIG. 1A) and were analyzed by a 0.8% alkaline agarose gel. Letters above each lane indicate the primer used to generate each cDNA product, with approximate lengths (kb; kilobases) shown by markers at left. P' is the amount of full-length product over all extended product that includes full-length product and truncated products, which is a semi-quantitative metric of extreme processivity.

FIG. 2, comprising FIG. 2A and FIG. 2B, depicts results from example experiments, demonstrating the processivity of E.r. RT relative to Superscript IV (SSIV) and TGIRT on ~5 kb HCV RNA (primer F, as shown in FIG. 1A). FIG. 2A: First-strand cDNAs synthesized by the E.r. RT, SSIV and TGIRT. The cDNA was synthesized from 5'-end labeled primers (as in FIG. 1A) and were analyzed by a 0.8% alkaline agarose gel. Note inability of SSIV to traverse structured RNA segments. P' is the amount of full-length product over all extended product that includes full-length product and truncated products, which is a semi-quantitative metric of processivity. FIG. 2B: Intensity profile for gel lanes in (FIG. 2A) that represent RT products produced by E.r. maturase and SSIV.

FIG. 3, comprising FIG. 3A and FIG. 3B, depicts results from example experiments, demonstrating (FIG. 3A) the crystal structure of E.r. maturase RT domain (PDBID: 5HHL), with structural features indicated in color. (FIG. 3B) First-strand cDNA synthesized by wild-type E.r. maturase (WT) and the α-loop deletion mutant (Aa). The template for cDNA synthesis was the domain 3 of lincRNA RepA (643 nts). This figure demonstrates the importance of the α-loop for processivity.

FIG. 4, comprising FIG. 4A and FIG. 4B, depicts results from example experiments, demonstrating the sequence and structure of group II intron maturases. (FIG. 4A) Comparison of domain construction of different reverse transcriptases (RT). The name of each domain is labeled on the top, whereas the seven conserved sequence blocks in the RT domain (1-7) were labeled at the bottom. N-terminal extension (0) and insertions between conserved sequence blocks (2a, 3a and 7a) are observed in group II intron maturases but not in HIV RT. HIV: HIV RT p66 subunit. E.r.: maturase from group II intron in *Eubacterium rectale* (Eu.re.I2). maturase from group II intron in *Lactococcus lactis* (L.l.I1). (FIG. 4B) Three dimensional structure of group II intron maturases from E.r. and L.l. The PDB ID for E.r. maturase RT domain is 5HHL, and the PDB ID for L.l. full-length maturase is 5G2Y. The X domain (thumb) was not included in the crystallization construct of E.r. maturase and its position is indicated by a dotted oval. X: maturase X domain (thumb). DBD: DNA binding domain. EN: endonuclease domain.

FIG. 5, comprising FIG. 5A and FIG. 5B, depicts results from example experiments, demonstrating single turnover RT reaction on 643 nt lncRNA RepA D3. (FIG. 5A) Gel showing products from single-turnover RT reactions using RepA D3 as template catalyzed by different polymerases. The single turnover condition is achieved by adding excess RNA/DNA duplex to trap disassociated polymerases. In the control group (ctl), trap was incubated with polymerases prior to initiate the RT reaction with dNTPs. This experimental condition is significant because the trap prevents the polymerase from jumping back on the template and resuming polymerization after falling off of the template. Single turnover experiments with a trap provide the most rigorous estimates of processivity. It was observed that E.r. RT has excellent single turnover extension, SSIV has reasonable single-turnover extension (despite stops, see FIG. 5B) and TGIRT is unable to catalyze primer extension under these single turnover conditions, thereby preventing its use in single molecule or PacBio sequencing (FIG. 5A). SSIV: Superscript IV. (FIG. 5B) Intensity profile for gel lanes in (FIG. 5A) that represent RT products produced by E.r. maturase and SSIV.

FIG. 6, comprising (FIG. 6A) Three-dimensional model for E.r. maturase. The structure of the RT domain (finger and palm) was determined by X-ray crystallography (PDB ID: 5HHL), and the structure of thumb subdomain was created as a threading model by I-TASSER (Yang J et al., 2015, Nat Methods, 12:7-8) based on the thumb subdomain of LtrA (PDB ID: 5G2Y). Green arrow indicates the entry site for RNA template. YADD motif that coordinates the active site $Mg^{2+}$ ions is shown in red. Sequence conservation for the α-loop and surrounding regions from all maturase sequences in the database (Candales M A et al., 2012, Nucleic Acids Res, 40:D187-190) are shown under the structural model. The figure was created by web server WebLogo (Crooks G E et al., 2004, Genome Res, 14:1188-1190). (FIG. 6B) Gel showing the RT products produced by WT and Δloop mutant of E.r. maturase at different time points. (FIG. 6C) α-loop is in an open conformation in the cryo-EM structure of LtrA-LtrB intron complex (PDB ID: 5G2Y). In the cryo-EM structure, α-loop in LtrA forms a β-hairpin and is in an open conformation. This open conformation is stabilized by its interaction with group II intron D4A.

FIG. 7, comprising FIG. 7A through FIG. 7C, depicts results from example experiments, demonstrating positively charged RNA binding surface affects RT efficiency on lncRNA RepA Dl. (FIG. 7A) Three-dimensional model showing the positively charged RNA binding surface (blue) in the RT domain of E.r. maturase. The electrostatic surface potential of the RT domain was calculated by APBS (Baker N A et al., 2001, Proc Natl Acad Sci USA, 98:10037-10041) and PDB2PQR (Dolinsky T J et al., 2007, Nucleic Acids Res, 35:W522-525) and is presented as a transparent surface. Residues that are mutated in mut1, mut2, and mut3 constructs were shown as sticks. (FIG. 7B) Gel showing the RT products produced by TGIRT and different constructs of E.r. maturase. The RT reactions used RepA D1 as template, and were performed under multi-turnover conditions. (FIG. 7C) Fold increase of primer incorporation rate in RT reactions catalyzed by different enzymes compared to the WT E.r. maturase. Primer incorporation efficiency is the ratio of all extension products relative to the total amount of primer in the reaction (equal to all extension products plus unincorporated primers).

FIG. 8, comprising FIG. 8A through FIG. 8C, depicts results from example experiments, determining the error rate of various reverse transcriptases including E.r. maturase constructs, SSIV and TGIRT. (FIG. 8A) Single-molecule sequencing method: The schematic diagram of primers used for RT and 2nd strand synthesis is shown above. The principle underlying single-molecule sequencing is shown below. Only errors that are consistent in all sequencing reads and which share the same product barcode (UMI) are considered as RT errors (red stars). Errors that are inconsistent among reads that share the same product barcode (UMI) (green stars) originated from PCR amplification or the sequencing platform. (FIG. 8B) Overall substitutional frequency for E.r. maturase and SSIV. (FIG. 8C) Substitutional mutation spectrum for E.r. maturase and SSIV. There are 66 A, 65 G, 60 C and 69 T in the sequence used in this analysis. The error rate estimation shown here is highly conservative relative to previous estimates (Mohr et al., 2013, RNA, 19(7):958-70) because it was conducted on a single, well-defined sequence.

FIG. 9, comprising (FIG. 9A) Three-dimensional model for E.r. maturase. The structure of the RT domain (finger and palm) was determined by X-ray crystallography (PDB ID: 5HHL), and the structure of thumb subdomain was created as a threading model by I-TASSER (Yang J et al., 2015, Nat Methods, 12:7-8) based on the thumb subdomain of LtrA (PDB ID: 5G2Y). YADD motif that coordinates the active site $Mg^{2+}$ ions is shown in red. The "outer clamp" is shown in cyan that includes the β-hairpin in finger subdomain and the first α-helix in the thumb. The "inner clamp" is shown in yellow and contains α-loop in finger subdomain, primer grip in palm subdomain, and a highly conserved region in the second α-helix in the thumb subdomain. Green arrow indicates the entry site for RNA template. (FIG. 9B) RT products generated by E.r. maturase and SSIV under different salt concentrations. LncRNA RepA D3 was used as RT template. Salt concentrations in addition to the RT buffers were indicated at the top of each lane. (FIG. 9C) Comparison of the thumb subdomains in LtrA maturase (PDB ID: 5G2X) and p66 subunit of HIV RT (PDB ID: 2HMI). HIV RT (right) has a more extensive surface that could interact with RNA template compared to group II intron maturase (left).

FIG. 12, comprising FIG. 12A through FIG. 12B, depicts the results of experiments investigating the ability of D4A to improve E.r. maturase activity. The secondary structure of D4A (FIG. 12A) and reverse transcription by E.r maturase in the presence of D4A (FIG. 12B is shown). RepA D3 was used as the template and buffer 11 used to carry the reactions (Table 4).

FIG. 14, comprising FIG. 14A and FIG. 14B, depicts the results of experiments using SDS-PAGE to analyze protein production of E.r. maturase and E.r maturase variants. (FIG. 14A): The wild-type enzyme. Lane 1, purified protein by Ni-NTA. Lane 2, cleaved protein by SUMO protease. (FIG. 14B) The three E.r maturase variants. Lane 1, purified A29S/V82I/E104P protein by Ni-NTA. Lane 2, cleaved A29S/V82I/E104P protein by SUMO protease. Lane 3, purified I129Y protein by Ni-NTA. Lane 4, cleaved I129Y protein by SUMO protease. Lane 5, I129Y protein precipitate after SUMO protease treatment. Lane 6, purified M337T protein by Ni-NTA. Lane 7, cleaved M337T protein by SUMO protease. The positions of full-length proteins in the SDS-gels are indicated by arrows.

DETAILED DESCRIPTION

Figure 6A:
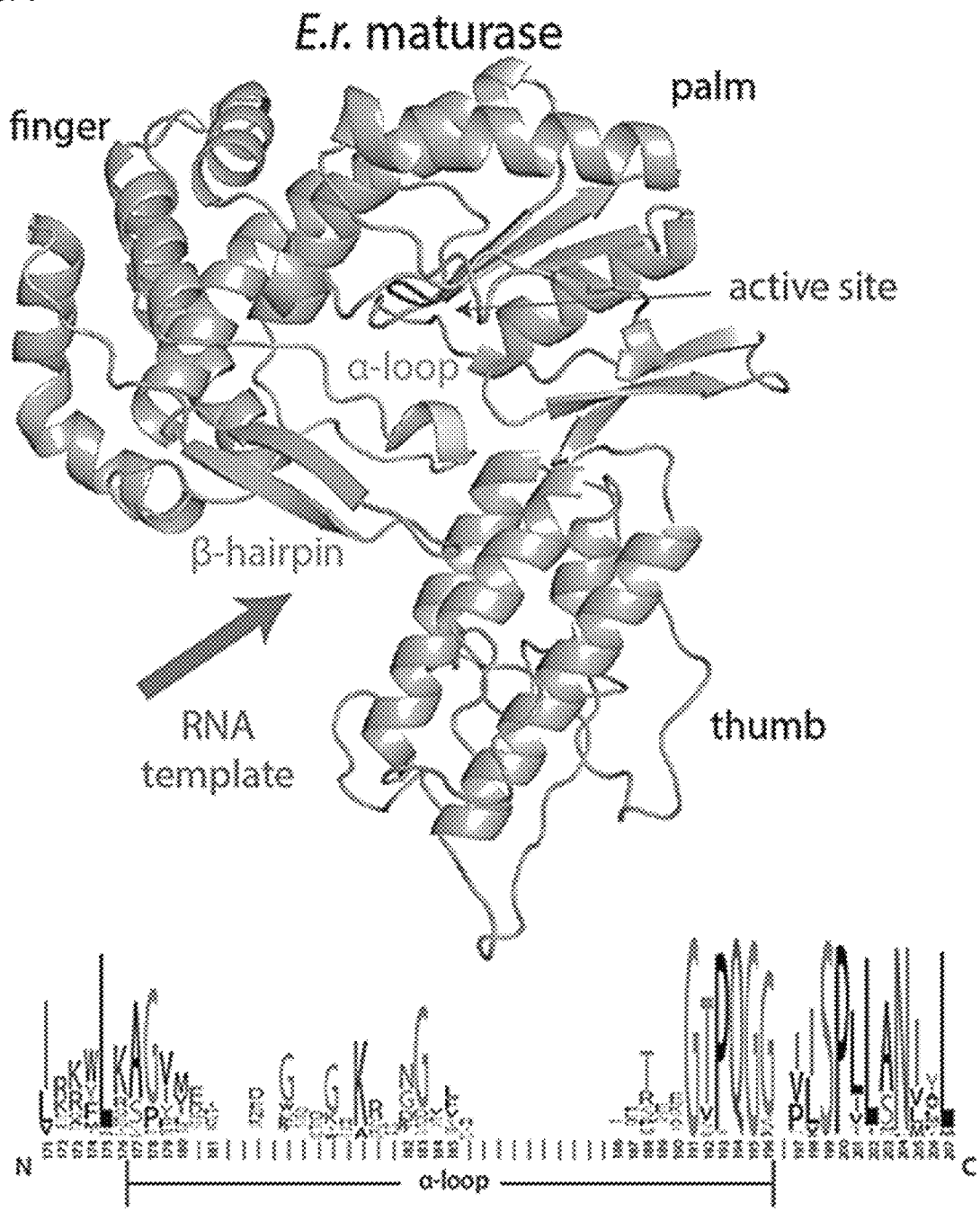
FIG. 6A through FIG. 6C, depicts results from example experiments, demonstrating that the α-loop is a processivity factor in group II intron maturases.

RNAs play important roles in epigenetic regulation, splicing, translation and virus infection, and they are direct reporters of gene expression levels. However, current understanding of the abundance, sequence and structure of RNAs is limited by the low processivity of reverse transcriptases (RT) that decode the information within RNA molecules. This limitation can be demonstrated by five examples. 1) Low RT processivity makes it difficult to obtain useful sequence information from highly structured or heavily modified RNA molecules. 2) In transcriptome-wide gene expression analyses, low RT processivity has been shown to bias read coverage and transcript quantification, and this bias is more severe in single-cell transcriptome profiling experiments (Archer et al., 2016, Cell Syst., 3(5):467-479). 3) In RNA structural probing methods such as SHAPE (Wilkinson et al., 2006, Nat Protoc., 1(3):1610-6; Spitale et al., 2015, Nature., 519(7544):486-90), low RT processivity results in background signal. At some locations, the background signal can be so strong that it obscures actual signal. 4) Low RT processivity limits the possibility of end-to-end long-read sequencing for RNA molecules using nanopore sequencing (Bolisetty et al., 2015, Genome Biol., 16:204) or SMRT sequencing (Pan et al., 2008, Nat Genet., 40(12): 1413-5). Long-read RNA sequencing is tremendously helpful for characterizing heterogeneous RNA sample, such as different splicing variants and RNAs with different modification sites or mutation sites. 5) Low RT processivity limits the development of single-molecule direct RNA sequencing using the PacBio platform, in contrast to a similar application for DNA sequencing (SMRT) that has already gained popularity (Chaisson et al., 2015, 517(7536):608-11). To date, direct RNA sequencing has only been conducted using short reads (<56 nts) (Ozsolak et al., 2009, Nature, 461 (7265):814-8) or modification sites (Vilfan et al., 2013, J Nanobiotechnology, 11:8), or using nanopore technology that has poor error rate (Laver et al., 2015, Biomol Detect Quantif, 3:1-8).

The present invention provides compositions and methods for reverse transcription. The present invention relates to the discovery that *Eubacterium rectale* (E.r.) maturase (also known as MarathonRT), and engineered variants thereof, are reverse transcriptases that display enhanced function. As described herein, E.r. maturase, and the engineered variants thereof, are highly processive reverse transcriptases that can be used in a wide variety of clinical and molecular biology procedures which utilize reverse transcription.

The present invention relates to compositions comprising E.r. maturase protein or variants thereof, compositions comprising nucleic acid molecules encoding E.r. maturase protein or variants thereof, methods for making the compositions, and methods for using the compositions in a reverse transcription reaction.

In one aspect, the present invention provides a composition comprising a reverse transcriptase or a nucleic acid molecule encoding a reverse transcriptase. In one embodiment, the reverse transcriptase is derived from E.r. maturase. In certain embodiments, the reverse transcriptase is modified relative to wildtype E.r. maturase. In certain embodiments, the reverse transcriptases of the present invention are thermocycling reverse transcriptases, thereby allowing for amplification of RNA templates in a single reaction. In certain embodiments, the reverse transcriptases of the present invention are functional at physiologic temperature, thereby allowing for efficient reverse transcription under conditions that reduce the degradation of the RNA template. In certain embodiments, the reverse transcriptases of the present invention efficiently copy long RNAs in a single turnover, thereby allowing the presently described reverse transcriptases to be used at lower reverse transcriptase concentrations and in single molecule sequencing technologies.

In one aspect, the present invention provides a composition comprising an agent that improves RT activity of E.r. maturase or variants thereof. For example, in some embodiments, the composition comprises an agent that reduces non-specific binding of primers to the positively charged surface of E.r. maturase or variants thereof. In some embodiments, the agent that reduces non-specific binding of primers to the positively charged surface of E.r. maturase or variants thereof comprises a protein, nucleic acid molecule, small molecule, or other compound that prevent or reduce non-specific binding. In one embodiment, the agent comprises a nucleic acid molecule, such as a single stranded or double stranded DNA or RNA molecule. For example, in one embodiment, the agent comprises an RNA molecule, such as a double stranded RNA or a single stranded RNA hairpin or stem-loop molecule. In some embodiments, the agent comprises a nucleic acid molecule derived from a group II intron, such as the E.r. group II intron. In one embodiment, the agent comprises D4A helix, a nucleic acid molecule derived from E.r. group II intron. In some embodiments, the agent comprises a variant derived from D4A, including, but not limited to, a fragment of D4A, a D4A mutant, or a nucleic acid molecule having substantial homology to D4A.

In one aspect, the present invention provides an optimized reaction buffer that enhances the activity of E.r. maturase or variants thereof. In some embodiments, the optimized reaction buffer comprises one or more of: Tris at a concentration of about 10 mM to about 100 mM; KCl at a concentration of about 100 mM to about 500 mM, $MgCl_2$ at a concentration of about 0.5 mM to about 5 mM, and DTT at a concentration of about 1 mM to about 10 mM. In one embodiment, the optimized reaction buffer has a pH of about 8 to 8.5.

In some embodiments, the optimized reaction buffer further comprises a protein stabilizing agent. Exemplary protein stabilizing agents include, but are not limited to, osmolytic stabilizers such as glycerol, erythritol, arabitol, sorbitol, mannitol, xylitol, mannisdomannitol, glucosylglycerol, glucose, fructose, sucrose, trehalose, isofluorosid, dextrans, levans, and polyethylene glycol; amino acids and derivatives thereof such as glycine, alanine, proline, taurine, betaine, octopine, glutamate, sarcosine, γ-aminobutyric acid, trimethylamine, N-oxide (TMAO); ionic stabilizers such as citrate, sulfates, acetate, phosphates, and quaternary amines; and proteins such as bovine serum albumin (BSA).

In one aspect, the present invention relates to a method of reverse transcription using a reverse transcriptase comprising E.r. maturase, or a variant thereof. In certain aspects, the method provides for reverse transcription at physiologic temperatures, or at lower temperatures relative to that required when using non-E.r maturase-derived reverse transcriptases. In certain instances, the lower temperature of the reverse transcription reaction provides a decreased rate of degradation of the RNA molecule during the reaction, relative to the rate of degradation of an RNA molecule in a reverse transcription reaction that uses a non-E.r maturase-derived reverse transcriptase. In another embodiment, the RNA molecule to be reverse transcribed is a long or complex RNA molecule. In another embodiment, the reverse transcription reaction efficiently creates full-length DNA products. In another embodiment, the reverse transcription reaction requires less E.r. maturase protein relative to the amount of reverse transcriptase required in a reverse transcription reaction which uses another reverse transcriptase. In one embodiment, the method comprises amplification of RNA in a single reaction, made possible by the true thermocycling ability of the reverse transcriptases described herein.

Definitions

Unless defined otherwise, all technical and scientific terms used herein have the same meaning as commonly understood by one of ordinary skill in the art to which this invention belongs. It is also to be understood that the terminology used herein is for the purpose of describing particular embodiments only, and is not intended to be limiting.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

As used herein, "autologous" refers to a biological material derived from the same individual into whom the material will later be re-introduced.

As used herein, "allogeneic" refers to a biological material derived from a genetically different individual of the same species as the individual into whom the material will be introduced.

The terms "cells" and "population of cells" are used interchangeably and generally refer to a plurality of cells, i.e., more than one cell. The population may be a pure population comprising one cell type. Alternatively, the population may comprise more than one cell type. In the present invention, there is no limit on the number of cell types that a cell population may comprise.

"Encoding" refers to the inherent property of specific sequences of nucleotides in a polynucleotide, such as a gene, a DNA, or an RNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Isolated" means altered or removed from the natural state. For example, a nucleic acid or a peptide naturally present in a living organism is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a conditional manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

In some embodiments, the present invention relates to a reverse transcriptase comprising E.r. maturase, or a variant thereof, for use in a reverse transcription reaction. The reverse transcriptases of the present invention are described herein to have one or more improved properties, including but not limited to, enhanced processivity, reduced error rate, reduced turnover, and improved thermocycling ability. The presently described reverse transcriptases thus have enhanced functionality that allow them to be utilized in a wide variety of applications including, but not limited to, RNA sequencing, RNA amplification, next generation sequencing, nanopore sequencing, RT-PCR, quantitative PCR, cDNA synthesis, cDNA library synthesis, splice site characterization, viral RNA sequencing, single cell sequencing, RNA structure probing, and the like.

In one aspect, the present invention provides a composition comprising a reverse transcriptase or a nucleic acid molecule encoding a reverse transcriptase. In one embodiment, the reverse transcriptase is derived from E.r. maturase. In certain embodiments, the reverse transcriptase comprises an E.r. maturase variant that is modified relative to wildtype E.r. maturase. In certain embodiments, the E.r. maturase variant comprises one or more modifications in the α-loop, finger domain, thumb domain, C-terminal DNA binding domain, or in the positively charged protein surface.

In one aspect, the invention provides a method of engineering variants of E.r. maturase. In some embodiments, the variants have at least one enhanced property relative to unmodified E.r. maturase. In some embodiments, the variants are engineered by mutating E.r. maturase to be improved relative to unmodified E.r. maturase with regard to the protein's purity, stability, processivity, turnover, error rate, or other properties. In some embodiments, the variants are engineered by modifying the solution conditions relative to unmodified solution conditions to create an improved composition comprising E.r. maturase or a variant thereof, with regard to the protein's purity, stability, processivity, turnover, error rate, or other properties.

In one aspect, the present invention provides a method for reverse transcription. For example, in one embodiment, the method comprises contacting an RNA molecule with one or more reverse transcriptase molecules described herein. As described herein, using the presently described reverse transcriptases allows for the reverse transcription reaction to occur at lower temperatures and at lower reverse transcriptase concentrations. Further, the use of the presently described reverse transcriptases allows for production of longer reads. Further still, the thermocycling ability of the presently described reverse transcriptases allows for RNA amplification using a single reaction.

Compositions

In one embodiment, the invention is a composition comprising a reverse transcriptase. In one embodiment, the reverse transcriptase is derived from E.r. maturase. For example, in certain embodiments, the reverse transcriptase comprises E.r. maturase, or a variant thereof. In one embodiment, E.r. maturase is modified relative to unmodified E.r. maturase. For example, in certain embodiments, the variant comprises one or more point mutations, insertion mutations, or deletion mutations, relative to wildtype E.r. maturase. In certain embodiments, the variant comprises a fusion protein comprising E.r. maturase, E.r. maturase mutant, or E.r. maturase domain.

In one embodiment, the composition comprises wildtype E.r. maturase. The amino acid sequence of wildtype E.r. maturase is provided below and is denoted as SEQ ID NO: 14:

```
                                          SEQ ID NO: 14
MDTSNLMEQILSSDNLNRAYLQVVRNKGAEGVDGMKYTELKEHLAKNGETI

KGQLRTRKYKPQPARRVEIPKPDGGVRNLGVPTVTDRFIQQAIAQVLTPIY

EEQFHDHSYGFRPNRCAQQAILTALNIMNDGNDWIVDIDLEKFFDTVNHDK

LMTLIGRTIKDGDVISIVRKYLVSGIMIDDEYEDSIVGTPQGGNLSPLLAN

IMLNELDKEMEKRGLNFVRYADDCIIMVGSEMSANRVMRNISRFIEEKLGL

KVNMTKSKVDRPSGLKYLGFGFYFDPRAHQFKAKPHAKSVAKFKKRMKELT

CRSWGVSNSYKVEKLNQLIRGWINYFKIGSMKTLCKELDSRIRYRLRMCIW

KQWKTPQNQEKNLVKLGIDRNTARRVAYTGKRIAYVCNKGAVNVAISNKRL

ASFGLISMLDYYIEKCVTC (E.r. maturase).
```

The full-length E.r. maturase comprises a "secondary" RNA binding site and DNA binding domain that can influence stability, specificity, and efficiency of reverse transcription of an RNA template. In one embodiment, the reverse transcriptase comprises an E.r. maturase variant where one or more secondary RNA binding sites on the surface of the protein are mutated to reduce nonspecific binding of the reverse transcription protein to the RNA template, thereby promoting binding at the polymerase cleft and facilitating enzyme turnover. In one such embodiment, a variant of E.r. maturase comprises at least one point mutation selected from the group R58X, K59X, K61X, K163X, K216X, R217X, K338X, K342X, and R353X wherein X denotes any amino acid. In another such embodiment, a variant of E.r. maturase comprises at least one point mutation selected from the group R58A, K59A, K61A, K163A, K216A, R217A, K338A, K342A, and R353A.

In one embodiment, the reverse transcriptase comprises an E.r. maturase variant (referred to herein as E.r. maturase mut1; and denoted as SEQ ID NO: 15) comprising the point mutations of: R58A, K59A, K61A, and K163A, relative to wildtype E.r. maturase.

In one embodiment, the reverse transcriptase comprises an E.r. maturase variant (referred to herein as E.r. maturase mut2; and denoted as SEQ ID NO: 16) comprising the point mutations of: K216A and K217A, relative to wildtype E.r. maturase.

In one embodiment, the reverse transcriptase comprises an E.r. maturase variant (referred to herein as E.r. maturase mut1+mut2; and denoted as SEQ ID NO: 17) comprising the point mutations of: R58A, K59A, K61A, K163A, K216A, and R217A, relative to wildtype E.r. maturase.

In one embodiment, the reverse transcriptase comprises an E.r. maturase variant (referred to herein as E.r. maturase mut3; and denoted as SEQ ID NO: 18) comprising the point mutations of: K338A, K342A, and R353A relative to wildtype E.r. maturase.

In one embodiment, the reverse transcriptase comprises an E.r. maturase variant comprising one or more mutations in the C-terminal DNA binding domain of E.r. maturase. In one such embodiment, a variant of E.r. maturase comprises at least one point mutation selected from the group K388X, R389X, K396X, K406X, R407X, and K423X, wherein X denotes any amino acid. In another such embodiment, a variant of E.r. maturase comprises at least one point mutation selected from the group K388A, R389A, K396A, K406A, R407A, and K423A. In another such embodiment, a variant of E.r. maturase comprises at least one point mutation selected from the group K388S, R389S, K396S, K406S, R407S, and K423S. In another such embodiment, the C-terminal sequence residues 387-427 are deleted relative to wildtype E.r. maturase, wherein the 4387-427 variant has the sequence (SEQ ID NO: 22)
$^{387}$GKRIAYVCNKGAVNVAISNKRLASFGLISMLDYYIEKCVTC$^{427}$ deleted.

E.r. maturase has a loop (the α-loop), the sequence of which is $^{180}$MIDDEYEDSIV<u>GTPQGG</u>$^{196}$ (SEQ ID NO: 20), wherein the bold and underlined fragment is highly conserved among maturase reverse transcriptases. In one embodiment, the reverse transcriptase of the present invention comprises an E.r. maturase variant, comprising one or more mutations in the α-loop of E.r maturase. In one embodiment, the E.r. maturase variant comprises one or more mutations in the N-terminal region of the α-loop. Specifically, in one embodiment, at least one point mutation is created relative to the unmodified sequence MIDDEYEDSIV (SEQ ID NO: 21) of the α-loop. In one embodiment, the mutation is at least one selected from the group: M180X, I181X, D182X, D183X, E184X, Y185X, E186X, D187X, S188X, I189X, V190X, wherein X denotes any amino acid. In one such embodiment, the at least one point mutation (X) is selected from the group: alanine, polar amino acid (e.g., Gln), electrostatic amino acid (e.g. Glu), and a combination thereof. In another such embodiment, the α-loop is engineered to be more flexible by substituting positions in the N-terminal region with one or more glycines. In another such embodiment, the α-loop is engineered to be more stiff by substituting positions in the N-terminal region with one or more alanines. In one embodiment, the mutation is a deletion of at least one residue of the α-loop. In one embodiment, the reverse transcriptase of the present invention comprises an E.r. maturase variant in which residues 182-192 are substituted with two glycine residues (Δloop; SEQ ID NO:19).

E.r. maturase can perform reverse transcription at lower temperatures relative to other reverse transcriptases, and the engineering of a more thermostable E.r. maturase would enable amplification of RNA templates in a single reaction (i.e., without using DNA→DNA amplification reactions). Analysis of thermophilic protein structure and function suggests that they tend to have larger numbers of side-chain hydrogen bonds and salt-bridges within rigid sections of the tertiary structure. Therefore, in one embodiment, the reverse transcriptase of the present invention comprises an E.r. maturase variant, engineered to have Lys-Glu pairs at positions that are proximal in 3-D space, according to the structure of the enzyme (Zhao C et al., 2016, Nature structural & molecular biology, 23(6):558-65). In one such embodiment, the variant comprises at least one point mutation selected from the group L11E (which can form a salt bridge with R56), L21E (which can form a salt bridge with K41), and S13E (which can form a salt bridge with K52).

In one embodiment, the reverse transcriptase of the present invention comprises an E.r. maturase variant, engineered to comprise a proofreading (e.g., 3'-5' exonuclease) domain to enhance fidelity. In one such embodiment, the proofreading domain comprises an exonuclease domain. In another such embodiment, the proofreading domain is appended to the C-terminus of the E.r. maturase variant. In another such embodiment, the proofreading domain is appended to the C-terminus of the E.r. maturase variant through a linker molecule or sequence (see, for example, Ellefson, J W et al., 2016, Science, 352(6293):1590-3).

Maturase reverse transcriptases are generally conserved among species, but some may have additional, beneficial properties compared to others. Therefore, in one embodiment, the reverse transcriptase of the present invention comprises an E.r. maturase variant, wherein at least one fragment or domain of E.r. maturase is replaced with a fragment or domain from a maturase reverse transcriptase from a species other than *Eubacterium rectale*. For example, in one embodiment, the RT domain (finger and palm) of E.r. maturase reverse transcriptase is replaced with the RT domain from a thermophilic maturase reverse transcriptase to enhance thermostability. In another embodiment, the α-loop of E.r. maturase is replaced by a longer α-loop from another maturase reverse transcriptase to enhance processivity. In one embodiment, one or more amino acids are substituted with hydrophobic amino acids or charged amino acids in order to improve thermostability.

In one embodiment, the reverse transcriptase of the present invention comprises an E.r. maturase variant, wherein one or more residues are substituted with one or more residues derived from a maturase enzyme from an organism other than *Eubacterium rectale*. For example, in some embodiments, the E.r. maturase variant can comprise one or more point mutations based on conserved residues in thermophilic maturases. In one embodiment, the variant comprises at least one mutation selected from the group: A29X, V82X, E104X, I129X, I137X, T161X, I168X, I170X, V171X, and M337X, where X denotes any amino acid. In one embodiment, the mutation is at least one selected from the group: A29X, V82X, E104X, I129X, I137X, T161X, I168X, I170X, V171X, and M337X, where X denotes any amino acid. In one embodiment, the variant comprises at least one mutation selected from the group: A29S, V82I, E104P, I129Y, I137V, T161R, I168L, I170L, V171I, and M337T. In one embodiment, the variant comprises a triple point mutation of A29S/V82I/E104P. In certain instances, these mutations improve upon the thermostability of the enzyme.

In one embodiment, the reverse transcriptase of the present invention comprises an E.r. maturase variant, comprising one or more mutations in the thumb domain relative to wildtype E.r. maturase.

In one embodiment, the variant comprises at least one point mutation selected from the group consisting of K338X, K342X, and R353X, wherein X denotes any amino acid. In another such embodiment, the variant comprises at least one point mutation selected from the group consisting of K338A, K342A, and R353A.

In one such embodiment, one or more mutations are incorporated on the surface of the thumb domain, optimizing its ability to clasp the template. In one such embodiment, the variant comprises at least one point mutation selected from the group consisting of S315X, E319X, and Q323X, wherein X denotes any amino acid. In another such embodiment, the variant comprises at least one point mutation selected from the group consisting of S315K, E319K, and Q323K.

In one embodiment, the composition comprises an isolated polypeptide comprising a reverse transcriptase. In one embodiment, the reverse transcriptase is derived from E.r. maturase. For example, in one embodiment, the polypeptide comprises E.r. maturase, or a variant thereof. Exemplary amino acid sequences of the E.r. maturase-derived reverse transcriptases of the present invention include, but are not limited to, SEQ ID NO:14 (E.r. maturase), SEQ ID NO:15 (E.r. maturase mut1), SEQ ID NO:16 (E.r. maturase mut2), SEQ ID NO:17 (E.r. maturase mut1+mut2), SEQ ID NO:18 (E.r. maturase mut3) and SEQ ID NO:19 (E.r. maturase Δloop). However, the present invention is not limited to these sequences. Rather the present invention encompasses any reverse transcriptase derived from E.r. maturase or a variant thereof.

In one embodiment, the polypeptide comprises a fragment of E.r. maturase or variant thereof that mimics the ability of E.r. maturase to perform reverse transcription. In one embodiment, the polypeptide comprises a derivative of the E.r. maturase or variant thereof. In certain embodiments, the polypeptide comprises an amino acid sequence selected from a fragment or derivative of SEQ ID NO:14, a fragment or derivative of SEQ ID NO:15, a fragment or derivative of SEQ ID NO:16, a fragment or derivative of SEQ ID NO:17, a fragment or derivative of SEQ ID NO:18, and a fragment or derivative of SEQ ID NO:19.

In one embodiment, the reverse transcriptase of the invention comprises one or mutations in the catalytic active-site to reduce the fidelity of the enzyme, which will enhance its value for RNA structure mapping since structure-specific lesions that are used to probe RNA structure are flagged by misincorporation events. Similarly, mutations that increase the error rate of the enzyme can be used with certain RNA and transcriptome mapping experiments. Therefore, in some embodiments, the polypeptide comprises at least one mutation selected from the group: A225X, R114X, Y224X, I179X, M180X, I181X, E143X, K65X, L201X, wherein X denotes any amino acid. Specifically, mutations at A225 (such as A225V, A225S, A225M or A225V), mutations at R114 (such as R114K, R114A), mutations at Y224 (such as Y224F), mutations at I179 (such as I179F), mutations at M180 (such as M180V), mutations at I181 (such as I181W), mutations at E143 (such as E143A or E143K), mutations at K65 (such as K65A), mutations at L201 (such as L201A or L201T), may be used, alone or in combination.

In one embodiment, the composition of the present invention comprises a polypeptide comprising *Roseburia intestinalis* (R.i.) maturase, or a variant or fragment thereof. In one such embodiment, the R.i. maturase comprises one or more mutations corresponding to one or more mutations described herein.

Reverse transcriptases of the present invention may produce more product (e.g., full length product) at particular temperatures compared to other reverse transcriptases. In one aspect, comparisons of full length product synthesis are made at different temperatures (e.g., one temperature being lower, such as between 37° C. and 50° C., and one temperature being higher, such as between 50° C. and 78° C.) while keeping all other reaction conditions similar or the same. The amount of full length product produced may be determined using techniques well known in the art, for example, by conducting a reverse transcription reaction at a first temperature (e.g., 37° C., 38° C., 39° C., 40° C., etc.) and determining the amount of full length transcript produced, conducting a second reverse transcription reaction at a temperature higher than the first temperature (e.g., 45° C., 50° C., 52.5° C., 55° C., etc.) and determining the amount of full length product produced, and comparing the amounts produced at the two temperatures. A convenient form of comparison is to determine the percentage of the amount of full length product at the first temperature that is produced at the second (i.e., elevated) temperature. The reaction conditions used for the two reactions (e.g., salt concentration, buffer concentration, pH, divalent metal ion concentration, nucleoside triphosphate concentration, template concentration, reverse transcriptase concentration, primer concentration, length of time the reaction is conducted, etc.) may be the same for both reactions. Suitable reaction conditions may be determined by those skilled in the art using routine techniques and examples of such conditions are provided herein.

The reverse transcriptases of the invention may produce at least about 5%, at least 10%, at least 15%, at least 25%, at least 50%, at least 75%, at least 100%, or at least 200% more product or full length product compared to the corresponding control reverse transcriptase under the same reaction conditions and temperature. The reverse transcriptases of the invention may produce from about 10% to about 200%, from about 25% to about 200%, from about 50% to about 200%, from about 75% to about 200%, or from about 100% to about 200% more product or full length product compared to a control reverse transcriptase under the same reaction conditions and incubation temperature. The reverse transcriptases of the invention may produce at least 2 times, at least 3 times, at least 4 times, at least 5 times, at least 6 times, at least 7 times, at least 8 times, at least 9 times, at least 10 times, at least 25 times, at least 50 times, at least 75 times, at least 100 times, at least 150 times, at least 200 times, at least 300 times, at least 400 times, at least 500 times, at least 1000 times, at least 5,000 times, or at least 10,000 times more product or full length product compared to a control reverse transcriptase under the same reaction conditions and temperature.

Reverse transcriptases of the present invention may have an increased thermostability at elevated temperatures as compared to corresponding control reverse transcriptases. They may show increased thermostability in the presence or absence an RNA template. In some instances, reverse transcriptases of the invention may show an increased thermostability in both the presence and absence of an RNA template. Those skilled in the art will appreciate that reverse transcriptase enzymes are typically more thermostable in the presence of an RNA template. The increase in thermostability may be measured by comparing suitable parameters of the modified or mutated reverse transcriptase of the invention to those of a corresponding un-modified or un-mutated reverse transcriptase. Suitable parameters to compare include, but are not limited to, the amount of product and/or full length product synthesized by the reverse transcriptases of the invention at an elevated temperature compared to the amount or product and/or full length product synthesized by a control reverse transcriptase at the same temperature, and/or the half-life of reverse transcriptase activity at an elevated temperature of a reverse transcriptase of the invention at an elevated temperature compared to that of a control reverse transcriptase.

A reverse transcriptase of the invention may have an increase in thermostability at a particular temperature of at least about 1.5 fold (e.g., from about 1.5 fold to about 100 fold, from about 1.5 fold to about 50 fold, from about 1.5 fold to about 25 fold, from about 1.5 fold to about 10 fold) compared, for example, to the control reverse transcriptase. A reverse transcriptase of the invention may have an increase in thermostability at a particular temperature of at least about 10 fold (e.g., from about 10 fold to about 100 fold, from about 10 fold to about 50 fold, from about 10 fold to about 25 fold, or from about 10 fold to about 15 fold) compared, for example, to the control reverse transcriptase. A reverse transcriptase of the invention may have an increase in thermostability at a particular temperature of at least about 25 fold (e.g., from about 25 fold to about 100 fold, from about 25 fold to about 75 fold, from about 25 fold to about 50 fold, or from about 25 fold to about 35 fold) compared to the control reverse transcriptase.

The polypeptide of the present invention may be made using chemical methods. For example, polypeptides can be synthesized by solid phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer. The polypeptide may be made by recombinant means or by cleavage from a longer polypeptide. The polypeptide may be confirmed by amino acid analysis or sequencing.

The invention should also be construed to include any form of a polypeptide having substantial homology to a reverse transcriptase disclosed herein. For example, a polypeptide which is "substantially homologous" is about 50% homologous, about 70% homologous, about 80% homologous, about 90% homologous, about 95% homologous, about 96% homologous, about 97% homologous, about 98% homologous, about 99% homologous, or about 99.5% homologous to an amino acid sequence of a reverse transcriptase disclosed herein.

In some embodiments, the composition comprises a reverse transcriptase comprising an amino acid sequence that is about 50%, about 70%, about 80%, about 90%, about 91%, about 92%, about 93%, about 94%, about 95%, about 96%, about 97%, about 98%, about 99%, or about 99.5% homologous to E.r. maturase or E.r. maturase variant described herein.

In some embodiments, the composition comprises a reverse transcriptase comprising an amino acid sequence that is about 50%, about 70%, about 80%, about 90%, about 91%, about 92%, about 93%, about 94%, about 95%, about 96%, about 97%, about 98%, about 99%, or about 99.5% homologous to the amino acid sequence set forth in SEQ ID NO: 14, SEQ ID NO: 15, SEQ ID NO: 16, SEQ ID NO: 17 or SEQ ID NO: 18.

In some embodiments, the composition comprises a reverse transcriptase comprising an amino acid sequence that is about 50%, about 70%, about 80%, about 90%, about 91%, about 92%, about 93%, about 94%, about 95%, about 96%, about 97%, about 98%, about 99%, or about 99.5% homologous to the amino acid sequence set forth in SEQ ID NO: 14, SEQ ID NO: 15, SEQ ID NO: 16, SEQ ID NO: 17 or SEQ ID NO: 18, wherein the reverse transcriptase comprises one or more of the mutations described herein.

In one aspect, the present invention provides a composition comprising an agent that improves RT activity of E.r. maturase or variants thereof. For example, in some embodiments, the composition comprises an agent that reduces non-specific binding of primers to the positively charged surface of E.r. maturase or variants thereof. In some embodiments, the agent that reduces non-specific binding of primers to the positively charged surface of E.r. maturase or variants thereof comprises a peptide or protein, including, but not limited to, heparin.

The variants of the polypeptides according to the present invention may be (i) one in which one or more of the amino acid residues are substituted with a conserved or non-conserved amino acid residue, and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two polypeptides is determined by comparing the amino acid sequence and its conserved amino acid substitutes of one polypeptide to a sequence of a second polypeptide. Variants are defined to include polypeptide sequences different from the original sequence, for example, different from the original sequence in less than 40% of residues per segment of interest, different from the original sequence in less than 25% of residues per segment of interest, different by less than 10% of residues per segment of interest, or different from the original protein sequence in just a few residues per segment of interest and at the same time sufficiently homologous to the original sequence to preserve the functionality of the original sequence and/or the ability to perform reverse transcription. The present invention includes amino acid sequences that are at least 60%, 65%, 70%, 72%, 74%, 76%, 78%, 80%, 90%, or 95% similar or identical to the original amino acid sequence. The degree of identity between two peptides is determined using computer algorithms and methods that are widely known to the persons skilled in the art. The identity between two amino acid sequences may be determined by using the BLASTP algorithm (BLAST Manual, Altschul, S., et al., NCBI NLM NIH Bethesda, Md. 20894, Altschul, S., et al., J. Mol. Biol. 215: 403-410 (1990)).

The polypeptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The polypeptides of the invention may include unnatural amino acids formed by post-translational modification or by introducing unnatural amino acids during translation. A variety of approaches are available for introducing unnatural amino acids during protein translation.

A polypeptide or protein of the invention may be conjugated with other molecules, such as proteins, to prepare fusion proteins. This may be accomplished, for example, by the synthesis of N-terminal or C-terminal fusion proteins provided that the resulting fusion protein retains the functionality of a reverse transcriptase.

A peptide or protein of the invention may be phosphorylated using conventional methods such as the method described in Reedijk et al. (The EMBO Journal 11(4):1365, 1992).

Cyclic derivatives of the polypeptides of the invention are also part of the present invention. Cyclization may allow the polypeptide to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

It may be desirable to produce a cyclic polypeptide which is more flexible than the cyclic polypeptides having peptide bond linkages as described above. A more flexible polypeptide may be prepared by introducing cysteines at the right and left position of the polypeptide and forming a disulfide bridge between the two cysteines. The two cysteines are arranged so as not to deform the beta-sheet and turn. The polypeptide is more flexible as a result of the length of the disulfide linkage and the smaller number of hydrogen bonds in the beta-sheet portion. The relative flexibility of a cyclic polypeptide can be determined by molecular dynamics simulations.

The invention also relates to polypeptides comprising a reverse transcriptase fused to, or integrated into, a target protein, and/or a targeting domain capable of directing the chimeric protein to a desired location. The chimeric proteins may also comprise additional amino acid sequences or domains. The chimeric proteins are recombinant in the sense that the various components are from different sources, and as such are not found together in nature (i.e., are heterologous).

In one embodiment, the targeting domain can be a membrane spanning domain, a membrane binding domain, or a sequence directing the protein to associate with for example vesicles or with the nucleus. In one embodiment, the targeting domain can target a peptide to a particular cell type or tissue. For example, the targeting domain can be a cell surface ligand or an antibody against cell surface antigens of a target tissue. A targeting domain may target the polypeptide of the invention to a cellular component.

A polypeptide of the invention may be synthesized by conventional techniques. For example, the polypeptides or chimeric proteins may be synthesized by chemical synthesis using solid phase peptide synthesis. These methods employ either solid or solution phase synthesis methods (see for example, J. M. Stewart, and J. D. Young, Solid Phase Peptide Synthesis, 2nd Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis). By way of example, a polypeptide of the invention may be synthesized using 9-fluorenyl methoxycarbonyl (Fmoc) solid phase chemistry with direct incorporation of phosphothreonine as the N-fluorenylmethoxy-carbonyl-O-benzyl-L-phosphothreonine derivative.

N-terminal or C-terminal fusion proteins comprising a polypeptide or chimeric protein of the invention conjugated with other molecules may be prepared by fusing, through recombinant techniques, the N-terminal or C-terminal of the polypeptide or chimeric protein, and the sequence of a selected protein or selectable marker with a desired biological function. The resultant fusion proteins comprise a reverse transcriptase fused to the selected protein or marker protein as described herein. Examples of proteins which may be used to prepare fusion proteins include immunoglobulins, glutathione-S-transferase (GST), hemagglutinin (HA), and truncated myc.

Polypeptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The polypeptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Polynucleotides

In one embodiment, the present invention provides a composition comprising an isolated nucleic acid encoding a reverse transcriptase. For example, in certain embodiments, the composition comprises a nucleic acid encoding a reverse transcriptase derived from E.r. maturase. In one embodiment, the composition comprises a nucleic acid encoding a reverse transcriptase, wherein the reverse transcriptase comprises E.r. maturase or variant thereof. In certain embodiments, the nucleic acid is DNA, RNA, mRNA, or cDNA.

In one embodiment, the nucleic acid encodes a reverse transcriptase comprising wildtype E.r. maturase, wherein the amino acid sequence of wildtype maturase is set forth in SEQ ID NO: 14.

In some embodiments, the nucleic acid encodes an E.r. maturase variant comprising at least one point mutation selected from the group R58X, K59X, K61X, K163X, K216X, R217X, K338X, K342X, and R353X relative to wildtype E.r. maturase, wherein X denotes any amino acid. In some embodiments, the nucleic acid encodes an E.r. maturase variant comprising at least one point mutation selected from the group R58A, K59A, K61A, K163A, K216A, R217A, K338A, K342A, and R353A relative to wildtype E.r. maturase.

In one embodiment, the nucleic acid encodes an E.r. maturase variant (referred to herein as E.r. maturase mut1; and denoted as SEQ ID NO: 15) comprising the point mutations of: R58A, K59A, K61A, and K163A, relative to wildtype E.r. maturase.

In one embodiment, the nucleic acid encodes an E.r. maturase variant (referred to herein as E.r. maturase mut2; and denoted as SEQ ID NO: 16) comprising the point mutations of: K216A and K217A, relative to wildtype E.r. maturase.

In one embodiment, the nucleic acid encodes an E.r. maturase variant (referred to herein as E.r. maturase mut1+mut2; and denoted as SEQ ID NO: 17) comprising the point mutations of: R58A, K59A, K61A, K163A, K216A, and R217A, relative to wildtype E.r. maturase.

In one embodiment, the nucleic acid encodes an E.r. maturase variant (referred to herein as E.r. maturase mut3; and denoted as SEQ ID NO: 18) comprising the point mutations of: K338A, K342A, and R353A relative to wildtype E.r. maturase.

In one embodiment, the nucleic acid encodes an E.r. maturase variant comprising one or more mutations in the α-loop, C-terminal DNA binding domain, and/or thumb domain. In one embodiment, the nucleic acid encodes an E.r. maturase variant engineered to have Lys-Glu pairs at positions that are proximal in 3-D space. In one embodiment, the nucleic acid encodes an E.r. maturase variant, wherein one or more fragments or domains of E.r. maturase is replaced by one or more fragments or domains from a maturase reverse transcriptase from a species other than *Eubacterium rectale*.

In certain embodiments, the composition increases the expression of a biologically functional fragment of E.r. maturase. For example, in one embodiment, the composition comprises an isolated nucleic acid sequence encoding a biologically functional fragment of E.r. maturase. As would be understood in the art, a biologically functional fragment is a portion or portions of a full length sequence that retain the biological function of the full length sequence. Thus, a biologically functional fragment of E.r. maturase comprises a peptide that retains the function of full length E.r. maturase.

Further, the invention encompasses an isolated nucleic acid encoding a peptide having substantial homology to a reverse transcriptase disclosed herein. In certain embodiments, the isolated nucleic acid sequence encodes a reverse transcriptase having at least 75%, 80%, 85%, 90%, 95%, 96%, 97%, 98%, or 99% sequence homology with an amino acid sequence selected from SEQ ID NO:14, SEQ ID NO:15, SEQ ID NO:16, SEQ ID NO:17, SEQ ID NO:18 and SEQ ID NO:19.

The isolated nucleic acid sequence encoding a reverse transcriptase can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The isolated nucleic acid may comprise any type of nucleic acid, including, but not limited to DNA and RNA. For example, in one embodiment, the composition comprises an isolated DNA molecule, including for example, an isolated cDNA molecule, encoding a reverse transcriptase. In one embodiment, the composition comprises an isolated RNA molecule encoding a reverse transcriptase.

In one aspect, the present invention provides a composition comprising an agent that improves RT activity of E.r. maturase or variants thereof. For example, in some embodiments, the composition comprises an agent that reduces non-specific binding of primers to the positively charged surface of E.r. maturase or variants thereof. In some embodiments, the agent that reduces non-specific binding of primers to the positively charged surface of E.r. maturase or variants thereof comprises a nucleic acid molecule, such as a single stranded or double stranded DNA or RNA molecule. For example, in one embodiment, the agent comprises an RNA molecule, such as a double stranded RNA or a single stranded RNA hairpin or stem-loop molecule. In some embodiments, the agent comprises a nucleic acid molecule derived from a group II intron, such as the E.r. group II intron. In one embodiment, the agent comprises D4A helix, a nucleic acid molecule derived from E.r. group II intron. In some embodiments, the agent comprises a variant derived from D4A, including, but not limited to, a fragment of D4A, a D4A mutant, or a nucleic acid molecule having substantial homology to D4A.

In one embodiment, the agent comprises a fragment of D4A that is able to bind to the surface of E.r. maturase or variant thereof. For example, in one embodiment the agent comprises a fragment of D4A comprising the apical loop of D4A. In one embodiment, the agent comprises a fragment of D4A comprising the apical loop of D4A and one or more nucleotides of the stem adjacent to the apical loop of D4A. For example, in one embodiment, the agent comprises a fragment of D4A comprising the nucleotide sequence of CGUAACCAAUCGG (SEQ ID NO:28). In one embodiment, the agent comprises a fragment of D4A comprising the nucleotide sequence of CCGUAACCAAUCGGG (SEQ ID NO:29). In one embodiment, the agent comprises a fragment of D4A comprising the nucleotide sequence of UGCCGUAACCAAUCGGGUAAAA (SEQ ID NO:30).

In one embodiment, the agent comprises a mutant D4A, including a mutant D4A having one or more mutations to improve its binding to the surface of E.r. maturase or variant thereof. In some embodiments, the agent comprises a mutant D4A that retains the ability to bind to E.r. maturase or variant thereof.

In one embodiment, the isolated nucleic acid comprises D4A, which can be used along with E.r maturase or variants thereof to reduce non-specific binding of primers to the surface of E.r. maturase or variants thereof. For example, in one embodiment, the isolated nucleic acid comprises D4A, which comprises a nucleotide sequence provided by SEQ ID NO:23 (FIG. 12A).

In some embodiments, the isolated nucleic acid molecule comprises a nucleotide sequence having at least 75%, 80%, 85%, 90%, 95%, 96%, 97%, 98%, or 99% sequence homology with the nucleotide sequence provided by SEQ ID NO:23.

In some embodiments, the isolated nucleic acid molecule comprises a fragment of D4A. For example, in some embodiments, the isolated nucleic acid molecule comprising 5 or more, 10 or more, 20 or more, 30 or more, 40 or more, 50 or more, 60 or more, 65 or more, 66 or more, 67 or more, 68 or more, or 69 or more nucleotides of SEQ ID NO:23.

In some embodiments, the composition comprises a nucleic acid molecule that encodes a nucleic acid molecule that improves RT activity, or reduces non-specific binding of primers to the positively charged surface of E.r. maturase or variants thereof. For example, in some embodiments, the composition comprises a nucleic acid molecule that encodes D4A, a D4A fragment, a D4A mutant, or a molecule having at least 75%, 80%, 85%, 90%, 95%, 96%, 97%, 98%, or 99% sequence homology to D4A.

The nucleic acid molecules of the present invention can be modified to improve stability in serum or in growth medium for cell cultures. Modifications can be added to enhance stability, functionality, and/or specificity. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may comprise at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; 0- and N-alkylated nucleotides, e.g., N6-methyl adenosine are suitable. The above modifications may be combined.

In some instances, the nucleic acid molecule comprises at least one of the following chemical modifications: 2'-H, 2'-O-methyl, or 2'-OH modification of one or more nucleotides. In certain embodiments, a nucleic acid molecule of the invention can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O-N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

In certain embodiments, the nucleic acid molecule of the invention may have one or more of the following properties:

Nucleic acid agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature. The art has referred to rare or unusual, but naturally occurring, RNAs as modified RNAs, see, e.g., Limbach et al. (Nucleic Acids Res., 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from those which occur in nature. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone.

Modifications of the nucleic acid of the invention may be present at one or more of, a phosphate group, a sugar group, backbone, N-terminus, C-terminus, or nucleobase.

Expression Systems

The present invention also includes a vector in which the isolated nucleic acid of the present invention is inserted. The art is replete with suitable vectors that are useful in the present invention.

In brief summary, the expression of natural or synthetic nucleic acids encoding a reverse transcriptase described herein is typically achieved by operably linking a nucleic acid encoding a reverse transcriptase to a promoter, and incorporating the construct into an expression vector. The vectors to be used are suitable for replication and, optionally, integration in host cells. Typical vectors contain transcription and translation terminators, initiation sequences, and promoters useful for regulation of the expression of the desired nucleic acid sequence.

The isolated nucleic acid of the invention can be cloned into many types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into cells. For example, retroviruses provide a convenient platform for gene delivery systems. A selected gene can be inserted into a vector and packaged in retroviral particles using techniques known in the art. The recombinant virus can then be isolated and delivered to cells. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for use, including a lack of pathogenicity, minimal immunogenicity, and the ability to transduce post-mitotic cells in a stable and efficient manner. Expression of a particular gene contained within an AAV vector can be specifically targeted to one or more types of cells by choosing the appropriate combination of AAV serotype, promoter, and delivery method.

In certain embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulate expression of the gene contained therein. Typically, enhancers are bound with protein factors to enhance the transcription of a gene. An enhancer may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of E.r. maturase or a E.r. maturase-derived peptide, the expression vector to be introduced into a cell can also comprise either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution comprising a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma-Aldrich®; dicetyl phosphate ("DCP") can be obtained from K & K Laboratories Inc. (Plainview, N.Y.); cholesterol ("Choi") can be obtained from Calbiochem®-Behring; dimyristyl phosphatidylglycerol ("DMPG") and other lipids may be obtained from Avanti® Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, the present invention provides a delivery vehicle comprising a reverse transcriptase, or a nucleic acid molecule encoding a reverse transcriptase. Exemplary delivery vehicles include, but are not limited to, microspheres, microparticles, nanoparticles, polymerosomes, liposomes, and micelles. For example, in certain embodiments, the delivery vehicle is loaded with a reverse transcriptase, or a nucleic acid molecule encoding a reverse transcriptase. In certain embodiments, the delivery vehicle provides for controlled release, delayed release, or continual release of its loaded cargo. In certain embodiments, the delivery vehicle comprises a targeting moiety that targets the delivery vehicle to a particular location.

In one embodiment, the present invention provides a full-length cDNA derived from a full-length RNA, produced by a reverse transcriptase described herein. In one embodiment, the RNA has significant secondary or tertiary structure, and/or is long (greater than or equal to 5,000 bases in length). For example, it is described herein that E.r. maturase and E.r. maturase-derived peptides described herein are highly processive reverse transcriptases. In one embodiment, the RNA reverse transcribed into DNA is at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, or at least about 10000 bases in length. In one embodiment, the DNA so reverse transcribed is at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, or at least about 10000 bases in length.

Formulations

The present invention also provides formulated compositions comprising one or more of the compositions described herein. Formulations may be employed in admixtures with conventional excipients, i.e., pharmaceutically acceptable organic or inorganic carrier substances suitable for storage and use of a reverse transcriptase. The formulated compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., other components of the reverse transcription reaction or other components suitable for storage of the E.r. maturase or variants thereof.

In one embodiment, the composition formulation is optimized to modify the protein's purity, stability, processivity, turnover, error rate, or other properties. In another embodiment, the protein itself is optimized to modify the protein's purity, stability, processivity, turnover, error rate, or other properties. Assays for measuring properties of the compositions of the invention are described elsewhere herein.

In one embodiment, the composition formulation is optimized to improve thermal stability of E.r. maturase or a variant thereof. In one embodiment, the type and/or amount of salt, the overall ionic strength of the solution, water activity, crowding agents, the buffering molecule types and buffering capacity, the pH, the presence, identity and amount of detergents, or other carriers or stabilizing ingredients, are optimized to improve the thermal stability of E.r. maturase or a variant thereof. In one embodiment, the enzyme can thermocycle, wherein the reverse transcription reaction may be repeated using the same molecule of E.r. maturase or a variant thereof.

As used herein, "additional ingredients" include, but are not limited to, one or more of the following: excipients; surface active agents; crowding agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents;

suspending agents; dispersing or wetting agents; emulsifying agents, demulcents; buffers; salts; thickening agents; fillers; emulsifying agents; antioxidants; antibiotics; antifungal agents; stabilizing agents; and polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group benzyl alcohol, sorbic acid, parabens, imidurea and combinations thereof. One preservative is a combination of about 0.5% to 2.0% benzyl alcohol and 0.05% to 0.5% sorbic acid.

In one embodiment, the composition includes an antioxidant and/or a chelating agent that inhibits the degradation of one or more components of the composition. Exemplary antioxidants are BHT, BHA, alpha-tocopherol and ascorbic acid in the range of about 0.01% to 0.3%, or BHT in the range of 0.03% to 0.1% by weight by total weight of the composition. In one embodiment, the chelating agent is present in an amount of from 0.01% to 0.5% by weight by total weight of the composition. Chelating agents include edetate salts (e.g. disodium edetate) and citric acid in the weight range of about 0.01% to 0.20%, or in the range of 0.02% to 0.10% by weight by total weight of the composition. The chelating agent is useful for chelating metal ions in the composition that may be detrimental to the shelf life of the formulation. While BHT and disodium edetate are exemplary antioxidant and chelating agents, respectively, other suitable and equivalent antioxidants and chelating agents may be substituted therefore as would be known to those skilled in the art.

Liquid suspensions may be prepared using conventional methods to achieve suspension of the composition of the invention in an aqueous or oily vehicle. Aqueous vehicles include, for example, water, and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para hydroxybenzoates, ascorbic acid, and sorbic acid.

The invention further includes reaction solutions for reverse transcribing nucleic acid molecules, as well as reverse transcription methods employing such reaction solutions and product nucleic acid molecules produced using such methods. In many instances, reaction solutions of the invention will contain one or more of the following components: (1) one or more buffering agent (e.g., sodium phosphate, sodium acetate, 2-(N-moropholino)-ethanesulfonic acid (MES), tris-(hydroxymethyl)aminomethane (Tris), 3-(cyclohexylamino)-2-hydroxy-1-propanesulfonic acid (CAPS), citrate, N-2-hydroxyethylpiperazine-N'-2-ethanesulfonic acid (HEPES), acetate, 3-(N-morpholino)prpoanesulfonic acid (MOPS), N-tris(hydroxymethyl)methyl-3-aminopropanesulfonio acid (TAPS), etc.), (2) one or more monovalent cationic salt (e.g., NaCl, KCl, etc.), (3) one or more divalent cationic salt (e.g., $MnCl_2$, $MgCl_2$, $MgSO_4$, $CaCl_2$, etc.), (4) one or more reducing agent (e.g., dithiothreitol, 3-mercaptoethanol, etc.), (5) one or more ioninc or non-ionic detergent (e.g., TRITON X-100™, NONIDET P40™ sodium dodecyl sulphate, etc.), (6) one or more stabilizing agents (e.g., trehalose, betaine, BSA, glycerol) (7) one or more DNA polymerase inhibitor (e.g., Actinomycin D, etc.), (8) nucleotides (e.g., dNTPs, such as dGTP, dATP, dCTP, dTTP, etc.), (9) RNA to be reverse transcribed and/or amplified, (10) one or more RNase inhibitor (e.g., RNASEOUT™, Invitrogen Corporation, Carlsbad, Calif., etc.), (11) a reverse transcriptase (e.g., a reverse transcriptase of the invention), and/or (12) one or more diluent (e.g., water). Other components and/or constituents (e.g., primers, DNA polymerases, etc.) may also be present in reaction solutions.

In some embodiments, the invention includes an optimized reaction buffer that enhances the RT activity of E.r. maturase. In one embodiment, the optimized reaction buffer comprises Tris at a concentration of about 10 mM to about 100 mM; KCl at a concentration of about 100 mM to about 500 mM, $MgCl_2$ at a concentration of about 0.5 mM to about 5 mM, and DTT at a concentration of about 1 mM to about 10 mM, and wherein the reaction buffer has a pH of about 8 to 8.5. In one embodiment, the optimized reaction buffer comprises about 50 mM Tris, about 200 mM KCl, about 2 mM $MgCl_2$, about 5 mM DTT; and has a pH of about 8.3.

In one embodiment, the optimized reaction buffer further comprises a protein stabilizing agent. Exemplary protein stabilizing agents include, but are not limited to, osmolytic stabilizers such as glycerol, erythritol, arabitol, sorbitol, mannitol, xylitol, mannisdomannitol, glucosylglycerol, glucose, fructose, sucrose, trehalose, isofluorosid, dextrans, levans, and polyethylene glycol; amino acids and derivatives thereof such as glycine, alanine, proline, taurine, betaine, octopine, glutamate, sarcosine, γ-aminobutyric acid, trimethylamine, N-oxide (TMAO); ionic stabilizers such as citrate, sulfates, acetate, phosphates, and quaternary amines; and proteins such as bovine serum albumin (BSA).

In one embodiment, the optimized reaction buffer comprises trehalose at a concentration of about 0.1 M to about 1 M. In one embodiment, the optimized reaction buffer comprises betaine at a concentration of about 0.1 M to about 10 M. In one embodiment, the optimized reaction buffer comprises BSA at a concentration of about 0.5 mg/mL to about 2 mg/mL. In one embodiment, the optimized reaction buffer comprises glycerol at a concentration of about 1% to about 50%.

The concentration of the buffering agent in the reaction solutions of the invention will vary with the particular buffering agent used. Typically, the working concentration (i.e., the concentration in the reaction mixture) of the buffering agent will be from about 5 mM to about 500 mM (e.g., about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, from about 5 mM to about 500 mM, from about 10 mM to about 500 mM, from about 20 mM to about 500 mM, from about 25 mM to about 500 mM, from about 30 mM to about 500 mM, from about 40 mM to about 500 mM, from about 50 mM to about 500 mM, from about 75 mM to about 500 mM, from about 100 mM to about 500 mM, from about 25 mM to about 50 mM, from about 25 mM to about 75 mM, from about 25 mM to about 100 mM, from about 25 mM to about 200 mM, from about 25 mM to about 300 mM, etc.). When Tris (e.g., Tris-HCl) is used, the Tris working concentration will typically be from about 5 mM to about 100 mM, from about 5 mM to about 75 mM, from about 10 mM to about 75 mM, from about 10 mM to about 60 mM, from about 10 mM to about 50 mM, from about 25 mM to about 50 mM, etc.

The final pH of solutions of the invention will generally be set and maintained by buffering agents present in reaction solutions of the invention. The pH of reaction solutions of the invention, and hence reaction mixtures of the invention, will vary with the particular use and the buffering agent present but will often be from about pH 5.5 to about pH 9.0 (e.g., about pH 6.0, about pH 6.5, about pH 7.0, about pH 7.1, about pH 7.2, about pH 7.3, about pH 7.4, about pH 7.5, about pH 7.6, about pH 7.7, about pH 7.8, about pH 7.9, about pH 8.0, about pH 8.1, about pH 8.2, about pH 8.3, about pH 8.4, about pH 8.5, about pH 8.6, about pH 8.7, about pH 8.8, about pH 8.9, about pH 9.0, from about pH 6.0 to about pH 8.5, from about pH 6.5 to about pH 8.5, from about pH 7.0 to about pH 8.5, from about pH 7.5 to about pH 8.5, from about pH 6.0 to about pH 8.0, from about pH 6.0 to about pH 7.7, from about pH 6.0 to about pH 7.5, from about pH 6.0 to about pH 7.0, from about pH 7.2 to about pH 7.7, from about pH 7.3 to about pH 7.7, from about pH 7.4 to about pH 7.6, from about pH 7.0 to about pH 7.4, from about pH 7.6 to about pH 8.0, from about pH 7.6 to about pH 8.5, from about pH 7.7 to about pH 8.5, from about pH 7.9 to about pH 8.5, from about pH 8.0 to about pH 8.5, from about pH 8.2 to about pH 8.5, from about pH 8.3 to about pH 8.5, from about pH 8.4 to about pH 8.5, from about pH 8.4 to about pH 9.0, from about pH 8.5 to about pH 9.0, etc.)

As indicated, one or more monovalent cationic salts (e.g., NaCl, KCl, etc.) may be included in reaction solutions of the invention. In many instances, salts used in reaction solutions of the invention will dissociate in solution to generate at least one species which is monovalent (e.g., $Na^+$, $K^+$, etc.) When included in reaction solutions of the invention, salts will often be present either individually or in a combined concentration of from about 0.5 mM to about 500 mM (e.g., about 1 mM, about 2 mM, about 3 mM, about 5 mM, about 10 mM, about 12 mM, about 15 mM, about 17 mM, about 20 mM, about 22 mM, about 23 mM, about 24 mM, about 25 mM, about 27 mM, about 30 mM, about 35 mM, about 40 mM, about 45 mM, about 50 mM, about 55 mM, about 60 mM, about 64 mM, about 65 mM, about 70 mM, about 75 mM, about 80 mM, about 85 mM, about 90 mM, about 95 mM, about 100 mM, about 120 mM, about 140 mM, about 150 mM, about 175 mM, about 200 mM, about 225 mM, about 250 mM, about 275 mM, about 300 mM, about 325 mM, about 350 mM, about 375 mM, about 400 mM, from about 1 mM to about 500 mM, from about 5 mM to about 500 mM, from about 10 mM to about 500 mM, from about 20 mM to about 500 mM, from about 30 mM to about 500 mM, from about 40 mM to about 500 mM, from about 50 mM to about 500 mM, from about 60 mM to about 500 mM, from about 65 mM to about 500 mM, from about 75 mM to about 500 mM, from about 85 mM to about 500 mM, from about 90 mM to about 500 mM, from about 100 mM to about 500 mM, from about 125 mM to about 500 mM, from about 150 mM to about 500 mM, from about 200 mM to about 500 mM, from about 10 mM to about 100 mM, from about 10 mM to about 75 mM, from about 10 mM to about 50 mM, from about 20 mM to about 200 mM, from about 20 mM to about 150 mM, from about 20 mM to about 125 mM, from about 20 mM to about 100 mM, from about 20 mM to about 80 mM, from about 20 mM to about 75 mM, from about 20 mM to about 60 mM, from about 20 mM to about 50 mM, from about 30 mM to about 500 mM, from about 30 mM to about 100 mM, from about 30 mM to about 70 mM, from about 30 mM to about 50 mM, etc.).

As indicated, one or more divalent cationic salts (e.g., $MnCl_2$, $MgCl_2$, $MgSO_4$, $CaCl_2$, etc.) may be included in reaction solutions of the invention. In many instances, salts used in reaction solutions of the invention will dissociate in solution to generate at least one species which is monovalent (e.g., $Mg^{++}$, $Mn^{++}$, $Ca^{++}$, etc.) When included in reaction solutions of the invention, salts will often be present either individually or in a combined concentration of from about 0.5 mM to about 500 mM (e.g., about 1 mM, about 2 mM, about 3 mM, about 4 mM, about 5 mM, about 6 mM, about 7 mM, about 8 mM, about 9 mM, about 10 mM, about 12 mM, about 15 mM, about 17 mM, about 20 mM, about 22 mM, about 23 mM, about 24 mM, about 25 mM, about 27 mM, about 30 mM, about 35 mM, about 40 mM, about 45 mM, about 50 mM, about 55 mM, about 60 mM, about 64 mM, about 65 mM, about 70 mM, about 75 mM, about 80 mM, about 85 mM, about 90 mM, about 95 mM, about 100 mM, about 120 mM, about 140 mM, about 150 mM, about 175 mM, about 200 mM, about 225 mM, about 250 mM, about 275 mM, about 300 mM, about 325 mM, about 350 mM, about 375 mM, about 400 mM, from about 1 mM to about 500 mM, from about 5 mM to about 500 mM, from about 10 mM to about 500 mM, from about 20 mM to about 500 mM, from about 30 mM to about 500 mM, from about 40 mM to about 500 mM, from about 50 mM to about 500 mM, from about 60 mM to about 500 mM, from about 65 mM to about 500 mM, from about 75 mM to about 500 mM, from about 85 mM to about 500 mM, from about 90 mM to about 500 mM, from about 100 mM to about 500 mM, from about 125 mM to about 500 mM, from about 150 mM to about 500 mM, from about 200 mM to about 500 mM, from about 10 mM to about 100 mM, from about 10 mM to about 75 mM, from about 10 mM to about 50 mM, from about 20 mM to about 200 mM, from about 20 mM to about 150 mM, from about 20 mM to about 125 mM, from about 20 mM to about 100 mM, from about 20 mM to about 80 mM, from about 20 mM to about 75 mM, from about 20 mM to about 60 mM, from about 20 mM to about 50 mM, from about 30 mM to about 500 mM, from about 30 mM to about 100 mM, from about 30 mM to about 70 mM, from about 30 mM to about 50 mM, etc.).

When included in reaction solutions of the invention, reducing agents (e.g., dithiothreitol, β-mercaptoethanol, etc.) will often be present either individually or in a combined concentration of from about 0.1 mM to about 50 mM (e.g., about 0.2 mM, about 0.3 mM, about 0.5 mM, about 0.7 mM, about 0.9 mM, about 1 mM, about 2 mM, about 3 mM, about 4 mM, about 5 mM, about 6 mM, about 10 mM, about 12 mM, about 15 mM, about 17 mM, about 20 mM, about 22 mM, about 23 mM, about 24 mM, about 25 mM, about 27 mM, about 30 mM, about 35 mM, about 40 mM, about 45 mM, about 50 mM, from about 0.1 mM to about 50 mM, from about 0.5 mM to about 50 mM, from about 1 mM to about 50 mM, from about 2 mM to about 50 mM, from about 3 mM to about 50 mM, from about 0.5 mM to about 20 mM, from about 0.5 mM to about 10 mM, from about 0.5 mM to about 5 mM, from about 0.5 mM to about 2.5 mM, from about 1 mM to about 20 mM, from about 1 mM to about 10 mM, from about 1 mM to about 5 mM, from about 1 mM to about 3.4 mM, from about 0.5 mM to about 3.0 mM, from about 1 mM to about 3.0 mM, from about 1.5 mM to about 3.0 mM, from about 2 mM to about 3.0 mM, from about 0.5 mM to about 2.5 mM, from about 1 mM to about 2.5 mM, from about 1.5 mM to about 2.5 mM, from about 2 mM to about 3.0 mM, from about 2.5 mM to about 3.0 mM, from about 0.5 mM to about 2 mM, from about 0.5 mM to about 1.5 mM, from about 0.5 mM to about 1.1 mM, from about 5.0 mM to about 10 mM, from about 5.0 mM to about 15 mM, from about 5.0 mM to about 20 mM, from about 10 mM to about 15 mM, from about 10 mM to about 20 mM, etc.).

Reaction solutions of the invention may also contain one or more ionic or non-ionic detergent (e.g., TRITON X-100™, NONIDET P40™, sodium dodecyl sulfate, etc.). When included in reaction solutions of the invention, detergents will often be present either individually or in a combined concentration of from about 0.01% to about 5.0% (e.g., about 0.01%, about 0.02%, about 0.03%, about 0.04%, about 0.05%, about 0.06%, about 0.07%, about 0.08%, about 0.09%, about 0.1%, about 0.15%, about 0.2%, about 0.3%, about 0.5%, about 0.7%, about 0.9%, about 1%, about 2%, about 3%, about 4%, about 5%, from about 0.01% to about 5.0%, from about 0.01% to about 4.0%, from about 0.01% to about 3.0%, from about 0.01% to about 2.0%, from about 0.01% to about 1.0%, from about 0.05% to about 5.0%, from about 0.05% to about 3.0%, from about 0.05% to about 2.0%, from about 0.05% to about 1.0%, from about 0.1% to about 5.0%, from about 0.1% to about 4.0%, from about 0.1% to about 3.0%, from about 0.1% to about 2.0%, from about 0.1% to about 1.0%, from about 0.1% to about 0.5%, etc.). For example, reaction solutions of the invention may contain TRITON X-100™ at a concentration of from about 0.01% to about 2.0%, from about 0.03% to about 1.0%, from about 0.04% to about 1.0%, from about 0.05% to about 0.5%, from about 0.04% to about 0.6%, from about 0.04% to about 0.3%, etc.

Reaction solutions of the invention may also contain one or more stabilizing agents (e.g., trehalose, betaine, BSA, glycerol). In some embodiments, when included in reaction solutions of the invention, stabilizing agents are present either individually or in a combined concentration from 0.01 M to about 50 M (e.g., about 0.05M, about 0.1 M, 0.2 M, about 0.3 M, about 0.5 M, about 0.6 M, about 0.7 M, about 0.9 M, about 1 M, about 2 M, about 3 M, about 4 M, about 5 M, about 6 M, about 10 M, about 12 M, about 15 M, about 17 M, about 20 M, about 22 M, about 23 M, about 24 M, about 25 M, about 27 M, about 30 M, about 35 M, about 40 M, about 45 M, about 50 M, from about 0.1 M to about 1 M, from about 0.5 M to about 5 M, from about 0.2 M to about 2 M, from about 0.3 M to about 3 M, from about 0.4 M to about 4 M, from about 0.5 M to about 5 M, from about 0.2 M to about 0.8 M, from about 0.5 M to about 1 M, from about 0.05 M to about 1 M, from about 0.05 M to about 10 M, from about 0.05 M to about 20M, etc.). In some embodiments, when included in reaction solutions of the invention, such stabilizing agents are present either individually or in a combined concentration of from about 0.01 mg/ml to about 100 mg/ml (e.g., about 0.01 mg/ml, about 0.02 mg/ml, about 0.03 mg/ml, about 0.04 mg/ml, about 0.05 mg/ml, about 0.06 mg/ml, about 0.07 mg/ml, about 0.08 mg/ml, about 0.09 mg/ml, about 0.1 mg/ml, about 0.11 mg/ml, about 0.12 mg/ml, about 0.15 mg/ml, about 0.17 mg/ml, about 0.2 mg/ml, about 0.25 mg/ml, about 0.35 mg/ml, about 0.5 mg/ml, about 0.75 mg/ml, about 1.0 mg/ml, about 1.5 mg/ml, about 2.0 mg/ml, about 2.5 mg/ml, about 3.0 mg/ml, about 3.5 mg/ml, about 4.0 mg/ml, about 5.0 mg/ml, about 6.0 mg/ml, about 7.0 mg/ml, about 8.0 mg/ml, about 9.0 mg/ml, about 10.0 mg/ml, from about 0.05 mg/ml to about 3.0 mg/ml, from about 0.1 mg/ml to about 5.0 mg/ml, from about 0.2 mg/ml to about 2.0 mg/ml, etc.). In some embodiments, when included in reaction solutions of the invention, such stabilizing agents are be present either individually or in a combined concentration of from about 0.1% to about 50% (e.g., about 0.1%, about 0.2%, about 0.3%, about 0.4%, about 0.5%, about 0.6%, about 0.7%, about 0.8%, about 0.9%, about 1.0%, about 1.5%, about 2.0%, about 3.0%, about 5.0%, about 7.0%, about 9.0%, about 10%, about 11%, about 12%, about 13%, about 14%, about 15%, about 20%, about 22%, about 25%, about 27%, about 30%, about 35%, about 40%, about 45%, about 50%, from about 0.1% to about 50%, from about 0.1% to about 40%, from about 0.1% to about 30%, from about 0.0% to about 20%, from about 0.1% to about 10%, etc.

Reaction solutions of the invention may also contain one or more DNA polymerase inhibitor (e.g., Actinomycin D, etc.). When included in reaction solutions of the invention, such inhibitors will often be present either individually or in a combined concentration of from about 0.1 µg/ml to about 100 µg/ml (e.g., about 0.1 µg/ml, about 0.2 µg/ml, about 0.3 µg/ml, about 0.4 µg/ml, about 0.5 µg/ml, about 0.6 µg/ml, about 0.7 µg/ml, about 0.8 µg/ml, about 0.9 µg/ml, about 1.0 µg/ml, about 1.1 µg/ml, about 1.3 µg/ml, about 1.5 µg/ml, about 1.7 µg/ml, about 2.0 µg/ml, about 2.5 µg/ml, about 3.5 µg/ml, about 5.0 µg/ml, about 7.5 µg/ml, about 10 µg/ml, about 15 µg/ml, about 20 µg/ml, about 25 µg/ml, about 30 µg/ml, about 35 µg/ml, about 40 µg/ml, about 50 µg/ml, about 60 µg/ml, about 70 µg/ml, about 80 µg/ml, about 90 µg/ml, about 100 µg/ml, from about 0.5 µg/ml to about 30 µg/ml, from about 0.75 µg/ml to about 30 µg/ml, from about 1.0 µg/ml to about 30 µg/ml, from about 2.0 µg/ml to about 30 µg/ml, from about 3.0 µg/ml to about 30 µg/ml, from about 4.0 µg/ml to about 30 µg/ml, from about 5.0 µg/ml to about 30 µg/ml, from about 7.5 µg/ml to about 30 µg/ml, from about 10 µg/ml to about 30 µg/ml, from about 15 µg/ml to about 30 µg/ml, from about 0.5 µg/ml to about 20 µg/ml, from about 0.5 µg/ml to about 10 µg/ml, from about 0.5 µg/ml to about 5 µg/ml, from about 0.5 µg/ml to about 2 µg/ml, from about 0.5 µg/ml to about 1 µg/ml, from about 1 µg/ml to about 10 µg/ml, from about 1 µg/ml to about 5 µg/ml, from about 1 µg/ml to about 2 µg/ml, from about 1 µg/ml to about 100 µg/ml, from about 10 µg/ml to about 100 µg/ml, from about 20 µg/ml to about 100 µg/ml, from about 40 µg/ml to about 100 µg/ml, from about 30 µg/ml to about 80 µg/ml, from about 30 µg/ml to about 70 µg/ml, from about 40 µg/ml to about 60 µg/ml, from about 40 µg/ml to about 70 µg/ml, from about 40 µg/ml to about 80 µg/ml, etc.).

Reaction solutions the invention may also contain one or more additional additives that improve RT activity, including agents that improve primer utilization efficiency and improve product yield. In one embodiment, the reaction solution comprises an agent that reduces non-specific binding of primers to the E.r. maturase surface. As described elsewhere herein, the agent may comprise any protein, nucleic acid molecule, or small molecule that prevents or reduces non-specific binding. In certain embodiments, the agent comprises D4A or variant thereof. Variants of D4A may comprise a D4A fragment, a D4A mutant, or a molecule having substantial homology to D4A, as described elsewhere herein.

When included in reaction solutions of the invention, D4A, or variant thereof, may be present at ratio of D4A (or variant thereof) concentration to E.r. maturase concentration from about 0.1:1 to about 100:1. For example, in some embodiments, D4A, or variant thereof, may be present at ratio of D4A (or variant thereof) concentration to E.r. maturase concentration of about 0.1:1, 0.2:1, 0.3:1, 0.4:1, 0.5:1, 0.6:1, 0.7:1, 0.8:1, 0.9:1, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, 55:1, 60:1, 65:1, 70:1, 75:1, 80:1, 85:1, 90:1, 95:1, or 100:1.

In many instances, nucleotides (e.g., dNTPs, such as dGTP, dATP, dCTP, dTTP, etc.) will be present in reaction mixtures of the invention. Typically, individual nucleotides will be present in concentrations of from about 0.05 mM to about 50 mM (e.g., about 0.07 mM, about 0.1 mM, about 0.15 mM, about 0.18 mM, about 0.2 mM, about 0.3 mM, about 0.5 mM, about 0.7 mM, about 0.9 mM, about 1 mM, about 2 mM, about 3 mM, about 4 mM, about 5 mM, about 6 mM, about 10 mM, about 12 mM, about 15 mM, about 17 mM, about 20 mM, about 22 mM, about 23 mM, about 24 mM, about 25 mM, about 27 mM, about 30 mM, about 35 mM, about 40 mM, about 45 mM, about 50 mM, from about 0.1 mM to about 50 mM, from about 0.5 mM to about 50 mM, from about 1 mM to about 50 mM, from about 2 mM to about 50 mM, from about 3 mM to about 50 mM, from about 0.5 mM to about 20 mM, from about 0.5 mM to about 10 mM, from about 0.5 mM to about 5 mM, from about 0.5 mM to about 2.5 mM, from about 1 mM to about 20 mM, from about 1 mM to about 10 mM, from about 1 mM to about 5 mM, from about 1 mM to about 3.4 mM, from about 0.5 mM to about 3.0 mM, from about 1 mM to about 3.0 mM, from about 1.5 mM to about 3.0 mM, from about 2 mM to about 3.0 mM, from about 0.5 mM to about 2.5 mM, from about 1 mM to about 2.5 mM, from about 1.5 mM to about 2.5 mM, from about 2 mM to about 3.0 mM, from about 2.5 mM to about 3.0 mM, from about 0.5 mM to about 2 mM, from about 0.5 mM to about 1.5 mM, from about 0.5 mM to about 1.1 mM, from about 5.0 mM to about 10 mM, from about 5.0 mM to about 15 mM, from about 5.0 mM to about 20 mM, from about 10 mM to about 15 mM, from about 10 mM to about 20 mM, etc.). The combined nucleotide concentration, when more than one nucleotides is present, can be determined by adding the concentrations of the individual nucleotides together. When more than one nucleotide is present in reaction solutions of the invention, the individual nucleotides may not be present in equimolar amounts. Thus, a reaction solution may contain, for example, 1 mM dGTP, 1 mM dATP, 0.5 mM dCTP, and 1 mM dTTP.

RNA will typically be present in reaction solutions of the invention. In most instances, RNA will be added to the reaction solution shortly prior to reverse transcription. Thus, reaction solutions may be provided without RNA. This will typically be the case when reaction solutions are provided in kits. RNA, when present in reaction solutions will often be present in a concentration of 1 picogram to 100 μg/20 μl reaction mixture (e.g., about 1 picogram/20 μl, about 10 picograms/20 μl, about 50 picograms/20 μl, about 100 picograms/20 μl, about 200 picograms/20 μl, about 10 picograms/20 about 500 picograms/20 μl, about 800 picograms/20 μl, about 1.0 nanogram/20 μl, about 5.0 nanograms/20 μl, about 10 nanograms/20 μl, about 25 nanograms/20 μl, about 50 nanograms/20 μl, about 75 nanograms/20 μl, about 100 nanograms/20 μl, about 150 nanograms/20 μl, about 250 nanograms/20 μl, about 400 nanograms/20 μl, about 500 nanograms/20 μl, about 750 nanograms/20 μl, about 1.0 μg/20 about 5.0 μg/20 about 10 μg/20 μl, about 20 μg/20 μl, about 30 μg/20 about 40 μg/20 about 50 μg/20 μl, about 70 μg/20 μl, about 85 μg/20 μl, about 100 μg/20 μl, from about 10 picograms/20 μl to about 100 μg/20 μl, from about 10 picograms/20 μl to about 100 μg/20 μl, from about 100 picograms/20 μl to about 100 μg/20 μl from about 1.0 nanograms/20 μl to about 100 μg/20 μl from about 100 nanograms/20 μl to about 100 μg/20 μl, from about 10 picograms/20 μl to about 10 μg/20 μl, from about 10 picograms/20 μl to about 5 μg/20 μl, from about 100 nanograms/20 μl to about 5 μg/20 μl, from about 1 μg/20 μl to about 10 μg/20 μl, from about 1 μg/20 μl to about 5 μg/20 μl, from about 100 nanograms/20 μl to about 1 μg/20 μl, from about 500 nanograms/20 μl to about 5 μg/20 μl, etc.). As one skilled in the art would recognize, different reverse transcription reactions may be performed in volumes other than 20 μl. In such instances, the total amount of RNA present will vary with the volume used. Thus, the above amounts are provided as examples of the amount of RNA/20 μl of reaction solution.

Reverse transcriptases (e.g., reverse transcriptases of the invention) may also be present in reaction solutions. When present, reverse transcriptases, will often be present in a concentration which results in about 0.01 to about 1,000 units of reverse transcriptase activity/μl (e.g., about 0.01 unit/μl, about 0.05 unit/μl, about 0.1 unit/μl, about 0.2 unit/μl, about 0.3 unit/μl, about 0.4 unit/μl, about 0.5 unit/μl, about 0.7 unit/μl, about 1.0 unit/μl, about 1.5 unit/μl, about 2.0 unit/μl, about 2.5 unit/μl, about 5.0 unit/μl, about 7.5 unit/μl, about 10 unit/μl, about 20 unit/μl, about 25 unit/μl, about 50 unit/μl, about 100 unit/μl, about 150 unit/μl, about 200 unit/μl, about 250 unit/μl, about 350 unit/μl, about 500 unit/μl, about 750 unit/μl, about 1,000 unit/μl, from about 0.1 unit/μl to about 1,000 unit/μl, from about 0.2 unit/μl to about 1,000 unit/μl, from about 1.0 unit/μl to about 1,000 unit/μl, from about 5.0 unit/μl to about 1,000 unit/μl, from about 10 unit/μl to about 1,000 unit/μl, from about 20 unit/μl to about 1,000 unit/μl, from about 50 unit/μl to about 1,000 unit/μl, from about 100 unit/μl to about 1,000 unit/μl, from about 200 unit/μl to about 1,000 unit/μl, from about 400 unit/μl to about 1,000 unit/μl, from about 500 unit/μl to about 1,000 unit/μl, from about 0.1 unit/μl to about 300 unit/μl, from about 0.1 unit/μl to about 200 unit/μl, from about 0.1 unit/μl to about 100 unit/μl, from about 0.1 unit/μl to about 50 unit/μl, from about 0.1 unit/μl to about 10 unit/μl, from about 0.1 unit/μl to about 5.0 unit/μl, from about 0.1 unit/μl to about 1.0 unit/μl, from about 0.2 unit/μl to about 0.5 unit/μl, etc. In certain embodiments, the reaction solution comprises a lower concentration of the reverse transcriptase described herein, as compared to what would be necessary to produce equivalent product from other reverse transcriptases.

Reaction solutions of the invention may be prepared as concentrated solutions (e.g., 5× solutions) which are diluted to a working concentration for final use. With respect to a 5× reaction solution, a 5:1 dilution is required to bring such a 5× solution to a working concentration. Reaction solutions of the invention may be prepared, for examples, as a 2×, a 3×, a 4×, a 5×, a 6×, a 7×, a 8×, a 9×, a 10×, etc. solutions. One major limitation on the fold concentration of such solutions is that, when compounds reach particular concentrations in solution, precipitation occurs. Thus, concentrated reaction solutions will generally be prepared such that the concentrations of the various components are low enough so that precipitation of buffer components will not occur. As one skilled in the art would recognize, the upper limit of concentration which is feasible for each solution will vary with the particular solution and the components present.

In many instances, reaction solutions of the invention will be provided in sterile form. Sterilization may be performed on the individual components of reaction solutions prior to mixing or on reaction solutions after they are prepared. Sterilization of such solutions may be performed by any suitable means including autoclaving or ultrafiltration.

Methods

In various embodiments, the present invention includes methods of engineering variants of E.r. maturase. In some embodiments, the variants have at least one enhanced property relative to unmodified E.r. maturase. In some embodiments, the variants are engineered by introducing one or more mutations in E.r. maturase, such that the engineered variant is improved relative to unmodified E.r. maturase with regard to the protein's purity, stability, processivity, turnover, error rate, or other properties.

In some embodiments, the method comprises modifying the reaction solution conditions relative to unmodified solution conditions to create an improved composition comprising E.r. maturase or a variant thereof, with regard to the protein's purity, stability, processivity, turnover, error rate, or other properties.

In various embodiments, the present invention includes methods of using a reverse transcriptase for a reverse transcription reaction. In one embodiment, the method comprises the use of an E.r. maturase, or a variant thereof; or a nucleic acid encoding E.r. maturase, or a variant thereof in a reverse transcription reaction. For example, in one embodiment, the method comprises contacting a reverse transcriptase, comprising an E.r. maturase or variant thereof, to an RNA template under suitable conditions to produce a transcribed DNA molecule from the RNA template.

In various embodiments, the present invention includes methods of performing a reverse transcription reaction using E.r. maturase, or a variant thereof, or a nucleic acid encoding E.r. maturase or a variant thereof; in combination with an agent that reduces non-specific binding of primers to the surface of E.r. maturase or variant thereof. For example, in some embodiments, the method comprises using E.r. maturase, or a variant thereof, or a nucleic acid encoding E.r. maturase or a variant thereof; in combination with any protein, nucleic acid molecule or small molecule that reduces non-specific binding. In some embodiments, the method comprises using E.r. maturase, or a variant thereof, or a nucleic acid encoding E.r. maturase or a variant thereof; in combination with a nucleic acid molecule, such as a double stranded or single stranded DNA or RNA molecule that reduces non-specific binding. In some embodiments, the method comprises using E.r. maturase, or a variant thereof, or a nucleic acid encoding E.r. maturase or a variant thereof; in combination with a RNA hairpin or stem-loop molecule that reduces non-specific binding. In some embodiments, the method comprises using E.r. maturase, or a variant thereof, or a nucleic acid encoding E.r. maturase or a variant thereof; in combination with a nucleic acid molecule derived from a group II intron that reduces non-specific binding. In some embodiments, the method comprises using E.r. maturase, or a variant thereof, or a nucleic acid encoding E.r. maturase or a variant thereof; in combination with a D4A, or a variant thereof, or a nucleic acid molecule encoding D4A, or a variant thereof, in a reverse transcription reaction. For example, as described herein D4A can be used in conjunction with E.r. maturase or a variant thereof to improve RT activity by reducing non-specific binding of primers to the E.r. maturase surface.

For example, in one embodiment, the method comprises mixing the agent for reducing non-specific binding and a reverse transcriptase, comprising an E.r. maturase or variant thereof, under suitable conditions; and contacting the reverse transcriptase to an RNA template to produce a transcribed DNA molecule from the RNA template.

In various embodiments, the present invention includes methods of using E.r. maturase, or a variant thereof, or a nucleic acid encoding E.r. maturase or a variant thereof; in an optimized reaction buffer in a reverse transcription reaction. For example, in one embodiment, the method comprises adding a reverse transcriptase, comprising an E.r. maturase or variant thereof, to an optimized reaction buffer; and contacting the reverse transcriptase to an RNA template to produce a transcribed DNA molecule from the RNA template. In one embodiment, the optimized reaction buffer comprises Tris at a concentration of about 10 mM to about 100 mM; KCl at a concentration of about 100 mM to about 500 mM, $MgCl_2$ at a concentration of about 0.5 mM to about 5 mM, DTT at a concentration of about 1 mM to about 10 mM, and wherein the reaction buffer has a pH of about 8 to 8.5. In one embodiment, the optimized reaction buffer comprises about 50 mM Tris, about 200 mM KCl, about 2 mM $MgCl_2$, about 5 mM DTT; and has a pH of about 8.3.

In one embodiment the optimized reaction buffer comprises a protein stabilizing agent. Exemplary protein stabilizing agents include, but are not limited to, osmolytic stabilizers such as glycerol, erythritol, arabitol, sorbitol, mannitol, xylitol, mannisdomannitol, glucosylglycerol, glucose, fructose, sucrose, trehalose, isofluorosid, dextrans, levans, and polyethylene glycol; amino acids and derivatives thereof such as glycine, alanine, proline, taurine, betaine, octopine, glutamate, sarcosine, γ-aminobutyric acid, trimethylamine, N-oxide (TMAO); ionic stabilizers such as citrate, sulfates, acetate, phosphates, and quaternary amines; and proteins such as bovine serum albumin (BSA).

In one embodiment, the optimized reaction buffer comprises trehalose at a concentration of about 0.1 M to about 1 M. In one embodiment, the optimized reaction buffer comprises betaine at a concentration of about 0.1 M to about 10 M. In one embodiment, the optimized reaction buffer comprises BSA at a concentration of about 0.5 mg/mL to about 2 mg/mL. In one embodiment, the optimized reaction buffer comprises glycerol at a concentration of about 1% to about 50%.

Using E.r. maturase and variants thereof

Any technology that employs reverse transcription as a method or step can utilize the E.r. maturase enzyme, and variants thereof, of the present invention. In various embodiments, the improved E.r. maturase is used to perform reverse transcription as part of an assay. In various embodiments, the assay may be at least one selected from the group RT-PCR, qRT-PCR, capillary electrophoresis (CE) for RNA-structure mapping (such as SHAPE-seq or SHAPE-map, DMS-seq), in-cell sequencing, next-generation RNA sequencing (RNA-seq), nanopore sequencing, cDNA library synthesis, cDNA synthesis, and a combination thereof.

In certain aspects, the method provides for reverse transcription at physiologic temperatures, or at lower temperatures relative to that required when using non-E.r maturase-derived reverse transcriptases. In certain instances, the lower temperature of the reverse transcription reaction provides a decreased rate of degradation of the RNA molecule during the reaction, relative to the rate of degradation of an RNA molecule in a reverse transcription reaction that uses a non-E.r maturase-derived reverse transcriptase.

In one embodiment, the method comprises reverse transcription of a long and/or complex RNA molecule. In certain embodiments, the reverse transcriptases described herein have reduced turnover, thereby allowing the synthesis of longer reads and full-length DNA products. Further, it is demonstrated herein that the reverse transcriptases of the present invention are able to reverse transcribe RNA templates having complex structure.

In one embodiment, the method comprises formulating a reaction solution comprising a low concentration of a reverse transcriptase described herein, compared to the concentration required for a reaction using a different reverse transcriptase.

In one embodiment, the method comprises a single reaction amplification of RNA, made possible by the true thermocycling ability of the reverse transcriptases described herein. For, example, the thermocycling ability of the reverse transcriptases described herein allows for the amplification of RNA without the need for DNA replication.

In one embodiment, the improved E.r. maturase enzyme is utilized in a quantitative RT-PCR (qRT-PCR) procedure. In qRT-PCR, the formation of PCR products is monitored in each cycle of the PCR. The amplification is usually measured in thermocyclers which have additional devices for measuring fluorescence signals during the amplification reaction. See, for example, U.S. Pat. Nos. 6,174,670, and 8,137,616. In one embodiment, the qRT-PCR procedure is carried out using a thermostable improved E.r. maturase enzyme, without a DNA→DNA polymerase.

In one embodiment, the improved E.r. maturase enzyme is utilized in a capillary electrophoresis (CE) for RNA-structure mapping procedure. The application of capillary electrophoresis to RNA structure probing is an important step in increasing the throughput of RNA structure data. Although RNA probing in solution can be readily implemented for short RNAs, probing of long RNAs can be challenging without the improved E.r. maturase enzyme. Gel electrophoresis typically resolves about a hundred bases of RNA at a time, and hence probing an RNA of several kilobases long might require running tens to hundreds of gels. Capillary electrophoresis allows the resolution of 300-650 bases from a structure probing experiment and multiple lanes can be run at the same time to increase the throughput of RNA structure probing. The readout of the probing experiment is typically through the reverse transcription of a 5' fluorescently labeled DNA primer that anneals specifically to the RNA of interest. If the RNA is several kilobases long, multiple primers are designed to anneal along the length of the transcript. Modification or cleavage of the RNA template results in premature stops in the primer extension reaction, leading to different lengths of the cDNA product which are resolved by capillary electrophoresis. Software tools such as CAFA and Shapefinder can automate the data acquisition from capillary electrophoresis and further improve speed and accuracy (see, for example, Wan, Y. et al., 2011, Nat Rev Genet., 12(9):1-26).

In one embodiment, the improved E.r. maturase is utilized in a next-generation RNA sequencing (RNA-seq) procedure. High-throughput RNA sequencing (RNA-Seq) technology, enabled by recent developments in next generation sequencing, has become a powerful tool in analyzing gene expression profiles, detecting transcript variants, and understanding the function of non-coding regulatory RNAs. A standard RNA-Seq library is generated from ligating sequencing adapters to double-stranded DNA. There are two main classes of methods to prepare strand-specific RNA-Seq libraries. The first method comprises ligating different adapters to the 3' and 5' ends of the RNA molecules (see e.g. Ion Total RNA-Seq Kit v2 from Life Technologies). Another, more widely used method comprises incorporating dUTP in addition to dNTPs in the second strand DNA synthesis. Following adapter ligation, the second strand DNA can be specifically digested by an Uracil-N-glycosylase (UNG) enzyme so that only the library strand containing the first strand cDNA will be sequenced and information on the direction of the transcripts can therefore be obtained (see M. Sultan et al., Biochemical and Biophysical Research Communications 422 (2012) 643-646; also see PCT Patent Application Number PCT/EP2016/069997).

The invention is also directed to methods for making one or more nucleic acid molecules and/or labeled nucleic acid molecules, comprising mixing one or more nucleic acid templates (e.g., one or more RNA templates or messenger RNA templates) with one or more polypeptides of the invention having reverse transcriptase activity and incubating the mixture under conditions sufficient to synthesize one or more first nucleic acid molecules complementary to all or a portion of the one or more nucleic acid templates, wherein at least one of the synthesized molecules are optionally labeled and/or comprise one or more labeled nucleotides and/or wherein the synthesized molecules may optionally be modified to contain one or more labels. In one embodiment, the one or more first nucleic acid molecules are single-stranded cDNA molecules. Nucleic acid templates suitable for reverse transcription according to this aspect of the invention include any nucleic acid molecule or population of nucleic acid molecules (e.g., RNA, mRNA), particularly those derived from a cell or tissue. In one aspect, a population of mRNA molecules (a number of different mRNA molecules, typically obtained from cells or tissue) are used to make a labeled cDNA library, in accordance with the invention. Exemplary sources of nucleic acid templates include viruses, virally infected cells, bacterial cells, fungal cells, plant cells and animal cells.

The invention also concerns methods for making one or more double-stranded nucleic acid molecules (which may optionally be labeled). Such methods comprise (a) mixing one or more nucleic acid templates (e.g., RNA or mRNA, or a population of mRNA templates) with one or more polypeptides of the invention having reverse transcriptase activity; (b) incubating the mixture under conditions sufficient to make one or more first nucleic acid molecules complementary to all or a portion of the one or more templates; and (c) incubating the one or more first nucleic acid molecules under conditions sufficient to make one or more second nucleic acid molecules complementary to all or a portion of the one or more first nucleic acid molecules, thereby forming one or more double-stranded nucleic acid molecules comprising the first and second nucleic acid molecules. In accordance with the invention, the first and/or second nucleic acid molecules may be labeled (e.g., may comprise one or more of the same or different labeled nucleotides and/or may be modified to contain one or more of the same or different labels). Thus, labeled nucleotides may be used at one or both synthesis steps. Such methods may include the use of one or more DNA polymerases as part of the process of making the one or more double-stranded nucleic acid molecules. The invention also concerns compositions useful for making such double-stranded nucleic acid molecules. Such compositions comprise one or more reverse transcriptases of the invention and optionally one or more DNA polymerases, a suitable buffer and/or one or more nucleotides (e.g., including labeled nucleotides).

The invention is also directed to nucleic acid molecules and/or labeled nucleic acid molecules (particularly single- or double-stranded cDNA molecules) produced according to the above-described methods and to kits comprising these nucleic acid molecules. Such molecules or kits may be used to detect nucleic acid molecules (for example by hybridization) or for diagnostic purposes.

Producing Improved E.r. Maturase

In various embodiments, the improved E.r. maturase is produced by methods described herein or methods generally available in the art of cell and molecular biology. Generally, the improved E.r. maturase may be produced by a live host cell, or by synthetic means. In various embodiments, the improved E.r. maturase is encoded by a polynucleotide operably linked to a promoter, which is inserted into an expression vector for expression in a host cell. The vector is then inserted into the host cell, and a selection step may be performed to enrich the culture for host cells in which the vector has been inserted. After selection, fresh cultures may be inoculated with host cells carrying the vector, and expression of the improved E.r. maturase may be carried out either during exponential growth or at another stage of growth of the culture of host cells. After expression of the improved E.r. maturase, standard or innovative biochemical purification steps may be performed to purify the protein from cellular debris. See, for example, Sambrook et al. (2012, Molecular Cloning: A Laboratory Manual, Cold Spring Harbor Laboratory, New York).

The present invention is also directed to nucleic acid molecules (e.g., vectors) comprising a gene or nucleic acid molecules encoding the mutant or modified reverse transcriptases of the present invention (or fragments thereof including fragments having polymerase activity) and to host cells comprising such DNA or other nucleic acid molecules. Any number of hosts may be used to express the gene or nucleic acid molecule of interest, including prokaryotic and eukaryotic cells. In some embodiments, prokaryotic cells are used to express the reverse transcriptases of the invention. One example of a prokaryotic host suitable for use with the present invention is *Escherichia coli*. Examples of eukaryotic hosts suitable for use with the present invention include fungal cells (e.g., *Saccharomyces cerevisiae* cells, *Pichia pastoris* cells, etc.), plant cells, and animal cells (e.g., *Drosophila melanogaster* cells, *Spodoptera frupperda* Sf9 and Sf21 cells, Trichoplusa High-Five cells, *C. elegans* cells, *Xenopus laevis* cells, CHO cells, COS cells, VERO cells, BHK cells, etc.). Polypeptides of the invention may be purified and/or isolated from a cell or organism expressing them, which may be a wild type cell or organism or a recombinant cell or organism. In some embodiments, such polypeptides may be substantially isolated from the cell or organism in which they are expressed.

The invention also relates to a method of producing reverse transcriptases of the invention, said method comprising: (a) culturing a host cell comprising a gene or other nucleic acid molecule encoding a reverse transcriptase of the invention (preferably such reverse transcriptase gene or other nucleic acid molecule is contained by a vector within the host cell); (b) expressing the gene or nucleic acid molecule; and (c) isolating or purifying said reverse transcriptase.

Kits

The invention is also directed to kits for use in the production methods of the invention. In various embodiments, the present invention provides a kit to produce E.r. maturase protein, or a variant thereof. In one embodiment, the kit comprises an expression system that comprises a polynucleotide encoding E.r. maturase polypeptide or a variant thereof. In one embodiment, the kit comprises an expression system that comprises a polynucleotide comprising or encoding a nucleic acid molecule that reduces non-specific binding. In one embodiment, the kit comprises an expression system that comprises a polynucleotide encoding a protein (e.g., heparin) that reduces non-specific binding. In one embodiment, the kit includes instructional material that describes the use of the kit to produce E.r. maturase protein, wherein the instructional material creates an increased functional relationship between the kit components and the individual using the kit. In one embodiment, the kit is utilized by one person or entity. In another embodiment, the kit is utilized by more than one person or entity. In one embodiment, the kit is used without any additional compositions or methods. In another embodiment, the kit is used with at least one additional composition or method.

The invention is also directed to kits for use in the reverse transcription methods of the invention. Such kits can be used for making nucleic acid molecules and/or labeled nucleic acid molecules (single- or double-stranded). Kits of the invention may comprise a carrier, such as a box or carton, having in close confinement therein one or more containers, such as vials, tubes, bottles and the like. In kits of the invention, a first container may contain one or more of the reverse transcriptase enzymes of the invention or one or more of the compositions of the invention. Kits of the invention may also comprise, in the same or different containers, at least one component selected from one or more DNA polymerases (e.g., thermostable DNA polymerases), a suitable buffer for nucleic acid synthesis and one or more nucleotides. In one embodiment, kits of the invention may also comprise, in the same or different containers, an agent that reduces non-specific binding of primers to the surface of E.r. maturase or variant thereof. In one embodiment, kits of the invention may also comprise, in the same or different containers, an optimized reaction buffer as described elsewhere herein, or components used to produce the optimized reaction buffer. Alternatively, the components of the kit may be divided into separate containers.

The invention is also directed to kits for use in methods of the invention. Such kits can be used for making, sequencing or amplifying nucleic acid molecules (single- or double-stranded), e.g., at the particular temperatures described herein. Kits of the invention may comprise a carrier, such as a box or carton, having in close confinement therein one or more (e.g., one, two, three, four, five, ten, twelve, fifteen, etc.) containers, such as vials, tubes, bottles and the like. In kits of the invention, a first container contains one or more of the reverse transcriptase enzymes of the present invention. Kits of the invention may also comprise, in the same or different containers, one or more DNA polymerases (e.g., thermostable DNA polymerases), one or more (e.g., one, two, three, four, five, ten, twelve, fifteen, etc.) suitable buffers for nucleic acid synthesis, one or more nucleotides and one or more (e.g., one, two, three, four, five, ten, twelve, fifteen, etc.) oligonucleotide primers. In one embodiment, kits of the invention may also comprise, in the same or different containers, an agent that reduces non-specific binding of primers to the surface of E.r. maturase or variant thereof, as described elsewhere herein. In one embodiment, kits of the invention may also comprise, in the same or different containers, an optimized reaction buffer as described elsewhere herein, or components used to produce the optimized reaction buffer. Alternatively, the components of the kit may be divided into separate containers (e.g., one container for each enzyme and/or component). Kits of the invention also may comprise instructions or protocols for carrying out the methods of the invention.

In various embodiments, the present invention provides a kit to use E.r. maturase protein, or a variant thereof, in a reverse transcription reaction. In one embodiment, the kit comprises E.r. maturase polypeptide or a variant thereof. In one embodiment, the kit includes instructional material that describes the use of the kit to use E.r. maturase protein, or a variant thereof, in a reverse transcription reaction, wherein the instructional material creates an increased functional relationship between the kit components and the individual using the kit. In one embodiment, the kit is utilized by one person or entity. In another embodiment, the kit is utilized by more than one person or entity. In one embodiment, the kit is used without any additional compositions or methods. In another embodiment, the kit is used with at least one additional composition or method.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: Optimization of *Eubacerium rectale* Maturase

Most group II introns encode maturase proteins that can function as reverse transcriptases (RTs) (Zimmerly S et al., 1995, Cell, 82:545-554; Matsuura M et al., 1997, Genes Dev, 11:2910-2924). These reverse transcriptases belong to the same family as the reverse transcriptases from non-long-terminal-repeat (non-LTR) retrotransposons, which are characterized by an N-terminus extension (RT0) and insertions between 7 sequence blocks that are conserved across all RTs (RT1-7) (Blocker F J et al., 2005, RNA, 11:14-28). Based on sequence conservation, the RT0 and RT1-7 regions, plus the insertions between these regions, comprise the N-terminal RT domain of group II intron maturases (Blocker F J et al., 2005, RNA, 11:14-28). The RT domain is comprised of the finger and palm subdomain of a polymerase, which contains the catalytic center and is responsible for polymerase fidelity and processivity (FIG. 4A) (Zimmerly S et al., 2001, Nucleic Acids Res, 29:1238-1250; Blocker F J et al., 2005, RNA, 11:14-28). C-terminus to the RT domains lies the X domain that is analogous to a polymerase thumb, and it functions in polymerase processivity (FIG. 4A) (Zimmerly S et al., 2001, Nucleic Acids Res, 29:1238-1250; Blocker F J et al., 2005, RNA, 11:14-28). Recent structural information on group II intron maturases confirmed the roles of RT and X domains in forming a canonical "right-hand" polymerase (FIG. 4B) (Qu G et al., 2016, Nat Struct Mol Biol, 23:549-557; Zhao C et al., 2016, Nat Struct Mol Biol, 23:558-565). In some group II introns, additional domains including D (DNA binding) domain and EN (endonuclease) domain could be found C-terminus to the X domain (FIG. 4A and FIG. 4B) (Blocker F J et al., 2005, RNA, 11:14-28; Agrawal R K et al., 2016, RNA Biol, 13(12):1218-1222; Qu G et al., 2016, Nat Struct Mol Biol, 23:549-557). These domains play critical auxiliary roles in group II intron retro-transposition (Singh N N et al., 2001, J Mol Biol, 309:361-386; Blocker F J et al., 2005, RNA, 11:14-28; Lambowitz A M et al., 2015, Microbiol Spectr, 3(1):1-41), however, whether they have direct contribution to reverse transcription activity is largely unknown. In vivo, the maturase protein forms a RNA-protein ribonucleoprotein (RNP) complex with its host intron through a positively charged surface on RT domain (Saldanha R., 1999, Biochemistry, 38:9069-9083; Qu G et al., 2016, Nat Struct Mol Biol, 23:549-557; Zhao C et al., 2016, Nat Struct Mol Biol, 23:558-565), and its reverse transcriptase activity is exerted in the context of this RNP complex.

A hallmark of maturase-catalyzed reverse transcription reactions is high processivity. Highly processive reverse transcription is important for group II intron biology, as it is required for successful propagation of group II introns and their healthy relationship with the hosts (Mohr S et al., 2013, RNA, 19:958-970; Lambowitz A M et al., 2015, Microbiol Spectr, 3(1):1-41). Indeed, some studies have reported the high RT processivity of group II intron maturases (Mohr S et al., 2013, RNA, 19:958-970) and related non-LTR retrotransposon RTs (Bibillo A et al., 2002, J Biol Chem, 277:34836-34845; Cost G J et al., 2002, EMBO J, 21:5899-5910; Piskareva O et al., 2006, FEBS Lett, 580:661-668). High processivity could be tremendously useful for tool RT enzymes in applications such as cDNA library construction (Mohr S et al., 2013, RNA, 19:958-970), splice site characterization (Nilsen T W et al., 2010, Nature, 463:457-463) and RNA mapping by mutational profiling (eg. SHAPE-MaP (Siegfried N A et al., 2014, Nat Methods, 11:959-965) and DMS-MaP (Zubradt M et al., 2017, Nat Methods 14: 75-82)).

However, the understanding of the mechanism underlying the high processivity of group II intron maturases is very poor. Such lack of mechanistic understanding is partly due to the lack of structural information of group II intron maturases for the last 20 years. In 2016, both 1.2 Å and 2.1 Å crystal structures of group II intron maturase RT domains (Zhao C et al., 2016, Nat Struct Mol Biol, 23:558-565) and a 3.8 Å cryo-electron microscopy (cryo-EM) structure of group II intron full-length maturase in complex with its host intron RNA (Qu G et al., 2016, Nat Struct Mol Biol, 23:549-557) were reported. These structures represent the beginning of a new era of structural-guided functional analysis for group II intron maturases.

To meet the growing need for processive, high-fidelity reverse transcription of large RNA molecules, an unusually powerful new RT is engineered herein, derived from a group II intron from the eubacteria *Eubacterium rectale* (E.r. RT) (Zhao C et al., 2016, Nature structural & molecular biology, 23(6):558-65). The molecular structure of this enzyme was solved crystallographically to exceptionally high resolution (Zhao C et al., 2016, Nature structural & molecular biology, 23(6):558-65). Even before the optimization described herein, this enzyme promotes quantitative, end-to-end reverse-transcription of long RNA molecules, thereby providing the foundation for a versatile new set of genomic tools (FIG. 1).

The E.r. RT enzyme is further developed and optimized herein, demonstrating its broad utility for diverse transcriptomics applications. The enzyme is capable of addressing at least two distinct problems. First, simultaneous mutations within HIV genomes are monitored, enabling the determination of how coupled mutations lead to drug resistance in patients over time, providing a powerful tool for studies of viral evolution and function. Second, tissue-specific linkage between patterns of alternative-splice site choice is amenable to study in eukaryotic genes, including the extraordinarily complex Dscam1 gene from Drosophila melanogaster. This goal was previously impossible because of the inability to obtain end-to-end sequences. The present invention enables investigators to finally track populations of alternatively spliced gene products, providing new insights into tissue-specific and developmentally-controlled gene expression.

The scientific premise of the present invention is that a powerful new family of RTs is used to accurately perform end-to-end sequencing of long RNA molecules, and this new RT technology is applied to address unmet needs in transcriptomics, biotechnology and medicine.

The utility of the E.r. RT is exemplified by its application in studies of HIV diversification in patients. HIV is a singled-stranded RNA virus that evolves as a quasispecies (i.e., "swarm") during infection, with millions of individual viruses that rapidly evolve to generate extensive genetic diversity within a single patient (Kutilek V D et al., 2003, Curr Drug Targets Infect Disord., 3(4):295-309). HIV diversification plays a major role in disease progression, resistance to combination antiretroviral treatments (cART) and vaccine responses (Flynn W F et al., 2015, PLoS Comput Biol. 11(4):e1004249). HIV is present in the blood throughout infection, and can be sampled over time from the blood. HIV genetic changes that result from drug treatments have been pinpointed, but efforts to build on these findings are severely hampered by the inability of commercial RTs to faithfully copy the full-length ~9 kb HIV virion RNA from individual viruses in the swarm for sequence analysis. This has resulted in viral sequencing strategies that rely on short reads, ~100-2000 bp, which disrupts genetic linkage analysis (Flynn W F et al., 2015, PLoS Comput Biol. 11(4): e1004249; Routh A et al., 2015, Methods, 91:40-7). This problem limits identification of distal genetic effects, epistasis, that coevolve in individual viruses contributing to drug or immunological resistance and gain of viral fitness within a swarm (Flynn W F et al., 2015, PLoS Comput Biol. 11(4):e1004249; Routh A et al., 2015, Methods, 91:40-7).

To overcome the limitations of conventional RTs, the E.r. RT is evaluated for its ability to generate long-read cDNAs. The Primer ID methodology has been modified, which was successfully used for tagging viruses within a swarm but was limited by short-read sequencing methodologies (Jabara C B et al., 2011, Proc Natl Acad Sci USA, 108(50):20166-71). The modified Primer ID methodology is used with the longer cDNAs produced from E.r. RTs and allows for aligned sequence analysis of individual full-length HIVs that compose the evolving patient swarm before and during cART. By combining ultra-processive E.r. RTs with long-read sequencing capability, it is possible to fundamentally improve next-generation sequencing (NGS), resulting in meaningful sequence and genetic analysis of individual viruses in patients before, during, and in some cases, after drug treatment.

A second example of E.r. RT utility is in the study of alternative splicing, which is an essential mechanism for regulating gene expression and increasing protein diversity. The majority of genes within metazoan genomes encode alternatively spliced pre-mRNAs (Gerstein M B et al., 2014, Nature, 512(7515):445-8). For example, over 60% of Drosophila genes (Graveley B R et al., 2011, Nature, 471(7339): 473-9) and over 90% of human genes (Wang E T et al., 2008, Nature, 456(7221):470-6; Pan Q et al., 2008, Nat Genet, 40(12):1413-5) encode pre-mRNAs that undergo alternative splicing. While many of these genes encode only two or three isoforms, some encode hundreds, thousands, and even tens of thousands of isoforms. In Drosophila, 47 genes encode over 1,000 isoforms each, and together account for 50% of all expressed transcripts (Brown J B et al., 2014, Nature, 512(7515):393-9). The most extreme example of this is the Drosophila Dscam1 gene, which contains 115 exons, 95 of which are alternatively spliced, and which has the capability to express 38,016 distinct mRNA and protein isoforms (Schmucker D et al., 2000, Cell, 101(6):671-84).

Although high-throughput sequencing has revolutionized the characterization of transcriptomes and the study of alternative splicing, many technical issues limit the ability to fully characterize complete isoforms. The biggest problem is that in many genes, alternatively spliced regions exist at multiple locations within individual pre-mRNA transcripts and these regions are often spaced further apart than the read lengths of most high throughput sequencing platforms. Consequently, much effort has been devoted to developing transcript assembly and quantitation software tools (Boley N et al., 2014, Nat Biotechnol, 32(4):341-6; Grabherr M G et al., 2011, Nat Biotechnol, 29(7):644-52; Trapnell C et al., 2010, Nat Biotechnol, 28(5):511-5.). Although these computational approaches may correctly assemble many transcripts from short-read data, they rarely assemble transcripts of genes that express multiple isoforms. In fact, one is likely unable to use any software to successfully assemble transcripts of complex alternatively spliced genes such as Dscam1 or Mhc. Additionally, available software tools have difficulty quantitating transcripts that have many isoforms, and for genes with distantly located alternatively spliced regions, they can only infer, and not directly measure, which isoforms were present in the original RNA sample (Garber M et al., 2011, Nat Methods, 8(6):469-77). The availability of a robust and processive RT for preparing full-length cDNA sequencing libraries transforms the ability to thoroughly and accurately interrogate transcriptomes.

Innovation in the design of sequencing enzymes is just as important as innovation in sequencing hardware and software. Currently, RNA sequencing technologies are built on platforms that utilize MLV RT enzymes with undesirable attributes such as poor processivity and high error rates. An accurate RT that efficiently carries out end-to-end sequencing of long RNAs is inherently innovative and is leading to innovations in the study of long noncoding RNAs, alternative splicing products and viral RNA genomes, all within complex mixed populations. An innovative RT platform facilitates improvement in hardware and sequencing protocols because practitioners no longer need to compensate for short, less accurate reads.

With the E.r. RT enzyme, end-to-end sequencing of individual HIV RNAs from patient populations can maintain genetic linkage in individual viruses. This allows researchers and clinicians an unprecedented opportunity to interrogate dynamic, coupled changes in viral populations by following individual viruses during development of resistance to cART and vaccine immunization. Moreover, the methodologies and protocols provided herein extend to investigations of coupled transcriptional changes in any microorganism or during pathogen-host interaction.

Using a highly processive E.r. RT enzyme disclosed herein, end-to-end sequencing of long, alternatively spliced mRNA pools enables monitoring distributions of alternatively spliced products for the first time, thereby making it possible to understand the link between spliced product distribution and tissue- or developmental-specific patterns of gene expression.

The presently disclosed highly processive and accurate RT enzymes leads to innovations in transcriptomics by allowing the generation of full-length cDNA libraries, an area where significant advances are desperately needed.

1. Optimizing Properties of the E.r. RT, Producing a Robust New Reagent for Long, Accurate Reads While it is clear that a processive, highly accurate RT transforms transcriptomics and biotechnology, it is important that new RT technologies are quantitatively evaluated, benchmarked and optimized before they are widely utilized. Therefore, a robust, varied set of conditions have been established for obtaining full-length reverse-transcription products from long, structured RNA molecules (>10,000 nts in length) in high yield. To that end, E.r. RT extension processivity, sequence accuracy, speed, solubility, and stability have been identified, and the resultant parameters are used to optimize reaction conditions and the enzyme construct itself. The ability to copy highly stable RNA substructures has been improved. Reaction conditions are improved so they are robust and can be readily employed by other researchers. The results are benchmarked by conducting comparative studies with other known RT enzymes, none of which have been quantitatively evaluated on templates longer than 1,000 nts. The art provides quantitative studies of translocating helicase enzymes and RNA polymerases, which can serve to inform the present analysis (Beran R K et al., 2006, J Mol Biol, 358(4):974-82; Dumont S et al., 2006, Nature, 439(7072):105-8; Jankowsky E et al., 2000, Nature, 403(6768):447-51; Kawaoka J et al., 2004, Nat Struct Mol Biol, 11(6):526-30; Myong S et al., 2007, Science, 317(5837):513-6; Pang P S et al., 2002, EMBO J, 21(5):1168-76; Serebrov V et al., 2009, J Biol Chem, 284(4):2512-21; Serebrov V et al., 2004, Nature, 430(6998): 476-80; Wagner J D et al., 1998, EMBO J, 17(10):2926-37).

A. Establish Quantitative Metrics for RT Function to Facilitate Comparison and Optimization (i). Speed To rigorously measure RT processivity and accuracy, and to determine reaction conditions for optimal enzyme efficiency, it is important to determine the velocity (nucleotides incorporated vs. time) of the E.r. RT during the individual initiation and elongation phases of reverse-transcription. Using RT deletion mutants that undergo only the initiation step of primer extension (Zhao C et al., 2016, Nature structural & molecular biology, 23(6):558-65), previous results indicate that addition of the first 12-15 nucleotides represents a distinct initiation phase of reaction. To measure the velocity of this phase, RT is incubated with primer/template, initiating the reaction with a $^{32}$P-labeled primer and time points are taken with a quench-flow reactor (Li J et al., 2016, J Biol Chem, 291(19):10067-77), before products are separated by electrophoresis and the evolution of short products (<15 nts) plotted vs. time. Elongation velocity is obtained similarly, monitoring the time-dependent evolution of extended cDNA products on a long RNA template (9,000 nts).

(ii). RT Dissociation Rate Constant

One important determinant of polymerase processivity is the tendency of the enzyme to fall off the template ($k_{off}$). Indeed, the formal definition of processivity (P) for a directional enzyme is how fast it moves forward vs. how fast it falls off ($P=k_{forward}/(k_{off}+k_{forward})$) (Lohman T M et al., 1996, Annu Rev Biochem, 65:169-214). To obtain the value of $k_{off}$, pulse-chase experiments are performed, in which the RT reaction is initiated with a radiolabeled primer. After allowing sufficient time for partial elongation, a high concentration of cold primer-template is added to trap dissociating polymerase, and the rate constant for complete extension in the presence and absence of trap is monitored, extracting the $k_{off}$ from the difference in these values.

(iii). Processivity

To evaluate variants of the E.r. RT and compare them with other enzymes, quantitative values for E.r. processivity are obtained. While this can be determined formally, from values of $k_{forward}$ and $k_{off}$ (as above), processivity can be defined more simply as the frequency of RT dissociation per initiation (Mohr S et al., 2013, RNA, 19(7):958-70) on a template. This is measured by initiating the RT reaction in the presence of a trap RNA (which prevents reassociation of free RT), separating the products on a sequencing gel, and comparing the ratio of radiolabeled full-length products with abortive products. Studies show that the E.r. RT is highly processive on structured templates and that it is significantly more processive than Superscript IV (SSIV) or TGIRT (FIG. 2). Metrics of processivity on different RNA templates of varying length (such as HCV RNAs, see FIG. 1) are obtained, in the presence and absence of trap, determining fractional values for successful elongation that is compared with mutants and/or variants and as a function of reaction condition (see below).

(iv). Stability and Solubility

The thermal stability of the wild type (WT) E.r. RT protein is determined under diverse ionic conditions, solvent, temperature and detergents to identify conditions for optimal stability of the WT enzyme and to establish benchmarks for subsequent structure/function studies. Intrinsic thermal stability of the RT is monitored using a thermofluor assay, in which protein denaturation is measured in the presence of a dye that binds to folded proteins, such as SYPRO orange (Lavinder J J et al., 2009, J Am Chem Soc, 131(11):3794-5). Samples are studied in a 96-well plate in a real-time PCR instrument. Decrease in emission or increase in fluorescence intensity is monitored as a function of temperature (Huynh K et al., 2015, Curr Protoc Protein Sci, 79:28, 9, 1-14) to determine the free energy of stabilization. Functional stability is measured by monitoring primer extension as a function of the conditions described above. Solubility is measured similarly by dynamic light scattering (Chaudhuri R et al., 2014, AAPS J, 16(1):48-64).

(v). Error Rate and Relative Incorporation Accuracy

Misincorporation frequency and fidelity of the E.r. RT is measured and compared with other common RTs using global deep-sequencing methods (Gout J F et al., 2013, Proc Natl Acad Sci USA, 110(46):18584-9). Specifically, an assay has been developed in which a known RNA template is reverse-transcribed using a primer comprising a random-hexamer and a unimolecular barcode (UMI), second strand synthesis is performed, Illumina adapters are ligated, the resulting cDNA is amplified by PCR, and Illumina sequencing of the libraries is performed. The sequence reads are analyzed to collapse PCR duplicates using the UMI barcodes creating a consensus sequence for each molecule, thereby removing any mutations that arose during PCR or sequencing errors and retaining only mutations that occurred during reverse transcription. The consensus reads are aligned to the reference sequence, and the frequency of RT-induced mutations determined. In an experiment using a set of 96 synthetic RNAs from the External RNA Controls Consortium (ERCC) as a template it was found that the error rate profile of the WT E.r. RT is comparable to, if not slightly better than that of SSIV. This error-rate determination assay is optimized, and is used to characterize the E.r. RT variants that are generated, and to compare them with commercially available RT enzymes. To obtain precise values for mismatch discrimination in the form of selectivity constants (e.g. fraction correct/incorrect), a classic pre-steady-state kinetic analysis of single nucleotide incorporation into radiolabeled primer-templates that encode a templating base for a single type of nucleotide is performed. Reaction is initiated by providing the dNTP for the complementary nucleotide, or for a mismatch and time points are taken on a quench-flow apparatus. Products are resolved on a denaturing gel and data are plotted to obtain the relative incorporation rate for matched and mismatched nucleotides (DeLucia A M et al., 2006, J Biol Chem, 281(37):27286-91; Heyn B et al., 2015, Biol Chem, 396(12):1315-23.).

(vi). Template Switching Frequency

It has been previously shown that template switching tends to be more problematic during PCR rather than the RT steps of RNA sequencing protocols (Bolisetty M T et al., 2015, Genome Biol, 16:204). For example, using a predefined mixture of six distinct isoforms of Dscam1 mRNAs and nanopore sequencing, template switching was observed with frequencies of 0.2%, 1% and 32% in libraries generated using 20, 25, and 30 rounds of PCR using Superscript II RT. Nonetheless, it is important to evaluate the frequency of template switching with E.r. RT and mutants and variants thereof. In experiments to evaluate this issue, the E.r. RT was used to extend a radiolabeled primer annealed to a long RNA template (600 nts, 100 nM concentration) in the presence of a second RNA molecule (200 nt, at concentrations ranging from 100 nM to 2 μM) with which it shares 110 nts of homology. No template switching was observed, with a detection limit of 0.01 fmoles. The extent of template switching on all E.r. RT variants as well as commercial RTs is monitored in two ways. First, the biochemical assay just described is performed using two RNAs of different lengths that share a central region of homology. Second, experiments are performed using complex mixtures of highly similar RNAs followed by nanopore sequencing. Specifically, a pool of Dscam1 transcripts that contains 96 different isoforms that differ from one another in at least two of the three variable exon clusters are used. The pools are prepared by in vitro transcription and gel purification of a collection of 96 individual clones of Dscam1 isoforms. The RNAs are quantitated and mixed together in either an equimolar ratio or in a dilution series where different transcripts will differ by up to two orders of magnitude. These pools are used to prepare cDNA libraries using the same E.r. RT variants and reaction conditions described above and then sequenced on a MinION to a depth of >10,000 reads per library. Which isoform each read corresponds to is determined, and the extent of template switching is calculated based on the number of reads corresponding to input isoforms and template-switched isoforms (isoforms that were not present in the input RNA pool). Together, these approaches are providing valuable information about the frequency of template-switching of the E.r. RT enzymes, which has important implications in interpreting long-read sequence data.

(vii). Optimization

With the above parameters in hand, benchmarks for establishing a set of more highly optimized reaction conditions have been developed (see below). In addition, the ability of the E.r. RT to copy highly structured RNA templates is optimized, and the E.r. protein structure and sequence are optimized to further improve its performance, thereby expanding its utility in biotechnology. To optimize reaction conditions, E.r. RT performance is tested (with special emphasis on stability, processivity and accuracy) as a function of buffer composition. Specifically, concentrations of monovalent and divalent salts (including, but not limited to KCl, $NH_4C_1$ and $MgCl_2$), organic polyamines (e.g. spermidine), detergents and stabilizers such as glycerol, trehalose and other buffer additives are varied. It is important to be particularly attentive to improvements in thermal stability, as this can be an ideal parameter for optimization to obtain a thermocycling RT.

B. Evaluate Behavior of the E.r. RT on Templates Containing Stable RNA Substructures A robust end-to-end RNA sequencing enzyme needs more than processivity: it must also have sufficient motive force to disrupt and copy stable RNA structures that form within the template. RNA molecules are extensively structured, even in coding regions, and RNA substructures can present themselves as obstacles that block a weak polymerase. Thus, it therefore important to evaluate and optimize the ability of E.r. RT to open and copy a diversity of RNA substructures without hopping over them and reinitiating at downstream portions of the template. Group II intron maturase RTs, such as that of E.r., are thought to be inherently strong polymerases because they have evolved to copy highly structured group II intron molecules during retrotransposition. Presently disclosed data demonstrate that the E.r. RT can successfully copy the exceptionally structured RNA genome of HCV (FIG. 1), indicating that it has a high degree of processivity on structured templates. A systematic analysis of template structure for E.r. RT would provide valuable comparative information for optimization and interpretation of any abortive products that are observed. A broad set of stable RNA substructures are inserted into RNA templates for the E.r. RT, varying secondary and tertiary structural stability. RNA templates are made by cloning the substructures described below into the span of a well-characterized RNA sequence (such as the interior of the HCV coding region, see FIG. 1) and transcribing these on large scale with T7 RNA polymerase.

(i). Stable Stems

To test and optimize the ability of an E.r. RT to unwind and copy stable RNA stems (as shown in FIG. 1), a template containing a stable inverted repeat sequence that is located 200 nucleotides from the primer binding site is created. This enables one to test the power of the translocating RT during the elongation phase (while it is running). The inverted repeat forms a stem composed of ten alternating G-C pairs, terminated by a loop sequence of UUU. A series of constructs in which this stem is elongated sequentially by 20 base-pairs of known thermodynamic stability (RNA duplex strength is readily calculated using nearest-neighbor interaction energies) is generated (Turner D H et al., 2010, Nucleic Acids Res, 38(Database issue):D280-2). The sequence and stability are varied and then the processivity and speed of the E.r. RT as it copies these templates are monitored.

(ii). Pseudoknots and RNA Tertiary Structures

A series of stable RNA tertiary structures are inserted at the terminus of the RNA stem-loop in the construct described above. Specifically, the frame-shifting pseudoknot from HIV (Staple D W et al., 2005, J Mol Biol, 349(5): 1011-23), the Azoarchus group I intron (Adams P L et al., 2004, Nature, 430(6995):45-50), the *Oceanobacillus iheyensis* group II intron (Marcia M et al., 2012, Cell, 151(3): 497-507; Toor N et al., 2008, Science, 320(5872):77-82.), stable K-turns (such as the one in SAM-I riboswitch) (Montange R K, et al., 2006, Nature, 441(7097):1172-5), and other structurally-characterized motifs of known thermodynamic stability (Butcher S E et al., 2011, Acc Chem Res, 44(12):1302-11) are tested. Whether the E.r. RT copies these structures, and how they affect processivity, speed, and other parameters described herein is determined.

(iii). Elevated $Mg^{2+}$

RNA structures become sharply stabilized with increasing $Mg^{2+}$. Although the influence of $Mg^{2+}$ is studied, it is important to examine it in the context of highly structured RNA templates.

C. Re-Engineer the RT Structure to Optimize Accurate, Processive RT Activity

Using structure-guided mutagenesis, the enzyme itself is optimized before it is widely distributed as a biotechnological tool. For example, enzyme features that are not relevant to RT function are eliminated, thereby enhancing solubility and stability, and enhancing motifs that contribute to processivity.

(i). Streamlining the RT

Like all group II intron maturases, the E.r. RT has additional protein domains that contribute to RNA splicing and transposition, but do not play a role in RT function. For example, the full-length maturase RT contains a secondary RNA binding site and DNA binding domain that can influence stability, specificity, and efficiency (Blocker F J et al., 2005, Rna, 11(1):14-28). To address these issues, site-directed mutagenesis is used to delete the C-terminal DNA binding domain and mutate the secondary RNA binding sites on the surface of the protein (Zhao C et al., 2016, Nature structural & molecular biology, 23(6):558-65; Gu S Q et al., 2010, Rna, 16(4):732-47), exchanging the conserved Lys and Arg regions with polar groups such as Ser. Without wishing to be bound by any particular theory, it is believed that these changes reduce nonspecific binding of the RT to the template, forcing binding exclusively at the polymerase cleft. The binding domain is altered through mutagenesis, using the parameters described above to test whether the mutants exhibit enhanced or reduced functionality. Some alterations may facilitate enzyme turnover, because they have little or no affinity for the product cDNA.

(ii). Enhance Processivity

The structural and functional analysis of the E.r. RT and related RTs has demonstrated that, in addition to the thumb domain, the maturase RT enzymes have a unique feature that appears to contribute to their unusually high processivity. Adjacent to the primer grip region (pink, FIG. 3), there is a structural element called the α-loop (yellow, FIG. 3), which is positioned to clasp the template and maintain processive nucleotide addition by the RT. Deletion of the α-loop does not prevent productive initiation, but it inhibits processive elongation by the RT (FIG. 3B). In the E.r. RT, the loop sequence is MIDDEYEDSIV<u>GTPQGG</u> (SEQ ID NO: 20), and the C-terminal portion of this sequence is almost invariant among maturase RTs (bold and underlined). The N-terminal region of this sequence is mutated, and whether alterations influence processivity or off-rate (see above) is determined. Specifically, an alanine scan, a polar residue scan (with Gln residues), and an electrostatic scan (with Glu residues) are performed. Production and testing of these mutants is rapid given that a reasonable number of loop positions is tested. In addition, the N-terminal region is substituted with multiple glycines, which tend to make loops more floppy, and with alanines, which rigidify loop sequences (Chen X et al., 2013, Adv Drug Deliv Rev, 65(10):1357-69). Finally, mutations are incorporated on the surface of the thumb domain, optimizing its ability to clasp the template. Any variants with improved properties are examined on structured RNA templates to identify any enhancements or diminutions in function.

(iii). Enhance Thermostability

Proteins identified in mesophiles (such as the E.r. RT) can be engineered to have properties more typical of a thermophilic protein (Anbar M et al., 2012, Appl Environ Microbiol, 78(9):3458-64; Steiner K et al., 2012, Comput Struct Biotechnol J, 2:e201209010), such as reactivity at high temperatures, and even thermocycling behavior, which would be a game-changing advance in RT technology since it would enable amplification of RNA templates in a single reaction. While the TGIRT RT enzyme was initially identified in a thermophile, it is not highly soluble and does not thermocycle. It is therefore advantageous to optimize the more processive, structurally-characterized E.r. RT (Zhao C et al., 2016, Nature structural & molecular biology, 23(6): 558-65). Analysis of thermophilic protein structure and function suggests that they tend to have larger numbers of side-chain hydrogen bonds and salt-bridges within rigid sections of the tertiary structure (Kumar S et al., 2000, Protein Eng, 13(3):179-91). Guided by the high-resolution structure of the E.r. RT, Lys-Glu pairs are engineered at positions that are proximal in 3-D space (FIG. 3).

Interpretation of the optimization results is straightforward because all of the parameters described above have been well established in enzymology of related proteins. However, one may find that improvement in one parameter (such as thermal stability) results in deterioration of another (such as speed). Therefore, in addition to optimizing major parameters (such as processivity and error rate) individually, sparse-matrix screens of enzymatic function are set up, in which all parameters are varied in large increments, in random combinations (Jancarik J et al., 1991, Journal of Applied Crystallography, 24(4):409-11), often resulting in unexpected combinations of optimal conditions that would never be otherwise determined. When testing stable "roadblocks" to the RT, strong stops in extension by the RT may be observed, once substructures that block the polymerase are identified. If the RT reads through these blocks, it is important to sequence the products carefully (as in the present work on the HCV RNA) to determine whether the RT is jumping over them. It is unlikely that the structure-guided mutations will completely fail to alter the RT activity, as the present deletion mutants of the alpha-loop (FIG. 3) strongly influenced processivity. However, improvements may not be seen. To this end, other group IIC RT enzymes are evaluated, guided by a pipeline for protein discovery (Zhao C et al., 2016, Nature structural & molecular biology, 23(6):558-65), and domains are swapped between them. For all enzymological and biophysical studies, data is obtained in triplicate and subsequent fitting is performed such that coefficients of determination ($R^2$) are >95%.

2. Apply the E.r. RT to Track Linkage of Mutations of Individual HIVs in Patients A processive and accurate E.r. RT is utilized to define HIV population dynamics in the blood before and after patient combination antiretroviral treatment (cART) successes and failures. The WT or optimized E.r. RT is used to quantify individual barcode coverage with unique HIV sequences to track dsDNA processing errors and determine the extent of the error introduction due to PCR resampling and template switching. This strategy allows the fine-tuning of conditions to reduce processing errors. It also provides a baseline to allow comparisons of improved E.r. RTs before analyzing patient samples for cART-mediated mutational changes.

Monitoring genetic changes in individual HIV RNAs within a patient requires sequencing methodology to detect mutations in the 1-2% range (Zhou S et al., 2015, J Virol, 89(16):8540-55; Liang R H et al., 2014, Nucleic Acids Res, 42(12):e98), while providing full-length viral sequence reads to retain genetic linkage of distal mutations. NGS methodologies are ideal for detecting genetic differences of viruses within a swarm, given low sequencing error rates (Zhou S et al., 2015, J Virol, 89(16):8540-55; Liang R H et al., 2014, Nucleic Acids Res, 42(12):e98). However, due to short-sequencing reads of NGS, the linkage between different mutations on a single viral RNA is lost. Alternatively, single molecule sequencing technologies generates very long sequence reads, but a concern is that due to the higher sequencing error rates (Goodwin S et al., 2016, Nat Rev Genet, 17(6):333-51; Quick J et al., 2015, Gigascience, 4:6.) minor viral variants in the population might not be identified. To overcome these issues, the Primer ID methodology (Jabara C B et al., 2011, Proc Natl Acad Sci USA, 108(50): 20166-71; Zhou S et al., 2015, J Virol, 89(16):8540-55), which was originally developed for the sequencing of short HIV RNA fragments, has been modified to obtain synthetic long reads of ~10 kb (Hong L Z et al., 2014, Genome Biol, 15(11):517; Stapleton J A et al., 2016, PLoS One, 11(1): e0147229; Wu N C et al., 2014, PLoS One, 9(5):e97505). The use of unique barcodes allows for computational reassembly of the original viral sequence to determine identity and enrichment of individual RNA species within a population, and for correction of PCR amplification and sequencing errors (Zhou S et al., 2015, J Virol, 89(16):8540-55; Liang R H et al., 2014, Nucleic Acids Res, 42(12):e98). The use of E.r. RTs to provide full-length HIV cDNAs will allow individual, full-length viral sequencing, which is unprecedented.

A. Optimize Full-Length Genomic Coverage of HIV (i). Investigate Barcode Read Distribution and Sequencing Depth Various proviral (DNA) genomes of differing lengths have been utilized, given the inability of current commercial RTs to generate long (>7 kb) and high quality viral cDNAs for sequencing. The read coverage of the 7.2 Kb proviral Human Rhinovirus (HRV) 14 (Lee W M et al., 1993, J Virol, 67(4):2110-22), with 2 additional kb of the pUC19 cloning plasmid, to increase genomic length, was determined. The HRV 14-2 pUC19 proviral genome was produced by overlap extension PCR to incorporate primers, and resulting barcoded proviral product was then used for analysis. After MiSeq sequencing, 15.2M raw reads were filtered. Read alignment relied on previously reported bioinformatic tools (Flynn W F et al., 2015, PLoS Comput Biol. 11(4): e1004249). The 90K average reads per position yielded a ~4-fold coverage depth per genome. In addition to allowing determination of read depth/tagged genome, barcoding also allowed filtering of sequencing errors and/or PCR amplification artifacts (Jabara C B et al., 2011, Proc Natl Acad Sci USA, 108(50):20166-71; Hong L Z et al., 2014, Genome Biol, 15(11):517; Wu N C et al., 2014, PLoS One, 9(5): e97505). Reads were sorted into barcode clusters, each cluster constituting an individual genome with a set number of reads mapping to different regions within that genome. A total of 164,293 barcoded clusters were observed, a value in close agreement to 156,552 HRV 14-2 pUC19 genomes calculated by qPCR at the beginning of the run. This information allows one to design strategies for optimization of sequencing requirements, i.e., number of reads required from a MiSeq Flowcell and amount of input genomes.

Non-HIV proviral genomes were used given that full-length HIV genomes are infectious. NL4-3 and other HIV proviruses are utilized to establish conditions for sequencing of patient HIV. HIV proviruses are sequence verified and are used as reference genomes for sequence assembly. E.r. RT is utilized for generating cDNA from transiently transfected infected cell lines to provide a baseline for evaluating improved versions of E.r. RTs. To simulate patient HIV RNA amounts, 3,000 and 6,000 copies of NL4-3 input and 20, 25, or 30 PCR cycles are evaluated at step 2 during template amplification. It is examined whether an identical run with 6,000 input genomes with 25M reads would generate ≥30 fold sequencing depth for ~40-60% of the genomes analyzed. To test this, an entire MiSeq flowcell, providing 25-30M reads, is used to increase sequence depth per genome/barcode. All analyses utilize the starting (DNA) proviral genome as the sequence reference. Results provide information on barcode vs. sequence coverage and depth of coverage, as well as PCR amplification and sequencing errors.

(ii). Define the Level of Template Switching During PCR Amplification of the HIV dsDNA Mutations can arise during PCR amplification. However, these events are not as frequent given the high fidelity of the commercial DNA enzymes used. The larger concern is template switching during any of the PCR amplification steps in the protocol, which would generate chimeric templates. This potential problem is tested by mixing 2 HIV clones that differ in sequence: NL4-3 Triple (mutations in protease, gag and LTRs), and BAL (mutations in envelope).

NL4-3 and BAL proviral DNAs, 3,000 genomic copies each, are mixed, barcoded by overlap extension PCR, then analyzed. An entire MiSeq flowcell, providing 25M reads, is used to provide sufficient depth and coverage. After sequencing completion, reads are sorted into barcode clusters, each cluster constituting an individual genome with a set number of reads mapping to different regions within that genome for analysis. The number of sequences obtained that are not unique to either NL4-3 or BAL provirus (i.e. chimeric sequences), is used to determine of rate of template switching.

If chimeric sequences occur with a rise in PCR cycle number, cycle number is adjusted so that chimeric sequences decrease to <1% of the error frequency. If chimeric sequences remain when PCR cycles are reduced, it is important to focus on template switching at the library preparation step and adjust PCR cycle numbers. Lastly, the validated protocols allow one to quickly evaluate modified and/or improved E.r. RTs.

B. Optimize E.r. RTs to Generate Full-Length cDNA from Wild Type and cART Resistant HIV Virion RNAs for Sequencing: In Vitro Simulation of an HIV Swarm for E.r. RT Evaluation Studies described herein involve optimizing E.r. RTs for HIV RNA full-length sequencing. The sensitivity of E.r. RT and MinION is determined for detecting drug-resistant HIV mutants in a mixture of wild type HIVs from patients by simulating a patient's HIV swarm for RNA isolation and sequencing. To accomplish this, HIV mixtures are generated from the following proviral HIVs after cell infection: NL4-3 wild type and NL4-3s with the following drug-resistance mutations (Breuer S et al., 2011, Biochemistry, 50(20):4371-

81): 3 mutations in protease, 3 mutations in gag, and triple mutations in protease and gag.

Wild type HIV is mixed with protease, gag, and protease/gag mutant HIVs at the following ratios based on p24 levels: 1) 40% Wild type:20% protease:20% gag:20% protease/gag and 2) 92% Wild type:2% protease:2% gag:2% protease/gag. 6,000 and 10,000 viral copies (based on p24) are extracted. E.r. RT is used for cDNA generation, and products run through the workflow and sequenced using a MiSeq flowcell (providing 25M reads) and the MinION. For nanopore (MinION) sequencing, it is important to initially rely on the manufacturer's protocol. Barcode read and sequence coverage is deconvoluted, and alignments are based on proviral sequences to determine coverage and error rates. MinION sequencing output may rely on reassembly.

NGS generally resolves viral mutations at 1-2% frequency. The use of 2 samples containing differing amounts of wild type to mutant HIVs enables the resolving power of the protocol for identifying coverage and depth of coverage for full-length mutant viral sequences to be determined. Further, each mutant virus is 2% or 20% of total viral RNA, which allows the sensitivity to be established, and the sequence number of full-length mutant virus, as well as error rates to be determined. These outcomes are informing the decision as to whether increased sampling depth and the use of the NextSeq platform is needed. Given that product amounts are quantified at each step in the workflow, the conversion rate from viral RNA to cDNA is determined. Comparisons of the sequence output and ability to identify viral mutants in mixtures by MinION methodologies (with barcoding of products for tracking errors and viral species identification) provides important benchmarks for coverage, depth of coverage, and error rates for the field.

C. Define HIV Population Dynamics in the Blood Before and after Patient Combination Antiretroviral Treatment (cART) Successes and Failures The covariation of HIV mutations in protease and gag from patient samples after 1 or 2 cART failures has been reported (Flynn W F et al., 2015, PLoS Comput Biol. 11(4):e1004249). However, the studies did not address the presence of preexisting HIV variants in patients before treatment that may have been selected or recombined during cART to give rise to cART resistant viruses. Furthermore, given the absence of RTs capable of providing HIV RNA long-reads, the sequencing studies relied on short reads, thus removing any genetic linkage between protease and gag from individual viruses as well as other distal viral genes necessary for drug resistance and fitness. With the development of E.r. RTs, it is possible to obtain long-reads from HIV RNAs and follow individual genetic changes within the viral swarm before and during cART.

Sequential sera/plasma samples from 30 HIV-infected patients collected before and after cART are analyzed for viral changes; 30 samples available before cART, 30 samples after the 1st cART failure (all failed) and 15 after 2nd cART (15 suppressed virus and 15 failed). Treatments contained a single protease inhibitor (PI) and combinations of nucleoside and non-nucleoside reverse transcriptase inhibitors. cART failure is defined as >50 copies/mL at testing. Upon failure, new PIs were used. For sequencing purposes, samples >1000 viral copies/mL, with the average ~6,000 copies/mL, are used, as reported (Flynn W F et al., 2015, PLoS Comput Biol. 11(4):e1004249). Viral RNA are prepared for use as previously reported (Chang M W et al., 2013, J Virol Methods, 189(1):232-4).

E.r. RT optimized as discussed herein, is used to generate cDNA from samples. Using ≥6,000 HIV genomes is useful for the E.r. RT step, as this allows sufficient representation for sampling and sequencing depth. However, the amount of viral RNA to be used depends on findings from the E.r. RT studies, to determine the amount of dsDNA required to ensure sequencing coverage. All samples are sequenced twice (75 samples x2=150 samples, which is 50 samples/year) to ensure reproducibility of less abundant variants. Mutations and sequences not confirmed in both sequencing runs are discarded. The relationship of HIV mutations arising over time during cART and relied on mutual information theory to infer the association of protease and gag mutations has been reported (Flynn W F et al., 2015, PLoS Comput Biol. 11(4):e1004249). This method was required given the loss of physical linkage among HIV mutations due to short reads imposed by the NGS method performed (Flynn W F et al., 2015, PLoS Comput Biol. 11(4): e1004249). Physical linkage of distal viral mutations is maintained, allowing assessment of mutational/viral gene covariation by measuring linkage disequilibrium (LD) (Routh A et al., 2015, Methods, 91:40-7). Co-Variation Mapper is utilized to test for LD (Routh A et al., 2015, Methods, 91:40-7); it has been shown that NGS data can be searched for evidence of covariation by measuring LD within the viral mutational landscape.

Full-length HIV RNA is sequenced in considerable depth (>30× coverage) from samples collected over time before and after cART, allowing one to define the linkage of distal mutations and viral genes contributing to viral resistance and fitness, which is without precedent at the current time. The findings are compared to published studies where NGS was used to computationally define interactions of protease and gag mutations (sequences reads were not linked) in supporting or reducing resistance (Flynn W F et al., 2015, PLoS Comput Biol. 11(4):e1004249). It is possible to determine whether viruses present before treatment and/or recombination contribute to cART resistance.

It is expected that the optimized E.r. RT reads through the ~9 kb HIV RNA transcript. However, the strategy may be modified, and sequence-specific primers utilized to obtain HIV RNA cDNA by dividing the virus into two overlapping ~5 kb parts, and thereby utilizing E.r. RT to obtain longer cDNAs than could be obtained from current MLV RTs. Sequence-specific primers for HIV sequencing have been employed in the past (Flynn W F et al., 2015, PLoS Comput Biol. 11(4):e1004249). For all molecular biological, human, and sequencing studies, when appropriate, study designs are employed to obtain data in triplicate and with coefficient of variance ($R^2$)>95%.

3. Use the Optimized RT to Study the Tissue-Specific Linkage Between Patterns of Alternative-Splicing in *Drosophila*

The procedures outlined above are geared towards developing improved versions of the E.r. RT and developing reaction conditions that facilitate quantitative and accurate reverse transcription of long, structured RNA molecules. In addition to these pursuits, the use of the E.r. RT is optimized to generate full-length cDNA libraries from known, but complex mixtures of RNA molecules and then assess the efficiency of full-length cDNA synthesis by nanopore sequencing and once optimized, to use this approach to perform whole-transcriptome sequencing of a select number of *Drosophila* tissues.

A. Optimize the Use of the E.r. RT to Generate and Sequence Full-Length cDNA Libraries One of the greatest challenges of performing full-length cDNA sequencing is that reverse transcriptases have limited processivity and therefore tremendous difficulty in traversing the complete length of mRNAs. Nanopore sequencing was previously used to characterize full-length cDNA sequencing (Bolisetty M T et al., 2015, Genome Biol, 16:204). These efforts have demonstrated the feasibility of this approach and, at the same time, clearly highlighted the need for developing robust, processive reverse transcriptases.

The sequencing of 'full-length' Dscaml cDNAs was pioneered on the Oxford Nanopore MinION™ (Bolisetty MT et al., 2015, Genome Biol, 16:204). In this context, 'full-length' indicates the region of Dscaml from exon 3 to exon 10, which contains 95 of the 115 exons that can be spliced in 19,008 different patterns. In these experiments, SuperScript® II (SSII) was used to reverse transcribe either a Dscaml spike-in RNA pool or total RNA isolated from *Drosophila* heads. The low processivity of SSII was overcome by PCR amplifying 'full-length' Dscaml cDNAs using primers in the flanking constitutive exons (exon 3 and exon 10). The amplified Dscaml cDNAs were then end-repaired, dA-tailed, and ligated to adapters. The cDNAs were then sequenced on an R7.3 MinION™ for 9 hours obtaining 159,948 reads, with reads as long as 2 kb. Using LAST (Kielbasa SM et al., 2011, Genome Res, 21(3):487-93), 28,971 reads could be uniquely aligned to only one variant in each cluster, corresponding to 7,874 distinct isoforms. The two direction (2D) reads, reads where both strands were sequenced, aligned with an average of 92% identity across the length of the isoforms. Using a set of in vitro transcribed isoforms, template-switching was observed at a frequency of less than 0.1%, resolving a problem that plagued previous approaches to sequence Dscaml isoforms that were developed (Roy CK et al., 2015, Elife, 4; Sun W et al., 2013, EMBO J, 32(14):2029-38.).

RT-PCR amplification has since been utilized using primers in the first and last constitutive exons of 12 other ultracomplex *Drosophila* genes (Brown J B et al., 2014, Nature, 512(7515):393-9) and the expression of hundreds of isoforms from each gene has been verified. Although the approach of amplifying individual genes using primers in the outermost constitutive exons works, it only does for genes that have only a single first and last exon. However, many—in fact most—genes have either alternative first or last exons and cannot be studied in this manner. Moreover, it is not feasible to perform these types of experiments on a transcriptome-wide scale.

Several commercial reverse transcriptases have been used to determine the extent to which they are able to synthesize full-length cDNAs. After performing cDNA synthesis with these enzymes using the manufacturer's recommended conditions, libraries were prepared and sequenced on a MinION™. The RNA samples used for these experiments are Spike-in RNA Variant Control Mixes (SIRVs) (Lexogen). These are pools of 69 high-quality, artificial transcript variants which mimic 7 human model genes, each of which contains multiple isoforms. The SIRV RNAs span different sizes, splicing patterns, GC contents and strands. Moreover, there are three different pools of SIRV RNA in which the various transcripts are mixed together in different ratios—either equimolar, or spanning one or two orders of magnitude. These synthetic spike-in RNAs therefore provide the opportunity to easily assess the quality of library preparation and sequencing, and in this case, the efficiency of reverse transcription. There is a desperate need for a robust and processive reverse transcriptase to be used for the preparation of full-length cDNA sequencing libraries.

The E.r. RT variants and reaction conditions developed herein are utilized and applied to the preparation of full-length cDNA libraries that are assessed by nanopore sequencing. The initial RNA samples used may be the synthetic SIRV RNA pools from Lexogen™. The well-defined, yet complex nature of these synthetic RNA pools allows the assessment of the extent of full-length cDNA synthesis. After preparing and sequencing the cDNAs using the standard Oxford Nanopore Technologies™ protocols, the reads are aligned to the SIRV reference RNA sequencing using LAST (Kielbasa SM et al., 2011, Genome Res, 21(3):487-93) to assign each read to a specific SIRV isoform. For each transcript, the extent of full-length cDNA synthesis is calculated by dividing the number of reads that span the entire length of the transcript by the total number of reads that map specifically to that transcript. Since the SIRV transcripts have different lengths, GC contents, and secondary structures, calculating these values for each transcript allows the monitoring of how each of these characteristics impacts the ability of the E.r. RT to faithfully copy RNA.

For these experiments, cDNA libraries are prepared using several E.r. RT variants and reaction conditions in parallel, and then using barcoded adapters to mark the individual libraries with a molecular tag. This enables each library to be sequenced individually, or the performance of multiplexed sequencing depending on the number of reads needed per library and the throughput of the nanopore sequencer. For the initial experiments, a SIRV pool is used, in which all RNAs are present in equimolar concentrations. Given that the SIRV pools contain only 69 transcripts, the use of this pool allows one to obtain >70X coverage of each transcript by obtaining 5,000 reads per library. Using the R7.3 version of the MinION™, it is possible to obtain 25,000 reads in a 10 hour sequencing run, which allows the multiplexing of up to five libraries in a run. However, the current version of the MinION™ uses a R9 flowcell, which has at least a 5-fold higher throughput allowing for more substantial multiplexing.

The experiments using the SIRV RNAs are an excellent way to monitor both processivity and accuracy of the E.r. RT. These results are complemented by the template switching assays outlined above, and the error rate determination assays outlined above, to fully characterize the performance of the E.r. RT.

B. Use E.r. RT Library Preparation Method to Perform Transcriptome Sequencing of *Drosophila* Tissues Transcriptome profiling experiments previously performed as part of the modENCODE project revealed that brain, testis and ovaries express the greatest diversity of isoforms of all *Drosophila* tissues (Brown J B et al., 2014, Nature, 512(7515):393-9). Therefore, nanopore sequencing of full-length cDNAs synthesized by the E.r. RT and other commercial RTs from RNA isolated from brain, testis and ovaries is performed. Furthermore, the data from these long-read libraries is compared to more traditional short-read sequence libraries. First, the long-read libraries is generated using remaining aliquots of the same RNA samples previously used for the modENCODE project in which billions of short reads were generated using the Illumina TruSeq library preparation kits. This allows the vast amount of short-read RNA-seq data previously generated from these samples to be used to directly compare to the long-read E.r. RT-based libraries that is prepared and sequenced as described herein. In addition, short read libraries from these same RNA samples using the E.r. RT and other commercial RTs instead of SuperScript are generated and sequenced on the Illumina platform. In this way both short and long-read transcriptome data are compared using the E.r. and other commercial RTs.

The optimal E.r. RT variant(s) and reaction condition(s) identified herein are used to generate cDNA libraries from brain, testis and ovary RNA samples and these libraries are sequenced using either the Oxford Nanopore MinION™ or PromethION™, depending on the depth required and the throughput of each device. The PacBio™ programs ICE and quiver are adapted to perform isoform level clustering and consensus sequence polishing. The resulting consensus reads are aligned to the *Drosophila* transcriptome using LAST (Kielbasa SM et al., 2011, Genome Res, 21(3):487-93). Reads that fully align to an annotated isoform are retained while those that do not are realigned to the *Drosophila* genome to identify and deconvolute novel isoforms. From these data, the percent inclusion of each cassette exon is calculated and this compared to the percent inclusion observed in the corresponding Illumina™ short read data. Together, these experiments are resulting in an optimized protocol for generating full-length cDNA sequencing libraries, which is significantly advancing the ability to accurately interrogate transcriptomes of all living organisms.

Some further optimization of the E.r. RT for use in these complex RNA samples may be necessary. In addition, whole transcriptome sequencing will require much more depth than the simpler RNA samples used earlier. Nonetheless, with the recent throughput increases of the Oxford Nanopore Technologies™ sequencers and the availability of a PromethION™, the depth necessary to perform deep transcriptome sequencing on this platform is obtained, and therefore the efficiency of the E.r. RT is tested in a real-world use case. For all RNA sequencing experiments, data are obtained in triplicate and have pairwise correlations of $R^2 > 0.9$ at the isoform level.

Example 2: Maturase from E.r. Group II Intron is a Highly Processive and Accurate Reverse Transcriptase Group II introns encode maturase proteins that function as reverse transcriptases (RTs). These reverse transcriptases are highly processive and accurate, as such properties are required for survival of group II introns inside their hosts. However, a critical understanding of the structural elements that determine the RT processivity of group II intron maturases is lacking, as their structural information has been obscured. Described herein is the characterization of RT processivity of group II intron maturase from *Eubacterium rectale* (E.r.), which has available high-resolution structural information for its N-terminal RT domain. It was found that E.r. maturase has a superior intrinsic RT processivity compared to commercial Superscript IV (SSIV). This high processivity allows E.r. matuarase to substantially out-perform SSIV on a 9.6 kb HCV genome. Such high intrinsic processivity of E.r. maturase is dependent, in part, on a loop structure (α-loop) in the finger subdomain that may act as a steric guard. The positively-charged RNA binding surface on the RT domain has no contribution to RT processivity. Additionally, reducing its positive charge increases the active fraction of E.r. maturase on a difficult template, potentially by reducing enzyme depletion through non-specific RNA binding. Finally, single-molecule sequencing estimated that the error rate of E.r. maturase is comparable to the error rate from SSIV. These results not only provide a structural mechanism for the high processivity of group II intron maturase and related non-LTR RTs, but also demonstrate that engineering E.r. maturase has created a powerful tool RT enzyme.

In the experiments presented herein, RT processivity of maturase from *Eubacterium rectale* (E.r.) was characterized. E.r. maturase had higher intrinsic processivity than commercial Superscript IV (SSIV), and it produced more full-length cDNA products from a 9.6 kb HCV genome. Such high processivity may be at least partially attributed to a loop structure (α-loop) in the finger subdomain that is unique to group II intron maturases and non-LTR RTs. Deletion of this α-loop leads to a complete loss of processivity and transformed the E.r. maturase from a processive polymerase to a distributive polymerase. In addition, engineering mutations of the positive charges on the surface that interacts with group II intron RNA in the context of maturase-intron holoenzyme does not affect RT processivity. In fact, reducing those positive charges increased the primer incorporation rate on a difficult RT template, potentially by increasing the active enzyme fraction that would be otherwise depleted through non-specific RNA binding. Finally, error rate estimated by single-molecule sequencing showed that E.r. maturase is at least as accurate as commercial SSIV. The results presented in this example provide insights that reveal the structural mechanism of the superior RT processivity of group II intron maturases and non-LTR RTs. Additionally, these results lay the foundation for additional engineering of E.r. maturase into a more highly processive, specific and accurate tool reverse transcriptase. Further detail regarding the experiments presented here can be found in Zhao et al., 2018, RNA, 24: 183-195, which is incorporated by reference herein in its entirety.

The materials and methods employed in these experiments are now described.

Construct Description, Protein Expression and Purification

The protein sequence for wild-type (WT) E.r. maturase (from group IIC intron Eu.re.I2) was obtained from group II intron database (Candales MA et al., 2012, Nucleic Acids Res, 40:D187-190), and the codon-optimized cDNA was synthesized by Invitrogen (Thermo Fisher). All mutation constructs were generated by Q5 site-directed mutagenesis kit (NEB). Construct mut1 has 4 point mutations including R58A, K59A, K61A and K163A. Construct mut2 has 2 point mutations including K216A and R217A. Construct mut1+ mut2 has 6 point mutations that is a combination of mut1 and mut2. Construct mut3 is a triple mutant that consists of K338A, K342A, and R353A. Construct Aloop has replaced resides 182-192 with two glycines.

Protein expression and purification were performed according to a protocol published previously (Zhao C et al., 2016, Nat Struct Mol Biol, 23:558-565). In brief, E.r. maturase was expressed with an N-terminal 6xHis-SUMO fusion tag in *E. coli*. (Rosetta™2 DE3), and was initially purified by Ni-NTA affinity column (Qiagen™). The fusion protein was then eluted from Ni-NTA resin by a buffer containing 300 mM Imidazole, and the fusion tag was cleaved by yeast Ulp1 at 4° C. for 1 hour. The precipitated protein after tag cleavage was spun down and the supernatant was directly loaded onto a 5 mL Hitrap® SP column (GE Healthcare™) equilibrated with a buffer containing 300 mM KCl at pH 7.5 (low salt buffer). Under this condition, Ulp1 does not bind the SP column. The Hitrap® SP was used instead of the Hitrap Heparin column, as described in the previous protocol, because the SP column gives better resolution for some maturase mutants. For WT, mut1, mut2, and mut 3 E.r. maturase constructs, the bound proteins were initially directly eluted by a buffer containing 2 M KCl at pH 7.5 (high salt buffer). The 5 mL peak fraction was diluted to 70 mL with low salt buffer, and was then loaded onto Hitrap® SP equilibrated with a mixture of 72% low salt buffer and 8% high salt buffer. The bound protein was eluted with a linear salt gradient that reaches 50% high salt buffer after 50 mL elution (starting from 8% high salt). For mut1+mut2 construct, after loading the supernatant after clarifying the SUMO tag-cleavage reaction, the protein was eluted with a linear salt gradient that reaches 50% high salt buffer after 50 mL elution (starting from 0% high salt). For all constructs, the proteins after Hitrap® SP were finally purified by a Superdex® 5200 Increase column (10/300 GL, GE Healthcare™), and the peak fraction was pooled, concentrated to 2-20 mg/mL, and flash-frozen under liquid nitrogen.

Processivity Assay (Single-Turnover)

RepA D3 (residues 998-1630) (Liu F et al., 2017, Nat Chem Biol, 13:282-289) was used as RNA template for single-turnover processivity assay, and the RT primer used in this assay annealed the very 3' end of RNA template (Table 1).

TABLE 1

Primer sequences used for RT assays.

| RNA template | Annealing position | Sequence |
| --- | --- | --- |
| RepA D1 | 387 | 5' ACCATATTTCCATCCACCAAG CGC 3' (SEQ ID NO:1) |
| RepA D3 | 1630 | 5' TAATAGGTGAGGTTTCAATG 3' (SEQ ID NO: 2) |
| HCV genome | 4940 | 5' GTCTCCGCTGGTGTGAG 3' (SEQ ID NO: 3) |
| HCV genome | 9461 | 5' AAGGAACAGTTAGCTATGGAG TG 3' (SEQ ID NO: 4) |

Annealing position is the nucleotide number on RNA template that anneals to the very 5' end of the primers.

The RT primer was 5' end labeled by $^{32}$P by T4 PNK, and the labeled primer was purified by 20% polyacrylamide gel. In this assay, the RNA template was first diluted to 40 nM (10× stock) in RNA storage buffer containing 10 mM K-MES (pH 6.0) and 1 mM EDTA. The RNA template was then mixed with 40 nM (10× stock) primer at 1:1 volume ratio, and the mixture was heated at 95° C. for 1 minute and was then snapped cool on ice for 10 minutes. Then the annealed template-primer was incubated with RT enzymes in RT reaction buffer according to the following recipe. For E.r. maturase constructs, 2 μL template-primer mixture was combined with 5 μL H$_2$O and 1 μL 10× RT reaction buffer (500 mM K-HEPES pH 7.5, 1 M KCl, 20 mM MgCl$_2$, 100 mM DTT), and was then mixed with 1 μL E.r. maturase at 50 nM. For SSIV and TGIRT, 2 μL template-primer mixture was combined with 1 μL H2O, 1 μL DTT (100 mM), 2 μL 5× RT reaction buffer (commercial), and was then mixed with 1 μL enzyme at 50 nM. The incubation was performed at room temperature for 20 minutes, after which the RT reaction was initiated by adding a 3 μL solution containing 1 μL of 50 μg poly(rA) (GE Healthcare) annealed to 1 μL of 100 μM dT50 (trap) and 1 μL of 5 mM dNTPs. The RT reaction was performed for 10 minutes at 42° C. for E.r. maturase constructs, 55° C. for SSIV and 60° C. for TGIRT. The RT reaction was stopped by heating up the samples at 95° C. for 1 minute to denature the enzymes. The enzymes were then digested by adding 1 μL protease K at 30 mg/mL into the 10 μL RT reaction and incubated at 37° C. for 10 minutes. Then the RNA template was hydrolyzed by adding 1 μL 3 M NaOH into the reaction mixture followed by incubating at 95° C. for 5 minutes. The RNA sample was then directly mixed with Urea loading dye and the first-strand cDNA products were resolved on a 10% polyacrylamide sequencing gel. For control group, similar procedure was followed except that trap (1 μL of 50 μg poly(rA) annealed to 1 μL of 100 μM dT50) was included in the pre-incubation step for annealed template-primer and RT enzymes. The intensity profiles for the gel lanes were extracted by software ImageQuant TL (GE Healthcare). Pixel positions were converted to DNA length by interpolating the linear regression of the logarithm of bands in single-stranded (ss) DNA ladder (Simplex) against pixel position. The median of every reaction lane was calculated. All plots were produced by software Prism (GraphPad, version 7.01).

Multi-Turnover RT Assay

In multi-turnover RT assays, RepA D1 (residues 1-419), RepA D3 (residues 998-1630) (Liu F et al., 2017, Nat Chem Biol, 13:282-289) and HCV genome (strain Jc1) (Pirakitikulr N et al., 2016, Mol Cell, 62:111-120) were used as RNA templates. The primer for RepA D1 annealed to position 387, the primer for RepA D3 annealed to position 1630 (very 3' end), and primers for HCV genome annealed to positions 4940 and 9461 (Table 1). The RT primer was 5' end labeled by $^{32}$P by T4 PNK, and the labeled primer was purified by 20% polyacrylamide gel. In the multi-turnover assays, the final RNA template concentration was 100 nM and the final enzyme concentration was 500 nM. The RT reactions were set up in the same buffer conditions and temperatures for each enzyme as have been used in single-turnover processivity assays, and no traps were added into the reaction mixture. The reactions were allowed to proceed for 10 minutes for RepA D1 and D3 templates, and for 1 hour for HCV genome. The enzymes were then digested by protease K, and the RNA templates were hydrolyzed by NaOH, as described above.

The first-strand cDNA products synthesized from RepA D1 and D3 templates were resolved by a 10% polyacrylamide sequencing gel along with ssDNA ladder (Simplex). The first-strand cDNA products synthesized from HCV genome were resolved by a 0.8% (w/v) alkaline agarose gel according to the protocol published previously (Sambrook J et al., 2006, CSH Protoc, 2006(1)). In brief, SeaKem LE agarose was first dissolved in H$_2$O by microwaving 2-3 minutes. After the solution cooled down to 50-55° C., 10× alkaline gel running buffer (500 mM NaOH and 1 mM EDTA) was added to agarose solution before casting the gel. The gel was run in 1× alkaline gel running buffer at room temperature for 5 hours at 2 V/cm. The gel was then transferred onto a Hybond-N+ nylon membrane (GE Healthcare) that was placed on top of 2 layers of Whatman paper, after which the gel was covered by Saran wrap. To avoid gel cracking, the gel was first dried at 80° C. for 1 hour under vacuum, and was then allowed to slowly cool down to room temperature under the vacuum for 1 hour. The ladder used in alkaline agarose gel was the 1 kb double-stranded (ds) DNA ladder (NEB), which was denatured under alkaline gel-electrophoresis condition.

Error Rate Determination

RepA D3 (residues 998-1630) was used as the RNA template for error rate estimation, and the RT primer anneals to position 400. 5' to the annealing site, the RT primer has 15 nucleotides (nts) random sequence (unique molecular identifier, or UMI), which was followed by a 4-nt condition barcode and a region complementary to Illumina universal primer that is at the very 5' end (FIG. 8A and Table 2).

TABLE 2

Primer sequences used for error rate determination.

| | RT |
|---|---|
| 2nd strand RT | CTACACGACGCTCTTCCGATCTCTGTNNNNNNNNNNNNNNN NGATTATAGGACATTTAGGTCGTAC (SEQ ID NO: 5) <u>CAGACGTGTGCTCTTCCGATC</u>GGTANNNNNNNNNNNNNNN ACATTTCTAACTGGAAGTCAAGC (SEQ ID NO: 6) |

| | PCR amplification |
|---|---|
| forward | CTACACGACGCTCTTCCGATCT (SEQ ID NO: 7) |
| reverse | <u>CAGACGTGTGCTCTTCCGATC</u> (SEQ ID NO 8) |

| | Sequencing adaptors |
|---|---|
| index2 | CAAGCAGAAGACGGCATACGAGAT*ACAT*CGGTGACTGGAG TTCAGACGTGTGCTCTTCCGATCT (SEQ ID NO: 9) |
| index4 | CAAGCAGAAGACGGCATACGAGAT*TGGT*CAGTGACTGGAG TTCAGACGTGTGCTCTTCCGATCT (SEQ ID NO: 10) |
| index5 | CAAGCAGAAGACGGCATACGAGAT*ACAG*TGGTGACTGGAG TTCAGACGTGTGCTCTTCCGATCT (SEQ ID NO: 11) |
| index7 | CAAGCAGAAGACGGCATACGAGAT*CAGA*TCGTGACTGGAG TTCAGACGTGTGCTCTTCCGATCT (SEQ ID NO:12) |
| universal | AATGATACGGCGACCACCGAGATCTACACTCTTTCCCTAC ACGAC<u>GCTCTTCCGATC</u> (SEQ ID NO: 13) |

N indicates random nucleotide, and the string of 15 Ns is the product barcode (UMI).
Italicized sequences in SEQ ID NO: 5 and SEQ ID NO: 6 indicates condition barcode.
Bold and underlined regions indicate complementary sequences for PCR amplification.
Italicized sequences in SEQ ID NO: 9-SEQ ID NO: 12 indicate Illumina index.

The primer used for second-strand synthesis has a similar configuration, which contains a region complementary to Illumina™ Index primer at the very 5' end, followed by a 3-nt condition barcode and region that is complementary to the very 3' end of first-strand cDNA (FIG. 8A and Table 2). In principle, the condition barcode was designed to sort different reaction conditions, and partially resolves library low-diversity problem by having condition barcode with different lengths. However, in this study, the same condition barcode was used for all enzymes, and different enzymes were barcoded by Illumina™ indexes.

The RT reaction was set up in a 20 μL volume with 0.2 pmole RNA template (1.2 X $10^{11}$ molecules) annealed to 0.2 pmole RT primer, which is much less than the number of molecules that can be encoded by combined UMIs from both primers (15 nts each, $4^{30}=1.15\times10^{18}$). The RT reactions were performed in similar conditions as described in multi-turnover RT assay, except that the reaction time was 1 hour. The reaction was stopped by heating up at 95° C. for 3 minutes, and the reaction mixture was cooled down slowly to allow efficient annealing of first-strand cDNA to the RNA template. The RNA template was then digested by adding 1 μL Ribonuclease H (RNase H;NEB) directly into the reaction mixture followed by incubation at 37° C. for 30 minutes. Then the 20 μL RT reactions were mixed with 0.2 pmole 2nd strand synthesis primer (Table 2), and the 2nd strand cDNA was synthesized by high-fidelity Q5 (NEB) in a 50 μL reaction volume in a thermal cycler for a single cycle (denature at 98° C. for 20 seconds, anneal at 50° C. for 30 seconds and extend at 72° C. for 20 minutes). Then the 50 μL double-stranded (ds) cDNA products were purified by 90 μL AMPure™ XP beads (Beckman) according to manufacturer's protocol. The ds-cDNAs were eluted in 30 μL H₂O, and their concentration was estimated by qPCR using Light-Cycler® SYBR® Green I Master kit (Roche) using plasmid DNA as standard. The ds-cDNAs were then adjusted to the same concentration ($5\times10^{15}$ M) in different groups, and 1 μL dsDNA ($3\times10^9$ molecules) were first amplified by PCR amplification primers (Table 2) for 13 cycles in 25 μL PCR reactions. The PCR products were then purified by 45 μL AMPure™ XP beads (Beckman) and eluted in 15 μL H₂O. 1 μL of the cleaned-up PCR products were further amplified in 25 μL PCR reactions for 10 more PCR cycles using Illumina™ universal primer and Illumina™ index primers (NEBNext®). For all PCR amplification steps, the PCR program is first denaturing at 98° C. for 5 minutes, then amplifying using 3-step protocol with desired cycle numbers (denature at 98° C. for 20 seconds, anneal at 64° C. for 30 seconds and extend at 72° C. for 30 seconds), and finally extend at 72° C. for 5 minutes. The specificity of PCR reactions was confirmed by an agarose gel stained by PicoGreen® (Invitrogen™). Finally, the PCR-amplified products were pooled, and samples were sequenced on an Illumina™ Miseg™ sequencer in pair-end mode for 250 cycles (PE250) with 30% PhiX spike-in. The sequencing data were processed by scripts published earlier (Lee DF et al., 2016, Nucleic Acids Res, 44:e118). In brief, primer binding region and low-quality residues at both ends (100 residues in R1 and 150 residues in R2) were first trimmed, and sequencing reads that have residue with a Q-score lower than 20 were discarded. The sequencing reads were then sorted based on the UMIs at both 5' end and 3' end, and reads that share the same UMIs were counted as a unique product. Reads were aligned to reference sequence by MUSCLE (Edgar RC, 2004. BMC Bioinformatics, 5:113; Edgar RC, 2004. Nucleic Acids Res, 32:1792-1797), and errors were recorded only when the same substitutional mutation or insertion-deletions (indels) were observed in all reads that belong to the same unique product. Finally, only RT products with UMI that appears no less than 3 times were used in estimating substitutional frequency.

The results of the experiments are now described.

E.r. Maturase is Highly Processive

The processivity of a polymerase describes the tendency of the polymerase to stay in the elongation mode and can be defined as the number of nucleotides incorporated during a single template-binding event (Bloom L B et al., 2001, Nature Structural Biology, 8:829-831). Therefore, to measure the processivity of a RT under the most rigorous conditions, one must examine the distribution of RT product lengths under single-turnover conditions, in which the enzyme will not re-associate and initiate another round of RT reaction after it disassociates from RNA template. One method to achieve this single-turnover condition is to add excess RNA-DNA duplex upon initiation of the RT reaction, which traps and prevents rebinding of any disassociated enzyme. To measure the processivity of E.r. maturase and compare it with the processivity of other RTs, the domain 3 (D3) of lncRNA RepA (643 nt) was chosen as RT template (Liu F et al., 2017, Nat Chem Biol, 13:282-289), as it allows efficient RT reaction for a variety of RT enzymes. A trap concentration was then identified that is sufficient to prevent enzyme turnover given a certain template concentration and reaction time. Under this condition, no RT reaction is expected to occur when enzyme was pre-incubated with trap. Using this approach, a single-turnover condition was identified that is similar as what has been reported for M-MLV RT (Baranauskas A et al., 2012, Protein Eng Des Sel, 25:657-668).

Under single-turnover condition, E.r. maturase has superior processivity compared to SSIV. As shown in the gel (FIG. 5A) and the intensity distribution in each lane (FIG. 5B), E.r. maturase has only one minor RT stop at about 40 nt, whereas SSIV tends to stop at various locations throughout the template. Surprisingly, another group II intron maturase TGIRT produced no full-length product under its optimal RT concentration, suggesting that the enzyme is so inefficient or non-processive that the amount of full-length product synthesized is below the detection limit (FIG. 5A).

The high intrinsic processivity of E.r. maturase makes it highly efficient on long and structured RNA templates, such as the 9.6 kb HCV genome (Pirakitikulr N et al., 2016, Mol Cell, 62:111-120). As shown in the gel and intensity profile in every gel lane (FIG. 2A and FIG. 2B), E.r. maturase had much fewer RT stops and produced much more full-length first-stand cDNAs than SSIV for primer that annealed to position 4940 nt (primer-4940) on the HCV genome (FIG. 2A and FIG. 2B). Quantification shows that for all the cDNA products produced by the three enzymes, 93% is full-length product in the case of E.r. maturase, whereas this number is 46% for SSIV and 83% for TGIRT.

Structural Determinants of High RT Processivity

Structural elements that contribute to the high intrinsic processivity of E.r. maturase were identified. This study was facilitated by recently published maturase structures (Qu G et al., 2016, Nat Struct Mol Biol, 23:549-557; Zhao C et al., 2016, Nat Struct Mol Biol, 23:558-565), which provide high resolution information of the finger and palm subdomains of E.r. maturase, and allows homology modeling of its thumb (FIG. 4B).

From a kinetics point of view, polymerase processivity should be considered at each nucleotide during a RT reaction, and it results from the competing forces that either drive the polymerase translocating forward on the RNA template and catalyzing the addition of an extra DNA nucleotide, or lead to backward translocation or polymerase disassociation from the template (McClure W R et al., 1980, Methods Enzymol, 64:277-297). As backward translocation is generally not observed in a normal polymerase reaction (Yin Y W et al., 2004, Cell, 116:393-404; Bar-Nahum G et al., 2005, Cell, 120:183-193; Yu J et al., 2012, Biophys J, 102:532-541), the likelihood of polymerase disassociation is the major factor that determines the processivity of a polymerase. In this sense, the structural determinants of high RT processivity should be the structure features that interact with RNA template to prevent dissociation. For most reverse transcriptases, the β-hairpin in the finger subdomain, and the thumb subdomain, enclose the RT active site and prevent RNA template from falling off (FIG. 4B and FIG. 6A). For example, in HIV RT, extending the β-hairpin by 15 amino acids improved RT processivity (Kew Y et al., 1998, J Biol Chem, 273:7529-7537).

Figure 6B:
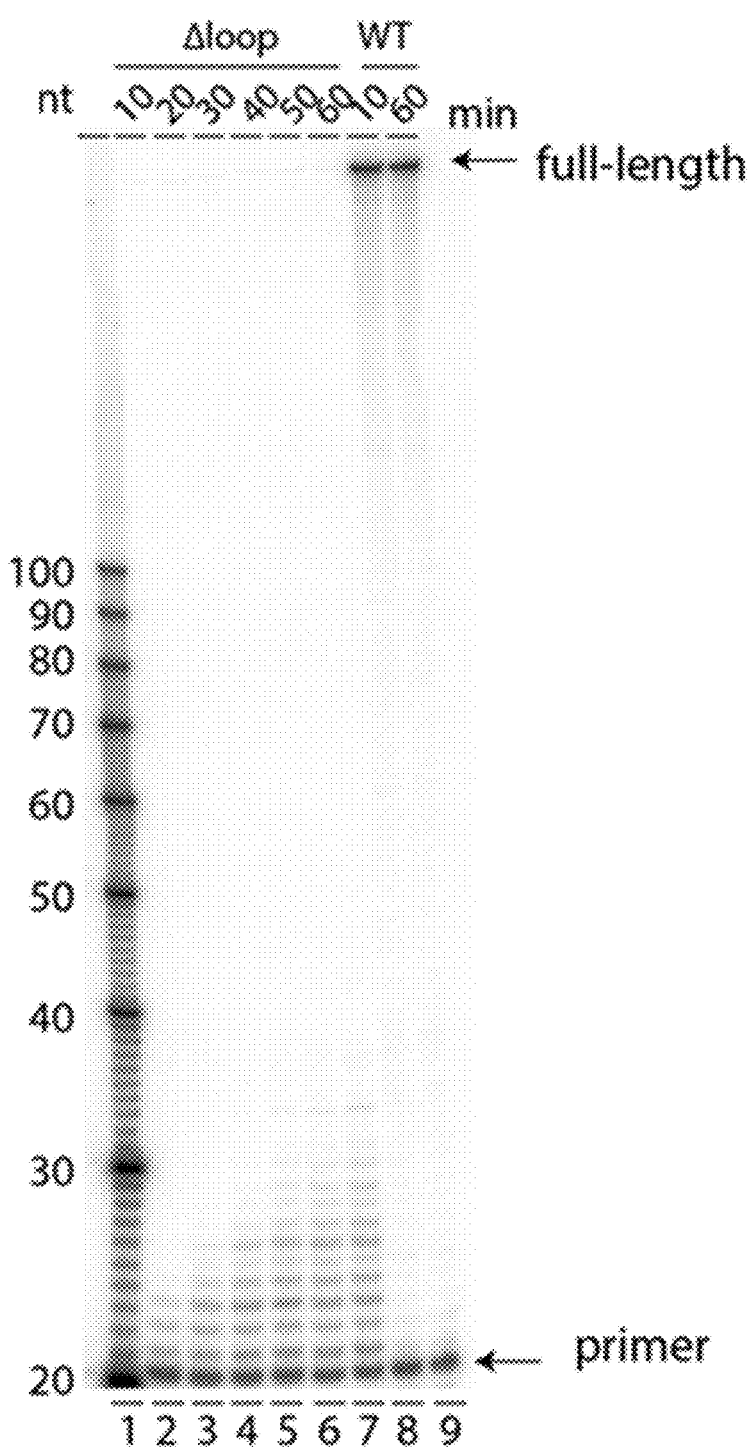

Interestingly, in addition to the conventional processivity elements mentioned above, a novel loop structure (α-loop) that is unique to group II intron maturases is observed in the finger subdomain of E.r. maturase. This loop is located right next to the β-hairpin and encloses the active site (FIG. 6A). Deletion of this α-loop resulted in a complete loss of processivity even under multi-turnover condition (FIG. 6B). Additionally, the median length of RT products (macroscopic processivity) for the Δloop mutant increased substantially over time, which is in sharp contrast to the wild-type maturase that established a stable distribution of products within 10 minutes (FIG. 6B). This behavior of the Δ-loop mutant is consistent with a distributive polymerase, which falls off the RNA template very frequently or even after every nucleotide addition event. Therefore, this α-loop is a unique processivity factor in E.r. maturase, and based on sequence alignment (FIG. 6A), this loop is also very likely present and potentially plays a similar role in other group II intron maturases and the closely related non-LTR RTs.

Structural Elements that are Irrelevant to RT Reactivity

It was then asked whether all regions in E.r. maturase are important for its RT processivity and RT activity in general. This is because maturase is a multi-functional protein that could also recognize and stabilize its host group II intron RNA (FIG. 7A) and promote intron splicing (Matsuura M et al., 1997, Genes Dev, 11:2910-2924; Wank H et al., 1999, Mol Cell, 4:239-250; Qu G et al., 2016, Nat Struct Mol Biol, 23:549-557; Zhao C et al., 2016, Nat Struct Mol Biol, 23:558-565). Structural elements that are responsible for these functions might crosstalk and introduce unwanted effects in the reverse transcription process. Understanding the modularity of these structural elements can promote the understanding of regulations in ancient multi-functional proteins such as group II intron maturases, and can also inform the engineering of E.r. maturase into a highly efficient tool RT enzyme.

Indeed, such unwanted effects on RT efficiency have been observed, potentially caused by the intron recognition function of group II intron maturases. For example, when RepA domain 1 (D1) was used as the RNA template, E.r. maturase could only utilize a small portion of primer (7.1%±1%), and the situation is even worse for TGIRT (2.1%±0.1%) (FIG. 7B and FIG. 7C). This primer utilization problem is not as severe in RT reactions that used RepA D3 as template (FIG. 5B). This template dependency rules out the possibility that E.r. maturase has an intrinsically low RT efficiency, in which case E.r. maturase should have performed equally poorly on all RNA templates. Alternatively, this template-specific problem could be explained by depletion of both RNA template and active maturase through interactions between a positively charged surface on maturase and intron RNA (FIG. 7A). Without wishing to be bound by any particular theory, because different RNA templates have different sequences and RNA structures, the non-productive template interaction has different affinities, which leads to different degrees of primer incorporation in RT reactions for different RNA templates.

To further test this concept, mutants that have reduced positive charges on the RNA binding surface in E.r. maturase RT (finger and palm) domain were engineered and their primer incorporation rate for RepA D1 template measured. In the crystal structure of E.r. maturase RT domain (Zhao C et al., 2016, Nat Struct Mol Biol, 23:558-565), and the cryo-EM structure of L.1. group II intron-maturase complex (Qu G et al., 2016, Nat Struct Mol Biol, 23:549-557), the highly positively charged intron D4 Å and D1 binding surfaces lie on the opposite side of the RT active side (FIG. 7A), and therefore may be unlikely to play a role in reverse transcription. Therefore, a set of mutations was designed (mut1) focused on D4A binding side, including R58A, K59A, K61A and K163A. Additionally, another set of mutations was designed (mut2, including K216A and R217A) that potentially interacts with intron D1. Further, these two sets of mutants were combined to comprise 6 point mutations in total (mut1+mut2). Finally, a set of mutations on the maturase thumb domain (mut3, including K338A, K342A, and R353A) was designed that are predicted to interact with 5' exon for facilitating group II intron splicing (FIG. 7A). RT assay using RepA D1 as the template shows that mut1 construct has 2.03(±0.2)-fold increase in primer incorporation rate compared to the wild type maturase, mut2 construct has almost no change (1.09(±0.09)-fold increase), whereas mut1+mut2 construct has 2.67(±0.25)-fold increase compared to the wild type (FIG. 7B and FIG. 7C). Without wishing to be bound by any particular theory, this gradual increase in primer incorporation rate by decreasing the positive charge on the intron binding surface suggests that template and/or maturase depletion is likely to play a role in the primer incorporation problem. Additionally, without wishing to be bound by any particular theory, this non-additive improvement of mut1+mut2 construct compared to mut1 and mut2 alone suggests that the non-productive template binding is synergic. Even with 6 alanine mutations on the positively charged surface, the mut1+mut2 construct is still only able to utilize 19%±3% of RepA D1 template. Without wishing to be bound by any particular theory, this suggests that as the positively charged surface on RT domain is so extensive, more positively charged residues need to be neutralized simultaneously in order to achieve a higher RT efficiency on some RNA templates. Additionally, mut1+mut2 construct has no change in RT processivity compared to the wild-type under single-turnover condition, indicating that this positively charged surface does not affect RT processivity.

Finally, mut3 has a 0.65(±0.17)-fold decrease compared to the wild type (FIG. 7B and FIG. 7C), suggesting that the positively charged residues that interact with the 5' exon during group II intron splicing, also play a role in recruiting RNA template during RT reaction.

E.r. Maturase is an Accurate Reverse Transcriptase

Finally, the error rate of E.r. maturase was measured to determine how its accuracy is compared to optimized commercial RT SSIV and other group II intron maturases (e.g. TGIRT). Many methods have been employed to estimate polymerase error rate in the literature. For example, in the pre-NGS (next-generation sequencing) era, lacZ mutation selection assay was the most widely used method (Kunkel T A, 1985, J Biol Chem, 260:5787-5796). However, as not all RT mutations will result in a non-functional lacZ, this method will probably underestimate the error rate. The development of high-throughput sequencing allows the estimation of RT error rate by directly counting the mutation frequencies in the sequencing reads (Mohr S et al., 2013, RNA, 19:958-970). However, this method is sensitive to PCR bias, and it cannot discriminate RT error resulted from PCR amplification or base-call error from the sequencing platform (Lee D F et al., 2016, Nucleic Acids Res, 44:e118). Therefore, traditional high-throughput sequencing might not be sufficient to accurately estimate the error rate of a RT.

In this example, a single-molecule high-throughput sequencing method was employed (Lee D F et al., 2016, Nucleic Acids Res, 44:e118) to estimate RT error rate. In this method, each RT product was barcoded by a random 15 nt-long unique molecular identifier (UMI) at both ends (FIG. 8A) (Lee D F et al., 2016, Nucleic Acids Res, 44:e118). Therefore, sequencing reads can be sorted by their barcodes, and only mutation that exist in all reads with the same barcode can be considered as RT errors (FIG. 8A) (Lee D F et al., 2016, Nucleic Acids Res, 44:e118). In contrast, mutations that are inconsistent across reads with the same barcode are considered to originate from PCR amplification or the sequencing platform (FIG. 8A) (Lee D F et al., 2016, Nucleic Acids Res, 44:e118). Therefore, this barcoding method is able to distinguish errors from different sources, and it is free of PCR bias.

Using this single-molecule sequencing method (Lee D F et al., 2016, Nucleic Acids Res, 44:e118), the error rates for E.r. maturase were estimated in parallel with those of commercial SSIV. The first strand cDNA was synthesized by run-off reverse transcription from a primer that annealed to the 400 nucleotide position on RepA D3, and the second strand DNA was produced by high-fidelity DNA polymerase Q5. Then, the double-stranded DNA products were PCR amplified by Q5, which were finally sequenced by Illumina MiSeq PE250 platform. After sorting the barcodes, there are 26450 unique RT products for E.r. maturase and 921 unique products for SSIV (Table 3).

TABLE 3

Error rate determination for different reverse transcriptases.

| | E.r. WT | SSIV |
|---|---|---|
| total reads | 136434 | 138187 |
| unique products* | 921 | 26450 |
| nucleotide/product | 250 | 250 |
| total nucleotides | 230250 | 6612500 |
| substitution frequency | $1.04 \times 10^{-4}$ | $1.96 \times 10^{-4}$ |
| indel frequency | N.A. | N.A. |

The total number of reads is the raw number of sequencing reads in either forward (R1) or reverse (R2) direction for each polymerase.
The unique product is a set of sequencing reads that share the same UMI (unique molecular identifier), and only unique products that have no less than 3 reads were included.
Nucleotide/product shows the number of nucleotides that are incorporated by each polymerase after trimming the primer region and low-quality nucleotides at the end.
Total nucleotides was calculated by multiplying nucleotide/product with the number of unique products, which is the total number of nucleotides analyzed.
Substitution frequency was calculated by dividing the number of total nucleotides by the number of mutated nucleotides.
Indel (insertion-deletion) frequency was calculated by dividing the number of unique products by the number of index events.
N.A. suggests that current sequencing depth is not able to detect indels.
The * indicates only unique products that have no less than 3 reads were included.

The substitutional mutational frequency determined from these unique RT products were around $1.04 \times 10^{-4}$ for E.r. maturase and $1.96 \times 10^{-4}$ for SSIV (FIG. 8B and Table 3). Additionally, insertion and deletion events were also not observed at the sequencing depth used in this example (FIG. 8B and Table 3). These results suggested that E.r. maturase is as accurate as other high-fidelity reverse transcriptases such as SSIV. In fact, a substitutional frequency at about $1 \times 10^{-4}$ is almost the best number achievable for a polymerase without a proof-reading exonuclease domain (Lee D F et al., 2016, Nucleic Acids Res, 44:e118). The similarity in the error rate for the wild-type and mut1+mut2 E.r. maturase constructs also suggests that reducing the positive charge on maturase RNA recognition surface does not change the polymerase accuracy. The error rate for group II intron maturase TGIRT reported in the previous study (Mohr S et al., 2013, RNA, 19:958-970) is 5 times lower than the error rate for E.r. maturase determined in this example. However, this discrepancy is likely due to differences in the methods used to determine the error rate. In the previous study, the authors only measured the overlapping region of the forward and reverse reads in a pair-end sequencing experiment at a transcriptome level (Mohr S et al., 2013, RNA, 19:958-970), therefore the sequencing depth for each nucleotide might not have been sufficient to accurately estimate the error rate. These previous estimates of the apparent error rates for SSIV and TGIRT may differ from those shown herein because of the following differences in experimental design: 1. RNA template. While only a single RNA template was employed for the determination, Mohr et al. utilized an entire transcriptome. This has two effects. First, if the error rate has sequence bias, the intrinsic error rates will be different for a different RNA templates. Additionally, the sequence alignment algorithms used for the two approaches is therefore necessarily different, with more noise associated with the transcriptome-wide approach. 2. Data processing: In Mohr et al., the calculation was only performed on data in which the sequences were read twice from both ends (paired-end sequencing); and only if the overlapping region between these two reads was perfectly aligned and longer than 20 nts. This results in a small amount of data that can be included in the subsequent error rate analysis. 3. Outlier rejection: In Mohr et al., the authors discarded errors that are common to SSII and TGIRT. This causes a significant underestimate of errors.

E.r Maturase Characterization

In this example, the RT processivity of E.r. maturase has been systematically characterized for the first time, and has been compared to the popular commercial SSIV that is derived from M-MLV RT. The results demonstrate that the E.r. maturase has high intrinsic processivity that allows it to synthesize long (>9 kb) cDNA transcripts with much fewer RT stops than SSIV. The comparison of E.r. maturase with TGIRT also suggests that high processivity is a highlight of RT reactions catalyzed by group II intron maturases.

Figure 6C:
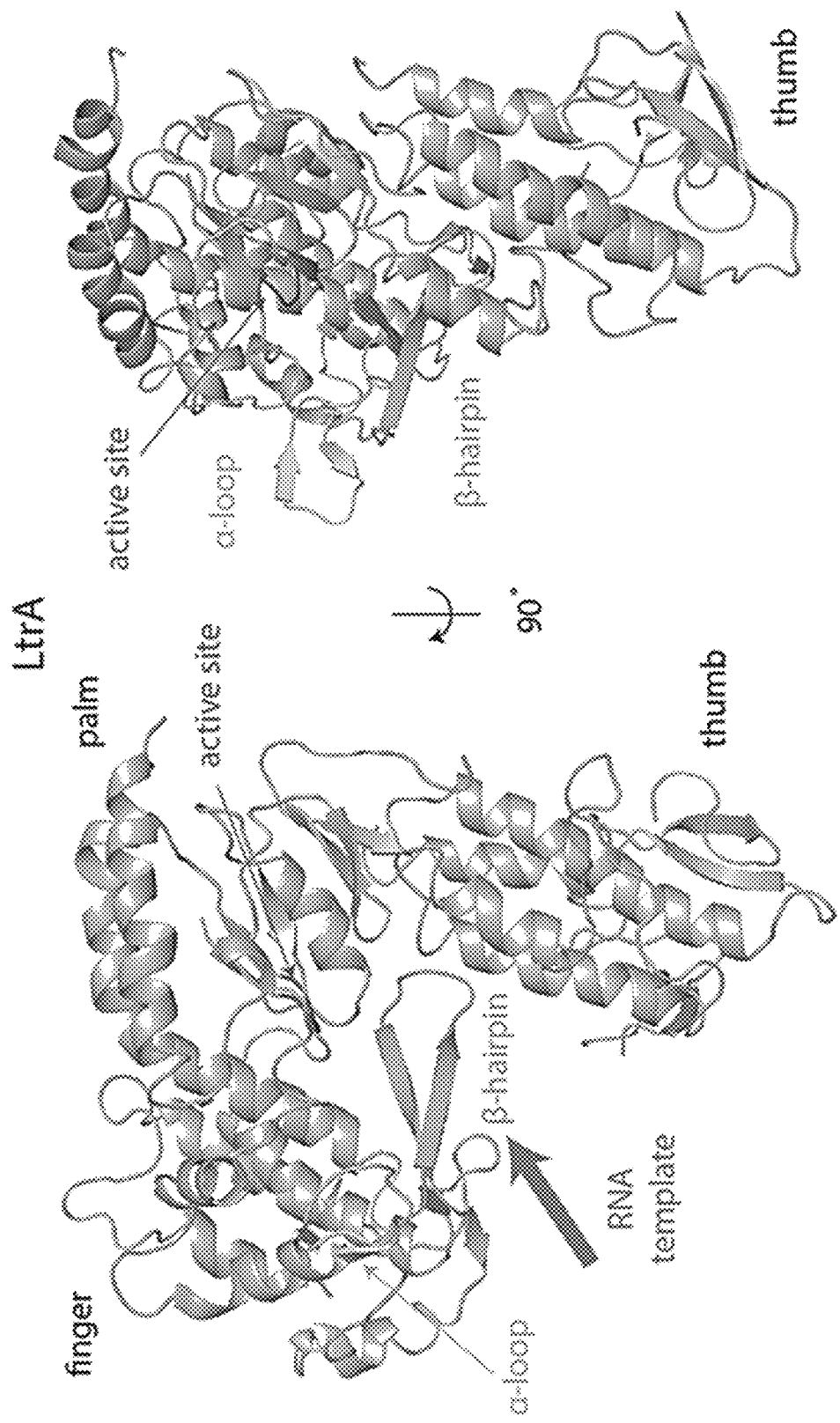

A loop structure (α-loop) was identified here that is required for the high-processivity of E.r. maturase. Based on the crystal structure of E.r. maturase RT domain (Zhao C et al., 2016, Nat Struct Mol Biol, 23:558-565), this loop encloses the RT active site and is likely able to prevent RNA template disassociation. However, this crystal structure was obtained in the absence of RNA template, and in this context, the α-loop forms a short α-helix at the tip and is stabilized in a closed conformation that appears to obstruct the RNA template entry pathway (Zhao C et al., 2016, Nat Struct Mol Biol, 23:558-565) (FIG. 6A and FIG. 6C). Interestingly, in the cryo-EM structure of LtrA (Qu G et al., 2016, Nat Struct Mol Biol, 23:549-557), the same region of this α-loop forms a β-hairpin that is stabilized in an open conformation through interactions with intron domain 4 (D4) (FIG. 6C). Therefore, in solution, this α-loop is likely to be flexible and able to swing in and out to accommodate the association of RNA template. Sequence alignment of group II intron maturases shows that the presence of this loop is highly conserved (FIG. 6A), indicating that the RT processivity of other group II intron maturases may also be at least partially mediated by this α-loop. However, the amino acid sequence within the α-loop is poorly conserved, especially at the N-terminus (FIG. 6A), suggesting that this α-loop functions primarily through steric effects. The presence of this α-loop in non-LTR retrotransposon RTs such as L1 indicates that this α-loop-mediated RT processivity is highly evolutionarily conserved and is likely to also play a role in non-LTR RTs.

Figure 9A:
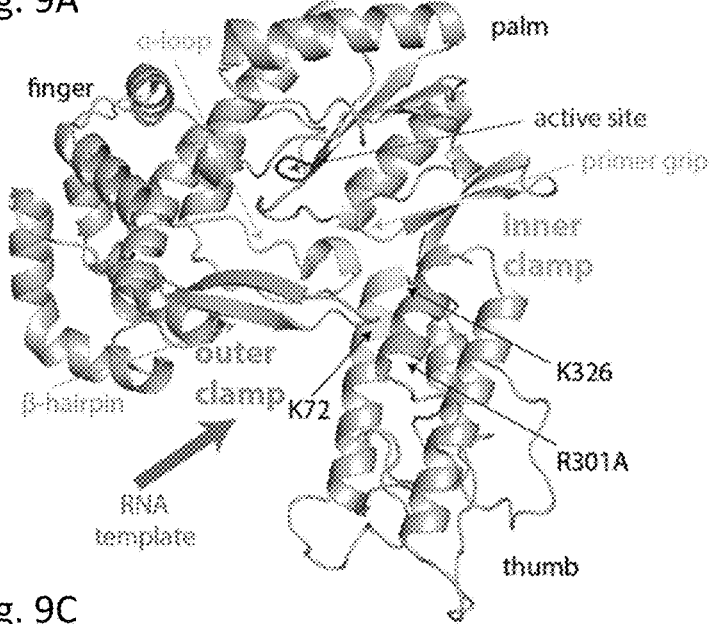
FIG. 9A through FIG. 9C, depicts results from example experiments, demonstrating a "dual clamp" mechanism for maturase processivity.
Figure 9B:
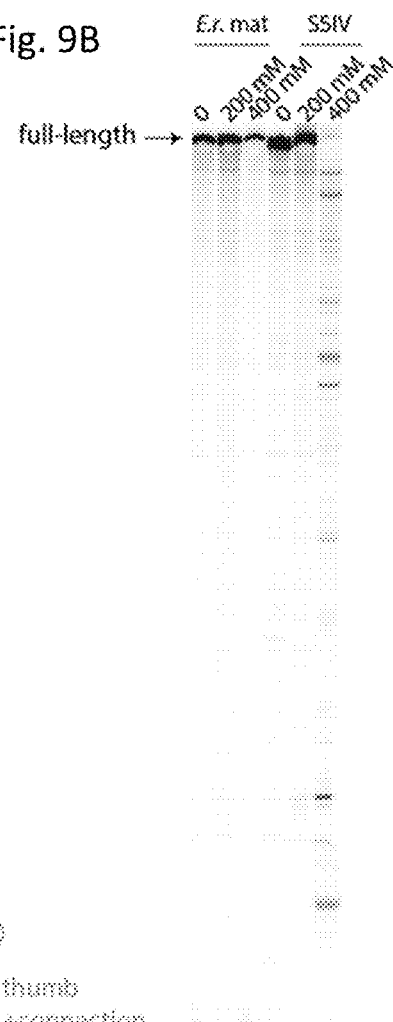
Figure 9C:
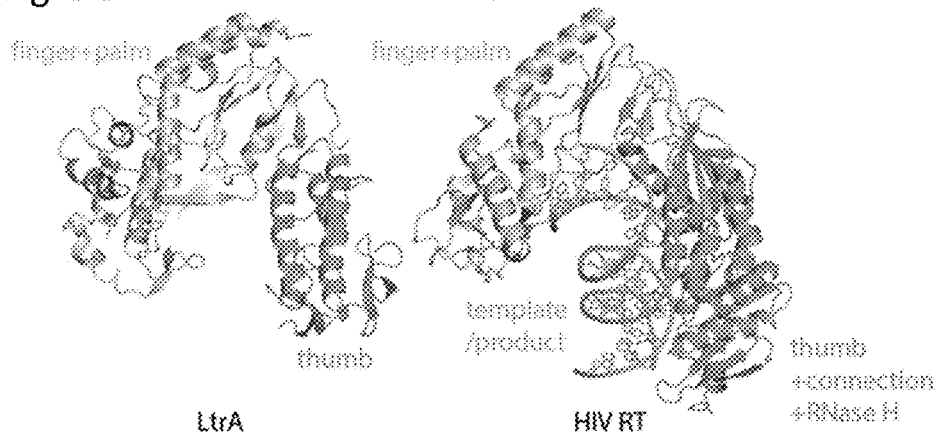

The present analysis of structures of group II intron maturases (Qu G et al., 2016, Nat Struct Mol Biol, 23:549-557; Zhao C et al., 2016, Nat Struct Mol Biol, 23:558-565) suggest this α-loop is part of a "dual clamp" that could potentially secure RNA templates tightly, thereby enabling the high processivity in group II intron maturases. The maturase-specific inner clamp, composed of α-loop and part of the thumb subdomain, grasps the template-product duplex close to the extension termini (FIG. 9A). The outer clamp, which is also present in other polymerases, is composed of a finger β-hairpin and a thumb subdomain, and could help to further stabilize the template-product duplex (FIG. 9A). Conserved positive charges are identified at the tip of this β-hairpin (K72 in E.r. maturase) and are especially enriched in the thumb (e.g. R301A and K326A in E.r. maturase). While not wishing to be bound by any particular theory, these positive charges could explain the higher tolerance to $K^+$ salt in group II intron maturases compared to SSIV (FIG. 9B). Additionally, β-hairpin has also been reported to enhance polymerase processivity by steric effects, as extending this β-hairpin 15 amino acids longer improved the processivity of HIV RT (Kew Y et al., 1998, J Biol Chem, 273:7529-7537). It is likely that these inner and outer clamps are synergistic, since deletion of α-loop alone can lead to a complete loss of processivity (FIG. 6B). By employing strong electrostatic forces on the thumb subdomain, and a small extra steric gate (α-loop) in the finger subdomain, the maturase overcomes its size limitation and accomplishes even higher processivity than HIV RT, which has a much more extensive interface with the template-product duplex (FIG. 9C).

In this example, it is demonstrated that E.r. maturase is an accurate RT that has a mutational frequency comparable to other high-fidelity RTs such as SSIV. The substitution frequencies determined for these RTs are about $1\times10^{-4}$. Although this number is over an order of magnitude larger than high-fidelity proof-reading DNA polymerases such as Pfu and Q5, it is comparable to the error rate of Klenow fragment, which also lacks a proof-reading exonuclease domain, and it is even comparable to Taq polymerase that has proof-reading activity (Lee D F et al., 2016, Nucleic Acids Res, 44:e118). Therefore, the error rate of E.r. maturase is about the best that a polymerase can achieve without a proof-reading exonuclease domain. As mentioned earlier, the lower substitution frequencies (TGIRT: $1.9\text{-}3.6\times10^{-5}$ and Superscript II: $7.6\times10^{-5}$) reported in an earlier study (Mohr S et al., 2013, RNA, 19:958-970) is likely a result from insufficient sampling of the sequencing reads used for measuring the error rate. As recognized for a long time, the error rate of a polymerase is far beyond what thermodynamics of base-pairing alone could achieve. For example, it has been reported that the ΔG for complementary and non-complementary base-pairs in aqueous solution is only 0.2-4 kcal/mol, which translates to a single mismatch in ten to a few hundred nucleotides based on Boltzmann distribution (Kunkel T A, 2004, J Biol Chem, 279:16895-16898). Previously, it was realized that high specificity beyond the thermodynamics limitation could be achieved by a mechanism called kinetic proofreading (Hopfield J J, 1974, Proc Natl Acad Sci USA, 71:4135-4139). Theoretically, by having an intermediate state after the step of initial recognition (dNTP binding) which can also discriminate correct versus incorrect substrate, the error rate of a polymerase could be raised to the second power, therefore 1 in 100 becomes 1 in 10000 (Hopfield J J, 1974, Proc Natl Acad Sci USA, 71:4135-4139). Later, it was realized that this kinetic proof-reading could be attributed to an open-to-closed conformational change of the polymerase upon dNTPs binding, which is energetically unfavorable in the presence of mismatched base pairs (Santoso Y et al., 2010, Proc Natl Acad Sci USA, 107:715-720). Based on the substitution error rate of E.r. maturase, it is very likely that E.r. maturase and other group II intron maturases also undergo this open to closed conformational change that "proof-reads" mismatched base-pairs. Engineered active site mutants that have improved fidelity of this open-to-closed conformational transition are considered in the present disclosure.

Figure 10:
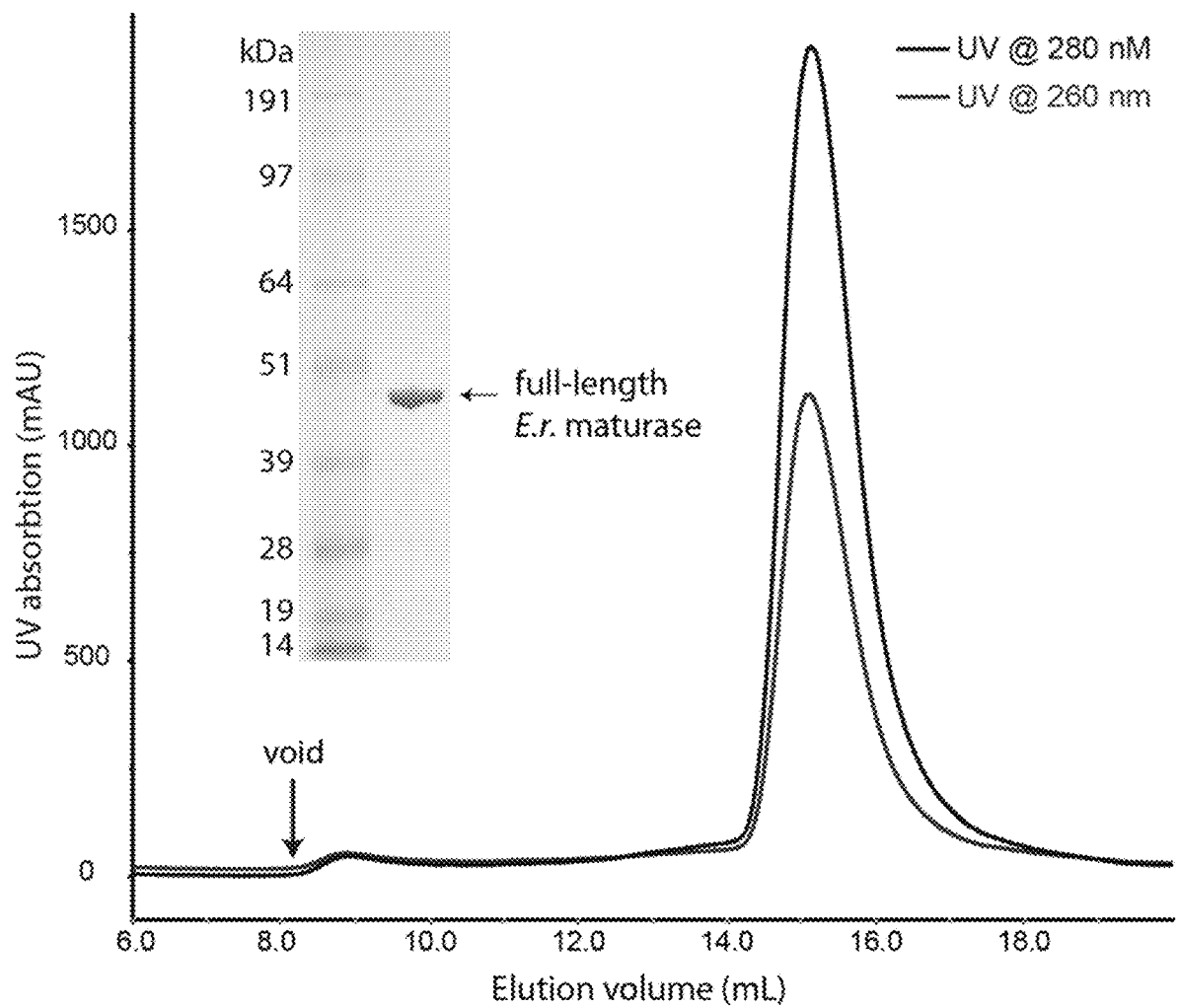
FIG. 10 depicts results from example experiments, demonstrating the chemical and conformational homogeneity of full-length E.r. maturase purified from *E. coli*. The elution profile from Superdex® S200 gel-filtration column (10/300 GL, GE Healthcare™) suggests the almost all purified full-length E.r. maturase exists as a monodispersed species. SDS-PAGE stained by Coomassie suggests that purified E.r. maturase has high chemical purity.

Because of its high processivity and fidelity, E.r. maturase is a good candidate to be utilized as a tool reverse transcriptase enzyme. Although there is already thermostable group II intron maturase commercially available, the E.r. maturase has its special potential for the following reasons. First, high resolution structural information for its RT domain (finger and palm) is available (Zhao C et al., 2016, Nat Struct Mol Biol, 23:558-565). In addition, the design of a mutant construct that is more efficient (19% primer incorporation rate) on a difficult template (RepA D1) without affecting processivity and fidelity (FIG. 6B and FIG. 6C) is demonstrated herein. In contrast, TGIRT behaves poorly on RepA D1 template and can only utilize 2% primer. Additionally, the E.r. maturase was originally identified from the group II intron database for its structural stability (Zhao C et al., 2016, Nat Struct Mol Biol, 23:558-565), and a protocol has been developed to obtain highly pure proteins in large quantities (FIG. 10). In contrast, TGIRT is only stable as a fusion construct with an N-terminal maltose-binding-protein (MBP) tag (Mohr S et al., 2013, RNA, 19:958-970), and the presence of this MBP tag might limit future engineering of TGIRT, and introduce unwanted effects in RT reactions. Therefore, E.r. maturase and the mutants described herein have great potential to be utilized as a highly efficient, processive and accurate tool reverse transcriptase.

Example 3: Optimizing the Buffer Composition for E.r. Maturase (MarathonRT)

Figure 11:
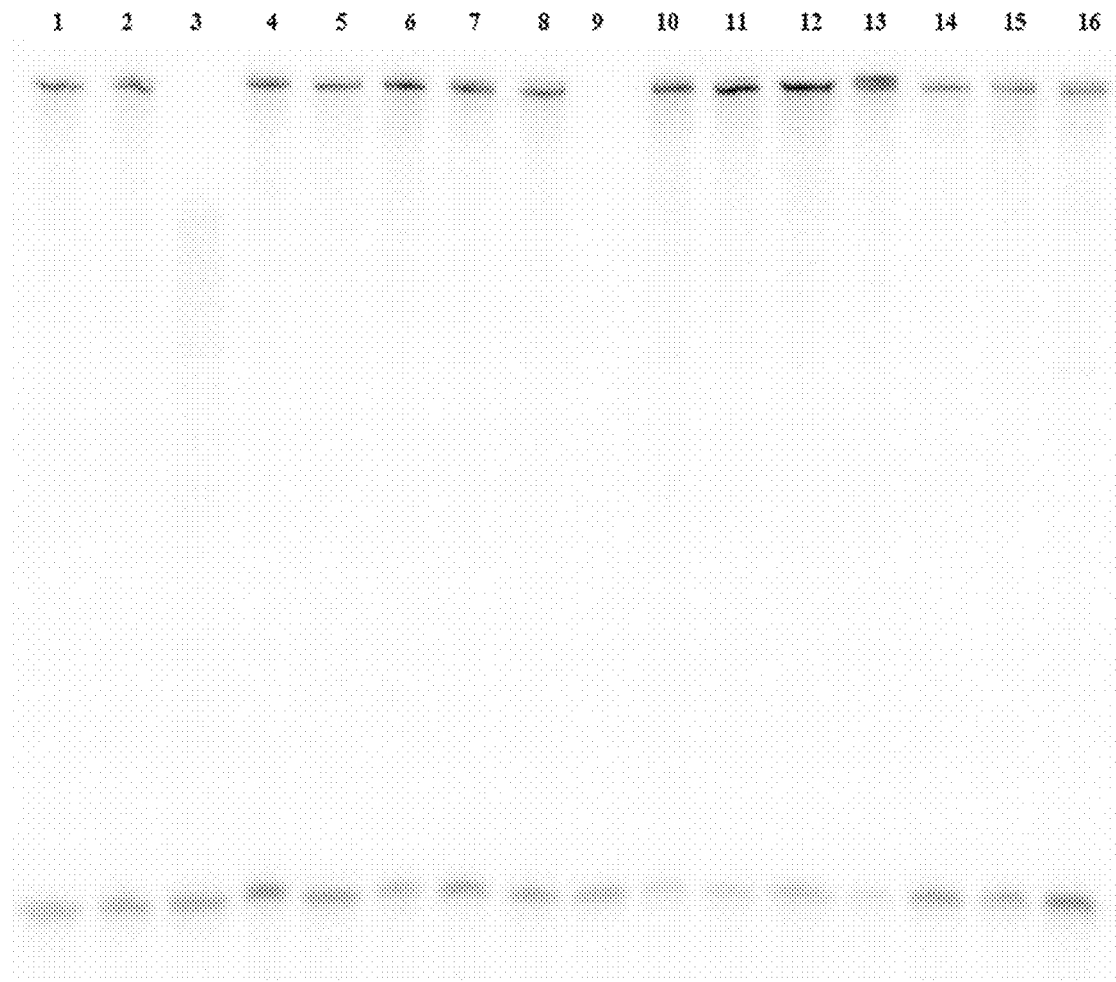
FIG. 11 depicts the results from example experiments investigating reaction optimization for E.r. maturase. The RT reactions were carried on 622 nt RepA D3 RNA using 16 different buffers. The buffer compositions are provided in Table 4, and the numbering of the 16 buffers corresponds to gel lanes in FIG. 11. The primer incorporation efficiencies for the 16 gel lanes/buffers are 62.1%, 61.8%, 46.2%, 62.5%, 58.0%, 77.4%, 67.4%, 69.8%, 21.8%, 86.0%, 86.8%, 84.8%, 91.0%, 57.1%, 66.1% and 54.7% respectively, and the yields of full-length product are 37.6%, 41.2%, 1.2%, 43.1%, 39.0%, 50.2%, 45.1%, 42.5%, 3.3%, 48.0%, 62.4%, 53.8%, 61.0%, 36.2%, 36.7% and 30.2% respectively.

To identify the optimal reaction condition for E.r. maturase, the buffer composition for reverse transcription by E.r. maturase was systematically explored, including pH, buffer components, monovalent salts and their concentrations, and the concentration of magnesium. Subsequently, the effects of different additives were also explored in the optimized buffer. The additives include betaine, trehalose, BSA, glycerol, spermidine, putrescine and triton X-100. Sixteen different buffers were tested here (Table 4). Buffer 1 developed by Zhao et al (2018, RNA, 24: 183-195) was used as the starting point. The results are shown in FIG. 11

In the optimized buffer that contains Tris pH 8.3 and 200 mM potassium chloride, the concentration of magnesium chloride was increased from 2 mM to 10 mM. It was observed that the activity of E.r maturase was almost abolished (lane 9). Thus, the optimal buffer for E.r. maturase was identified as a buffer that contains 50 mM Tris pH 8.3, 200 mM KCl, 2 mM $MgCl_2$ and 5 mM DTT.

Next, using the optimal buffer, several additives that are frequently supplemented in enzymatic assays, including betaine, trehalose, BSA, glycerol, spermidine, putrescine and triton X-100, were examined. Betaine is a zwitterion and believed to destabilize the base pairing in DNA or RNA double helix, and thus betaine may reduce the secondary structure of RNA template for E.r. maturase. In the presence of 1 M betaine, the primer incorporation is increased to 86%, but the yield of full-length product is slightly reduced to 48.0% from 50.2% (lane 10). Trehalose is an endogenously synthesized stress protectant, and its main function is to protect proteins from thermal denaturation. In the presence of 0.6 M trehalose, 86.8% primer is extended and 62.4% of full-length product is synthesized, which is by far the best additive for E.r. maturase (lane 11). BSA can improve primer incorporation to 84.8%, but the product yield is slightly increased to only 53.8% (lane 12). Interestingly, in the presence of 10% glycerol, the performance of E.r matruase is as good as that in the presence of 0.6 M trehalose, with 91% of primer incorporation and 61.0% of product yield (lane 13). Overall, the best reaction buffer for E.r maturase contains 50 mM Tris pH 8.3, 200 mM KCl, 2 mM $MgCl_2$, 5 mM DTT and 0.6 M trehalose.

| No. | Buffer component | Monovalent Salt | $Mg^{2+}$ | DTT | Additive |
|---|---|---|---|---|---|
| 1* | 50 mM HEPES pH 8.5 | 100 mM KCl | 2 mM $MgCl_2$ | 5 mM DTT | |
| 2 | 50 mM HEPES pH 8.3 | 100 mM KCl | 2 mM $MgCl_2$ | 5 mM DTT | |
| 3 | 50 mM HEPES pH 7.5 | 100 mM KCl | 2 mM $MgCl_2$ | 5 mM DTT | |
| 4 | 50 mM Tris pH 8.3 | 100 mM KCl | 2 mM $MgCl_2$ | 5 mM DTT | |
| 5 | 50 mM TAPS pH 8.3 | 100 mM KCl | 2 mM $MgCl_2$ | 5 mM DTT | |
| 6 | 50 mM Tris pH 8.3 | 200 mM KCl | 2 mM $MgCl_2$ | 5 mM DTT | |
| 7 | 50 mM Tris pH 8.3 | 200 mM NaCl | 2 mM $MgCl_2$ | 5 mM DTT | |
| 8 | 50 mM Tris pH 8.3 | 200 mM $NH_4Cl$ | 2 mM $MgCl_2$ | 5 mM DTT | |
| 9 | 50 mM Tris pH 8.3 | 200 mM KCl | 10 mM $MgCl_2$ | 5 mM DTT | |
| 10 | 50 mM Tris pH 8.3 | 200 mM KCl | 2 mM $MgCl_2$ | 5 mM DTT | 1 M betaine |
| 11 | 50 mM Tris pH 8.3 | 200 mM KCl | 2 mM $MgCl_2$ | 5 mM DTT | 0.6 M trehalose |
| 12 | 50 mM Tris pH 8.3 | 200 mM KCl | 2 mM $MgCl_2$ | 5 mM DTT | 0.2 mg/mL BSA |
| 13 | 50 mM Tris pH 8.3 | 200 mM KCl | 2 mM $MgCl_2$ | 5 mM DTT | 10% glycerol |
| 14 | 50 mM Tris pH 8.3 | 200 mM KCl | 2 mM $MgCl_2$ | 5 mM DTT | 5 mM spermidine |
| 15 | 50 mM Tris pH 8.3 | 200 mM KCl | 2 mM $MgCl_2$ | 5 mM DTT | 5 mM putrescine |
| 16 | 50 mM Tris pH 8.3 | 200 mM KCl | 2 mM $MgCl_2$ | 5 mM DTT | 0.1% triton X-100 |

In terms of pH and buffer components, the data demonstrates that E.r. maturase performs best at pH 8.3 in Tris buffer. Primer incorporation efficiencies are similar at pH 8.5 and 8.3 in HEPES buffer (lane 1 and 2), which are 62.1% and 61.8% respectively, but the cDNA yield is higher at pH 8.3, which is 41.2% compared to the yield of 37.6% at pH 8.5. At pH 7.5 in HEPES buffer (lane 3), no full-length product is detectable. Tris and TAPS buffers were further tested at pH 8.3 (lane 4 and 5), and it was found that the yield of full-length product is further improved to 43.1% in Tris buffer although primer incorporation is similar. The primer incorporation in TAPS pH 8.3 is reduced to 58.0%.

In the Tris buffer pH 8.3, the concentration of potassium chloride was then increased from 100 mM to 200 mM, and showed that the primer incorporation is further increased to 77.4% (lane 6). Sodium chloride and ammonium chloride at 200 mM give lower primer incorporation, 67.4% and 69.8% respectively (lane 7 and 8).

Example 4: Blocking the Secondary RNA Binding Site of E.r. Maturase by D4A to Improve Primer Incorporation The surface of E.r. maturase is enriched with positively charged amino acids, to which primers used for reverse transcription non-specifically binds, and thus the efficiency of primer utilization is compromised. To reduce the non-specific binding, D4A helix (FIG. 12A, originated from E.r. Group II intron) was used in the reaction buffer to block the positively charged residues on the surface of E.r. maturase, attempting to further improve the performance of E.r. maturase in the already optimized buffer (50 mM Tris pH 8.3, 200 mM KCl, 2 mM $MgCl_2$, 5 mM DTT and 0.6 M trehalose).

The ratios of D4A concentration to E.r. maturase concentration investigated were: 0:1, 1:1, 2:1, 4:1, 8:1 and 16:1 from lane 1 to lane 6 respectively (FIG. 12B). It was observed that the primer incorporation efficiencies are increased by the addition of D4A, 84.1%, 88.0%, 90.4%, 91.6%, 92.1% and 93.0% respectively from lane 1 to 6; the yields of full-length product are also increased, 43.0%, 56.3%, 58.2%, 59.8%, 55.7% and 61.2% respectively from lane 1 to 6.

The protein binding site on D4A helix is located at the apical loop and the adjacent stem structure (Matsura et al., 2001, EMBO J, 20: 7259-7270; Dai et al., 2008, Mol Cel, 30: 472-485; Singh et al., 2002, J Mol Biol, 318: 287-303). Besides the apical loop in D4A of E.r. Group II intron, the adjacent stem region may be important for maturase binding. Therefore, the apical loop and adjacent stem region of D4A, shown in the box in FIG. 12A, may represent a maturase binding site, and thus can be used as a functional fragment to reduce non-specific binding of primers to the maturase surface.

Example 5: Rational Design of E.r. Maturase Variants for Improved Thermostability Designing the Mutations E.r. maturase (also referred to as MarathonRT) is encoded by a mesophilic bacterium, *Eubacterium rectale*. It quickly loses its activity at elevated temperatures. Described herein are experiments to improve its thermostability by introducing mutations. The mutations are designed based on the conserved residues in thermophilic maturases (Ziao et al., 2008, Appl Environ Microbiol, 74: 1183-1189). The residues that are conserved in thermophilic maturases but different in E.r. maturase may suggest their roles in thermostability.

Figure 13:
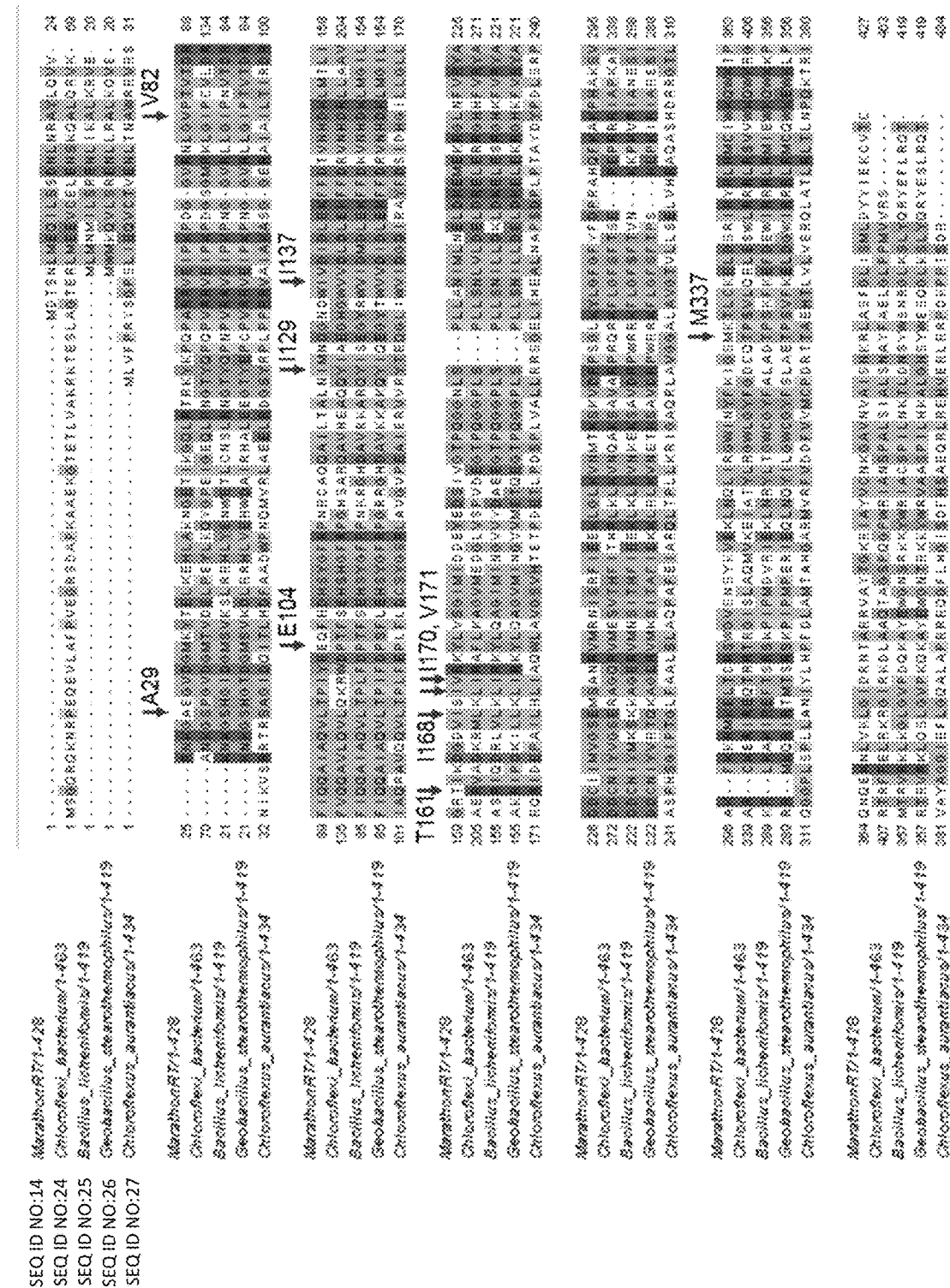
FIG. 13 depicts a sequence alignment of E.r. maturase for thermophilic maturases. The conserved residues in the thermophilic maturases are indicated by arrows.

To compare the amino acid sequence of E.r. maturase with thermophilic maturases, a multiple sequence alignment including E.r maturase and 4 maturases from thermophilic bacteria was performed (FIG. 13). Ten residues that are conserved only in thermophilic maturases were identified. These positions include 29, 82, 104, 129, 137, 161, 168, 170, 171 and 337 based on the numbering of E.r. maturase. In the tertiary structure of E.r. maturase, A29 and V82 are located in the same hydrophobic core that are conserved in all the aligned maturases. It is very likely that the two residues interact with each other in a synergetic way. Therefore, a double mutation A29S/V82I, instead of two single mutations, is more appropriate. E104 is located at the end of an α-helix, and E104P mutation may improve the stability of the α-helix. Collectively, a triple mutant, A29S/V82I/E104P, was created for thermostability analysis and enzyme activity assay.

In addition, I129 is close to H109, and I129Y mutation may introduce 7C-7C stacking with H109 that may stabilize the protein. M337 is located at a loop region between the RT domain and thumb domain, and M337T mutation may stabilize the linker region between the two domains. Thus, two single mutations, I129Y and M337T, were created for further analyses.

Expressing the Proteins

Expression of the three mutant proteins (A29S/V82I/E104P triple mutant, I129Y, and M337T) were induced by 0.5 mM IPTG at 16° C. for 18 hours. After purified by Ni-NTA, the proteins were treated by SUMO protease to remove the $His_6$-SUMO tag. The SDS-PAGE analysis showed that both wild-type and mutant proteins were expressed as mixtures of full-length and truncated proteins (FIG. 14). For the wild-type enzyme, more protein was expressed in truncated form than that in full-length form (FIG. 14A), and this situation is more severe for I129Y and M337T mutants (FIG. 14B, Lane 3, 4, 5, 6 and 7). Interestingly, the triple mutations, A29S/V82I/E104P, are mainly expressed as full-length protein (FIG. 14B, Lane 1 and 2).

Evaluating the Mutant Enzymes

After purification, activities of the three mutant enzymes were measured at different temperatures. RepA D3 served as the RNA template, and the optimized reaction buffer that contains 50 mM Tris-HCl pH 8.3, 200 mM KCl, 2 mM $MgCl_2$, 5 mM DTT and 0.6 M trehalose was used. The reverse transcription reactions were carried at 42, 50, 55 and 60° C. respectively to evaluate their performance and thermostability, and the wild-type enzyme served as the control.

Figure 15:
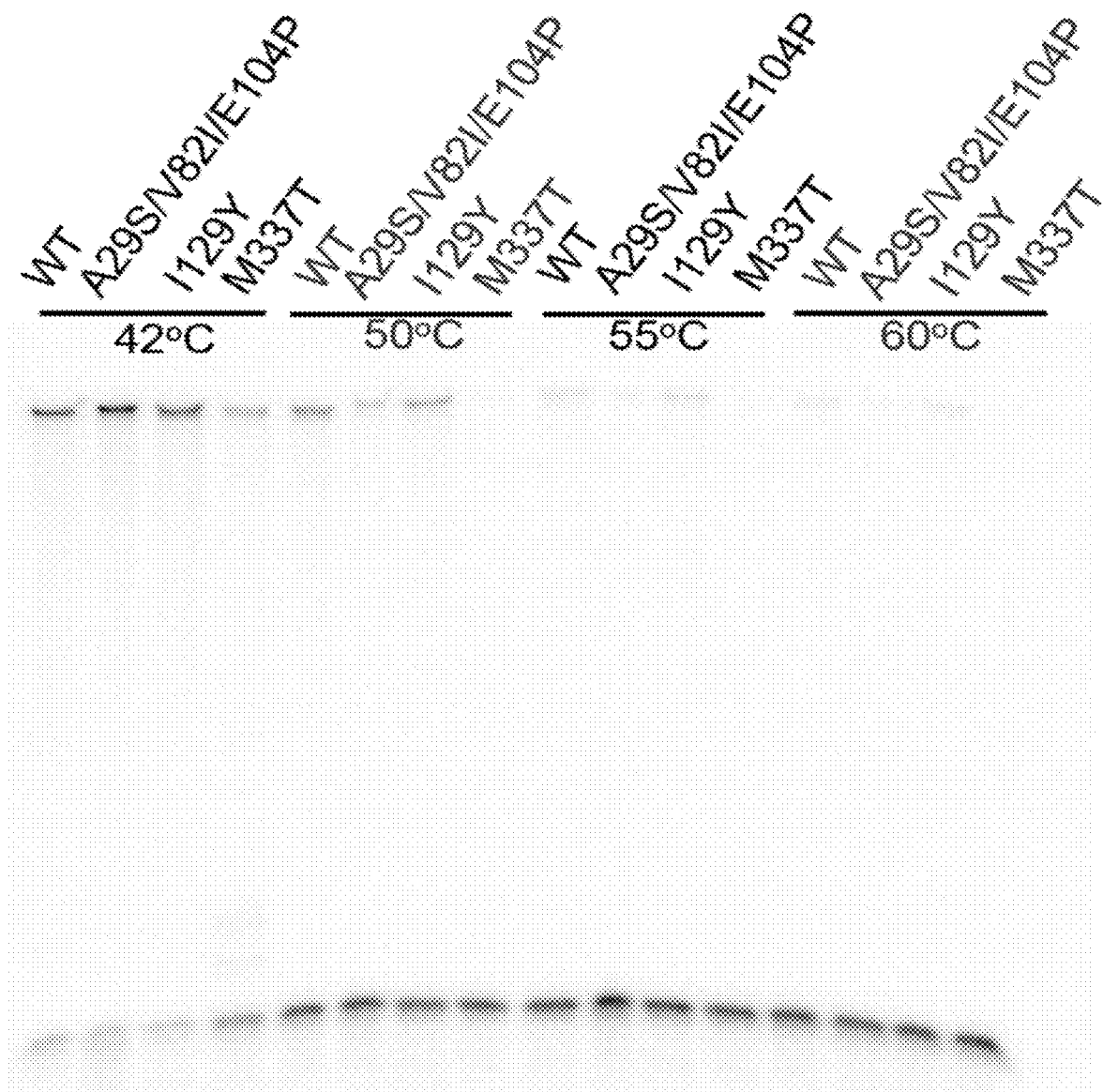
FIG. 15 depicts the results of example experiments using enzymatic assays for three E.r. maturase mutants. At 42° C., the primer incorporation efficiencies by wild-type, A29S/V82I/E104P, I129Y and M337T are 81.6%, 86.1%, 82.7% and 63.5% respectively, and the yields of full-length product are 39.5%, 50.3%, 41.7% and 18.1% respectively. At 50° C., the primer incorporation efficiencies are reduced to 51.4%, 32.3%, 45.8% and 23.3% respectively, and the yields of full-length product are reduced to 24.3%, 11.2%, 20.9% and 1.9% respectively.

At 42° C., the triple mutant A29S/V82I/E104P has a better performance than the wild-type E.r maturase, giving a higher primer incorporation efficiency and full-length product yield (FIG. 15). However, A29S/V82I/E104P is less thermostable than the wild-type E.r. maturase. At higher temperatures, the wild-type E.r maturase is more active than the A29S/V82I/E104P mutant. The performance and thermostability of I129Y mutant is almost the same as the wild-type enzyme at different temperatures, as shown in FIG. 15. The M337T mutation severely impairs the performance and thermostability of E.r maturase. Since these enzymes are almost inactive at 55 and 60° C., their activities were not quantified under these temperatures. At 42° C., the primer incorporation efficiencies by wild-type, A29S/V82I/E104P, I129Y and M337T are 81.6%, 86.1%, 82.7% and 63.5% respectively, and the yields of full-length product are 39.5%, 50.3%, 41.7% and 18.1% respectively. At 50° C., the primer incorporation efficiencies are reduced to 51.4%, 32.3%, 45.8% and 23.3% respectively, and the yields of full-length product are reduced to 24.3%, 11.2%, 20.9% and 1.9% respectively.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising a reverse transcriptase comprising a variant of *Eubacterium* rectale (E.r.) maturase, wherein the reverse transcriptase comprises one or more mutations in wildtype E.r. maturase, wherein the wildtype E.r. maturase comprises the amino acid sequence set forth in SEQ ID NO: 14. and further wherein the E.r. maturase variant comprises an amino acid sequence having greater than about 90% identity to the amino acid sequence set forth in SEQ ID NO:14, and further wherein the E. r. maturase variant comprises at least one mutation selected from the group consisting of: R58A, K59A, K61A, K163A, K216A, R217A, K338A, K342A, and R353A relative to SEQ ID NO: 14.

2. The composition of claim 1, wherein the reverse transcriptase comprises an amino acid sequence selected from the group consisting of SEQ ID NO: 15, SEQ ID NO: 16, SEQ ID NO: 17 and SEQ ID NO:18.

3. The composition of claim 1, wherein the reverse transcriptase further comprises at least one mutation selected from the group consisting of: mutation of the C-terminal DNA binding domain, mutation of the a-loop, a mutation to produce increased Lys-Glu pairs within rigid sections of the tertiary structure, addition of an exonuclease domain to enhance fidelity, mutation of the thumb domain, mutation of the catalytic site, and a substitution mutation wherein one or more residues or a domain in E.r. maturase is replaced with one or more residues or a domain derived from a maturase enzyme of an organism other than *Eubacterium* rectale.

4. The composition of claim 3, wherein the mutation is selected from the group consisting of:
  a) a mutation of the C-terminal DNA binding domain, wherein the mutation comprises at least one selected from the group consisting of: ΔC-term, K388X, R389X, K396X, K406X, R407X, and K423X, wherein X denotes any amino acid, wherein ΔC-term denotes deletion of the residues corresponding to position 387 to position 427 of SEQ ID NO: 14;
  b) a mutation of the α-loop, wherein the mutation is selected from the group consisting of: mutations in the N-terminal portion of the α-loop, and substitution of the α-loop with an α-loop from another maturase reverse transcriptase;
  c) a mutation to produce increased Lys-Glu pairs within rigid sections of the tertiary structure, wherein the mutation comprises at least one selected from the group consisting of: L11X, L21X, and 513X;
  d) a mutation of the thumb domain, wherein the mutation comprises at least one selected from the group consisting of: 5315X, E319X, Q323X, K338X, K342X, and R353X, wherein X denotes any amino acid; and
  e) a mutation of the catalytic site, wherein the mutation comprises at least one selected from the group consisting of: A225X, R114X, Y224X, I179X, M180X, I181X, E143X, K65X, and L201X, wherein X is any amino acid.

5. The composition of claim 4, wherein in a) X is selected from the group consisting of: Alanine (A) and Serine (S).

6. The composition of claim 4, wherein in c) X is Glutamic acid (E).

7. The composition of claim 4, wherein the mutation of the thumb domain comprises at least one selected from the group consisting of: S315K, E319K, Q323K, K338A, K342A, and R353A.

8. The composition of claim 3, wherein the substitution mutation wherein a domain in E.r. maturase is replaced with a domain derived from a maturase enzyme of an organism other than *Eubacterium* rectale is selected from the group consisting of: replacement of the finger domain of E.r. maturase with a finger domain of another maturase reverse transcriptase, and replacement of the palm domain of E.r. maturase with a palm domain of another maturase reverse transcriptase.

9. The composition of claim 3, wherein the substitution mutation wherein one or more residues of E.r. maturase is replaced with one or more residues derived from a maturase enzyme of an organism other than *Eubacterium* rectale comprises at least one selected from the group consisting of: A29X, V82X, E104X, I129X, I137X, T161X, I168X, I170X, V171X, and M337X, where X denotes any amino acid.

10. The composition of claim 9, wherein the substitution mutation comprsies at least one selected from the group consisting of A29S, V82I, E104P, I129Y, I137V, T161R, I168L, I170L, V171I, and M337T.

11. The composition of claim 1 further comprising an agent that reduces non-specific binding of primer to the surface of the E.r. maturase.

12. The composition of claim 11, wherein the agent comprises at least one selected from the group consisting of:
  a) a RNA stem-loop molecule;
  b) a nucleic acid molecule derived from a group II intron; and
  c) D4A or a variant thereof.

13. A composition comprising an isolated nucleic acid molecule encoding the reverse transcriptase of claim 1.

14. A method of performing reverse transcription, comprising contacting an RNA molecule with a composition comprising a reverse transcriptase comprising a variant *Eubacterium* rectale maturase wherein the E.r. maturase variant comprises an amino acid sequence having greater than about 90% identity to the amino acid sequence set forth in SEQ ID NO: 14, and further wherein the E.r. maturase variant comprises at least one mutation selected from the group consisting of: R58A, K59A, K61A, K163A, K216A, R217A, K338A, K342A, and R353A relative to SEQ ID NO: 14.

15. The method of claim 14, wherein the variant of E.r. maturase is used in an optimized reaction buffer, wherein the optimized reaction buffer comprises Tris at a concentration of about 10 mM to about 100 mM, KCl at a concentration of about 100 mM to about 500 mM, $MgCl_2$ at a concentration of about 0.5 mM to about 5 mM, DTT at a concentration of about 1 mM to about 10 mM, and wherein the optimized reaction buffer has a pH of about 8 to 8.5.

16. The method of claim 15, wherein the optimized reaction buffer further comprises one or more protein stabilizing agents.

17. The method of claim 14, wherein the variant of E.r. maturase is contacted with an agent that reduces non-specific binding of primers to the or variant of E.r. maturase, wherein the agent comprises at least one selected from the group consisting of:
  a) a RNA stem-loop molecule;
  b) a nucleic acid molecule derived from a group II intron; and
  c) D4A or a variant thereof.

* * * * *

SEQUENCE LISTING

<160> NUMBER OF SEQ ID NOS: 30

<210> SEQ ID NO 1
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 1
accatatttc catccaccaa gcgc                                       24

<210> SEQ ID NO 2
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 2
taataggtga ggtttcaatg                                            20

<210> SEQ ID NO 3
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 3
gtctccgctg gtgtgag                                               17

<210> SEQ ID NO 4
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 4
aaggaacagt tagctatgga gtg                                        23

<210> SEQ ID NO 5
<211> LENGTH: 65
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (27)..(51)
<223> OTHER INFORMATION: sequence barcode region, n represents any
      nucleotide

<400> SEQUENCE: 5
ctacacgacg ctcttccgat ctctgtnnnn nnnnnnnnnn ngattatagg acatttaggt    60
cgtac                                                              65

<210> SEQ ID NO 6
<211> LENGTH: 63
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (26)..(50)
<223> OTHER INFORMATION: sequence barcode region, n represents any
      nucleotide

<400> SEQUENCE: 6
cagacgtgtg ctcttccgat cggtannnnn nnnnnnnnnn acatttctaa ctggaagtca    60
agc                                                                63

<210> SEQ ID NO 7
<211> LENGTH: 63
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (26)..(40)
<223> OTHER INFORMATION: n is a, c, g, or t

<400> SEQUENCE: 7
cagacgtgtg ctcttccgat cggtannnnn nnnnnnnnnn acatttctaa ctggaagtca      60
agc                                                                   63

<210> SEQ ID NO 8
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 8
cagacgtgtg ctcttccgat c                                               21

<210> SEQ ID NO 9
<211> LENGTH: 64
<212> TYPE: DNA
<213> ORGANISM: Artificial Sequence
<220> FEATURE:
<223> OTHER INFORMATION: Chemically Synthesized

<400> SEQUENCE: 9
caagcagaag acggcatacg agatacatcg gtgactggag ttcagacgtg tgctcttccg      60
atct                                                                  64

<210> SEQ ID NO 10
<211> LENGTH: 64
<212> TYPE: DNA
<213> ORGANISM: Artificial Sequence
<220> FEATURE:
<223> OTHER INFORMATION: Chemically Synthesized

<400> SEQUENCE: 10
caagcagaag acggcatacg agattggtca gtgactggag ttcagacgtg tgctcttccg      60
atct                                                                  64

<210> SEQ ID NO 11
<211> LENGTH: 64
<212> TYPE: DNA
<213> ORGANISM: Artificial Sequence
<220> FEATURE:
<223> OTHER INFORMATION: Chemically Synthesized

<400> SEQUENCE: 11
caagcagaag acggcatacg agatacagtg gtgactggag ttcagacgtg tgctcttccg      60
atct                                                                  64

<210> SEQ ID NO 12
<211> LENGTH: 64
<212> TYPE: DNA
<213> ORGANISM: Artificial Sequence
<220> FEATURE:
<223> OTHER INFORMATION: Chemically Synthesized

<400> SEQUENCE: 12
caagcagaag acggcatacg agatcagatc gtgactggag ttcagacgtg tgctcttccg     60
atct     64

<210> SEQ ID NO 13
<211> LENGTH: 57
<212> TYPE: DNA
<213> ORGANISM: Artificial Sequence
<220> FEATURE:
<223> OTHER INFORMATION: Chemically Synthesized

<400> SEQUENCE: 13
aatgatacgg cgaccaccga gatctacact ctttccctac acgacgctct tccgatc     57

<210> SEQ ID NO 14
<211> LENGTH: 427
<212> TYPE: PRT
<213> ORGANISM: Eubacterium rectale

<400> SEQUENCE: 14

```
Met Asp Thr Ser Asn Leu Met Glu Gln Ile Leu Ser Ser Asp Asn Leu
1               5                   10                  15

Asn Arg Ala Tyr Leu Gln Val Val Arg Asn Lys Gly Ala Glu Gly Val
            20                  25                  30

Asp Gly Met Lys Tyr Thr Glu Leu Lys Glu His Leu Ala Lys Asn Gly
        35                  40                  45

Glu Thr Ile Lys Gly Gln Leu Arg Thr Arg Lys Tyr Lys Pro Gln Pro
    50                  55                  60

Ala Arg Arg Val Glu Ile Pro Lys Pro Asp Gly Gly Val Arg Asn Leu
65                  70                  75                  80

Gly Val Pro Thr Val Thr Asp Arg Phe Ile Gln Gln Ala Ile Ala Gln
                85                  90                  95

Val Leu Thr Pro Ile Tyr Glu Glu Gln Phe His Asp His Ser Tyr Gly
            100                 105                 110

Phe Arg Pro Asn Arg Cys Ala Gln Gln Ala Ile Leu Thr Ala Leu Asn
        115                 120                 125

Ile Met Asn Asp Gly Asn Asp Trp Ile Val Asp Ile Asp Leu Glu Lys
    130                 135                 140

Phe Phe Asp Thr Val Asn His Asp Lys Leu Met Thr Leu Ile Gly Arg
145                 150                 155                 160

Thr Ile Lys Asp Gly Asp Val Ile Ser Ile Val Arg Lys Tyr Leu Val
                165                 170                 175

Ser Gly Ile Met Ile Asp Asp Glu Tyr Glu Asp Ser Ile Val Gly Thr
            180                 185                 190

Pro Gln Gly Gly Asn Leu Ser Pro Leu Leu Ala Asn Ile Met Leu Asn
        195                 200                 205

Glu Leu Asp Lys Glu Met Glu Lys Arg Gly Leu Asn Phe Val Arg Tyr
    210                 215                 220

Ala Asp Asp Cys Ile Ile Met Val Gly Ser Glu Met Ser Ala Asn Arg
225                 230                 235                 240

Val Met Arg Asn Ile Ser Arg Phe Ile Glu Glu Lys Leu Gly Leu Lys
                245                 250                 255

Val Asn Met Thr Lys Ser Lys Val Asp Arg Pro Ser Gly Leu Lys Tyr
            260                 265                 270

Leu Gly Phe Gly Phe Tyr Phe Asp Pro Arg Ala His Gln Phe Lys Ala
```

```
                275                 280                 285
Lys Pro His Ala Lys Ser Val Ala Lys Phe Lys Lys Arg Met Lys Glu
    290                 295                 300

Leu Thr Cys Arg Ser Trp Gly Val Ser Asn Ser Tyr Lys Val Glu Lys
305                 310                 315                 320

Leu Asn Gln Leu Ile Arg Gly Trp Ile Asn Tyr Phe Lys Ile Gly Ser
                325                 330                 335

Met Lys Thr Leu Cys Lys Glu Leu Asp Ser Arg Ile Arg Tyr Arg Leu
                340                 345                 350

Arg Met Cys Ile Trp Lys Gln Trp Lys Thr Pro Gln Asn Gln Glu Lys
            355                 360                 365

Asn Leu Val Lys Leu Gly Ile Asp Arg Asn Thr Ala Arg Arg Val Ala
        370                 375                 380

Tyr Thr Gly Lys Arg Ile Ala Tyr Val Cys Asn Lys Gly Ala Val Asn
385                 390                 395                 400

Val Ala Ile Ser Asn Lys Arg Leu Ala Ser Phe Gly Leu Ile Ser Met
                405                 410                 415

Leu Asp Tyr Tyr Ile Glu Lys Cys Val Thr Cys
                420                 425

<210> SEQ ID NO 15
<211> LENGTH: 427
<212> TYPE: PRT
<213> ORGANISM: Artificial Sequence
<220> FEATURE:
<223> OTHER INFORMATION: Chemically Synthesized, E.r. maturase mut1

<400> SEQUENCE: 15

Met Asp Thr Ser Asn Leu Met Glu Gln Ile Leu Ser Ser Asp Asn Leu
1               5                   10                  15

Asn Arg Ala Tyr Leu Gln Val Val Arg Asn Lys Gly Ala Glu Gly Val
            20                  25                  30

Asp Gly Met Lys Tyr Thr Glu Leu Lys Glu His Leu Ala Lys Asn Gly
        35                  40                  45

Glu Thr Ile Lys Gly Gln Leu Arg Thr Ala Ala Tyr Ala Pro Gln Pro
    50                  55                  60

Ala Arg Arg Val Glu Ile Pro Lys Pro Asp Gly Gly Val Arg Asn Leu
65                  70                  75                  80

Gly Val Pro Thr Val Thr Asp Arg Phe Ile Gln Ala Ile Ala Gln
                85                  90                  95

Val Leu Thr Pro Ile Tyr Glu Glu Gln Phe His Asp His Ser Tyr Gly
                100                 105                 110

Phe Arg Pro Asn Arg Cys Ala Gln Gln Ala Ile Leu Thr Ala Leu Asn
            115                 120                 125

Ile Met Asn Asp Gly Asn Asp Trp Ile Val Asp Ile Asp Leu Glu Lys
        130                 135                 140

Phe Phe Asp Thr Val Asn His Asp Lys Leu Met Thr Leu Ile Gly Arg
145                 150                 155                 160

Thr Ile Ala Asp Gly Asp Val Ile Ser Ile Val Arg Lys Tyr Leu Val
                165                 170                 175

Ser Gly Ile Met Ile Asp Asp Glu Tyr Glu Asp Ser Ile Val Gly Thr
                180                 185                 190

Pro Gln Gly Gly Asn Leu Ser Pro Leu Leu Ala Asn Ile Met Leu Asn
            195                 200                 205

Glu Leu Asp Lys Glu Met Glu Lys Arg Gly Leu Asn Phe Val Arg Tyr
```

```
              210                 215                 220
Ala Asp Asp Cys Ile Ile Met Val Gly Ser Glu Met Ser Ala Asn Arg
225                 230                 235                 240

Val Met Arg Asn Ile Ser Arg Phe Ile Glu Glu Lys Leu Gly Leu Lys
                245                 250                 255

Val Asn Met Thr Lys Ser Lys Val Asp Arg Pro Ser Gly Leu Lys Tyr
            260                 265                 270

Leu Gly Phe Gly Phe Tyr Phe Asp Pro Arg Ala His Gln Phe Lys Ala
            275                 280                 285

Lys Pro His Ala Lys Ser Val Ala Lys Phe Lys Lys Arg Met Lys Glu
        290                 295                 300

Leu Thr Cys Arg Ser Trp Gly Val Ser Asn Ser Tyr Lys Val Glu Lys
305                 310                 315                 320

Leu Asn Gln Leu Ile Arg Gly Trp Ile Asn Tyr Phe Lys Ile Gly Ser
                325                 330                 335

Met Lys Thr Leu Cys Lys Glu Leu Asp Ser Arg Ile Arg Tyr Arg Leu
            340                 345                 350

Arg Met Cys Ile Trp Lys Gln Trp Lys Thr Pro Gln Asn Gln Glu Lys
        355                 360                 365

Asn Leu Val Lys Leu Gly Ile Asp Arg Asn Thr Ala Arg Arg Val Ala
    370                 375                 380

Tyr Thr Gly Lys Arg Ile Ala Tyr Val Cys Asn Lys Gly Ala Val Asn
385                 390                 395                 400

Val Ala Ile Ser Asn Lys Arg Leu Ala Ser Phe Gly Leu Ile Ser Met
                405                 410                 415

Leu Asp Tyr Tyr Ile Glu Lys Cys Val Thr Cys
            420                 425

<210> SEQ ID NO 16
<211> LENGTH: 426
<212> TYPE: PRT
<213> ORGANISM: Artificial Sequence
<220> FEATURE:
<223> OTHER INFORMATION: Chemically Synthesized, E.r. maturase mut2

<400> SEQUENCE: 16

Met Asp Thr Ser Asn Leu Met Glu Gln Ile Leu Ser Ser Asp Asn Leu
1               5                   10                  15

Asn Arg Ala Tyr Leu Gln Val Val Arg Asn Lys Gly Ala Glu Gly Val
                20                  25                  30

Asp Gly Met Lys Tyr Thr Glu Leu Lys Glu His Leu Ala Lys Asn Gly
            35                  40                  45

Glu Thr Ile Lys Gly Gln Leu Arg Thr Arg Lys Tyr Lys Pro Gln Pro
        50                  55                  60

Ala Arg Arg Val Glu Ile Pro Lys Pro Asp Gly Gly Val Arg Asn Leu
65                  70                  75                  80

Gly Val Pro Thr Val Thr Asp Arg Phe Ile Gln Gln Ala Ile Ala Gln
                85                  90                  95

Val Leu Thr Pro Ile Tyr Glu Glu Gln Phe His Asp His Ser Tyr Gly
            100                 105                 110

Phe Arg Pro Asn Arg Cys Ala Gln Gln Ala Ile Leu Thr Ala Leu Asn
        115                 120                 125

Ile Met Asn Asp Gly Asn Asp Trp Ile Val Asp Ile Asp Leu Glu Lys
    130                 135                 140

Phe Phe Asp Thr Val Asn His Asp Lys Leu Met Thr Leu Ile Gly Arg
```

```
            145                 150                 155                 160
Thr Ile Lys Asp Gly Asp Val Ile Ser Ile Val Arg Lys Tyr Leu Val
                    165                 170                 175

Ser Gly Ile Met Ile Asp Asp Glu Tyr Glu Asp Ser Ile Val Gly Thr
                    180                 185                 190

Pro Gln Gly Gly Asn Leu Ser Pro Leu Leu Ala Asn Ile Met Leu Asn
                    195                 200                 205

Glu Leu Asp Lys Glu Met Glu Ala Ala Gly Leu Asn Phe Val Arg Tyr
            210                 215                 220

Ala Asp Asp Cys Ile Ile Met Val Gly Ser Glu Met Ser Ala Asn Arg
225                 230                 235                 240

Val Met Arg Asn Ile Ser Arg Phe Ile Glu Glu Lys Leu Gly Leu Lys
                245                 250                 255

Val Asn Met Thr Lys Ser Lys Val Asp Arg Pro Ser Gly Leu Lys Tyr
                260                 265                 270

Leu Gly Phe Gly Phe Tyr Phe Asp Pro Arg Ala His Gln Phe Lys Ala
                275                 280                 285

Lys Pro His Ala Lys Ser Val Ala Lys Phe Lys Lys Arg Met Lys Glu
            290                 295                 300

Leu Thr Cys Arg Ser Trp Gly Val Ser Asn Ser Tyr Lys Val Glu Lys
305                 310                 315                 320

Leu Asn Gln Leu Ile Arg Gly Trp Ile Asn Tyr Phe Lys Ile Gly Ser
                325                 330                 335

Met Lys Thr Leu Cys Lys Glu Leu Asp Ser Arg Ile Arg Tyr Arg Leu
                340                 345                 350

Arg Met Cys Ile Trp Lys Gln Trp Lys Thr Pro Gln Asn Gln Glu Lys
            355                 360                 365

Asn Leu Val Lys Leu Gly Ile Asp Arg Asn Thr Ala Arg Arg Val Ala
            370                 375                 380

Tyr Thr Gly Lys Arg Ile Ala Tyr Val Cys Asn Lys Gly Ala Val Asn
385                 390                 395                 400

Val Ala Ile Ser Asn Lys Arg Leu Ala Ser Phe Gly Leu Ile Ser Met
                405                 410                 415

Leu Asp Tyr Tyr Ile Glu Lys Cys Val Thr
                420                 425

<210> SEQ ID NO 17
<211> LENGTH: 427
<212> TYPE: PRT
<213> ORGANISM: Artificial Sequence
<220> FEATURE:
<223> OTHER INFORMATION: Chemically Synthesized, E.r. maturase mut1+mut2

<400> SEQUENCE: 17

Met Asp Thr Ser Asn Leu Met Glu Gln Ile Leu Ser Ser Asp Asn Leu
1               5                   10                  15

Asn Arg Ala Tyr Leu Gln Val Val Arg Asn Lys Gly Ala Glu Gly Val
                20                  25                  30

Asp Gly Met Lys Tyr Thr Glu Leu Lys Glu His Leu Ala Lys Asn Gly
            35                  40                  45

Glu Thr Ile Lys Gly Gln Leu Arg Thr Ala Ala Tyr Ala Pro Gln Pro
        50                  55                  60

Ala Arg Arg Val Glu Ile Pro Lys Pro Asp Gly Gly Val Arg Asn Leu
65                  70                  75                  80

Gly Val Pro Thr Val Thr Asp Arg Phe Ile Gln Gln Ala Ile Ala Gln
```

85                  90                  95
Val Leu Thr Pro Ile Tyr Glu Glu Gln Phe His Asp His Ser Tyr Gly
            100                 105                 110

Phe Arg Pro Asn Arg Cys Ala Gln Gln Ala Ile Leu Thr Ala Leu Asn
        115                 120                 125

Ile Met Asn Asp Gly Asn Asp Trp Ile Val Asp Ile Asp Leu Glu Lys
    130                 135                 140

Phe Phe Asp Thr Val Asn His Asp Lys Leu Met Thr Leu Ile Gly Arg
145                 150                 155                 160

Thr Ile Ala Asp Gly Asp Val Ile Ser Ile Val Arg Lys Tyr Leu Val
                165                 170                 175

Ser Gly Ile Met Ile Asp Asp Glu Tyr Glu Asp Ser Ile Val Gly Thr
            180                 185                 190

Pro Gln Gly Gly Asn Leu Ser Pro Leu Leu Ala Asn Ile Met Leu Asn
        195                 200                 205

Glu Leu Asp Lys Glu Met Glu Ala Ala Gly Leu Asn Phe Val Arg Tyr
    210                 215                 220

Ala Asp Asp Cys Ile Ile Met Val Gly Ser Glu Met Ser Ala Asn Arg
225                 230                 235                 240

Val Met Arg Asn Ile Ser Arg Phe Ile Glu Glu Lys Leu Gly Leu Lys
                245                 250                 255

Val Asn Met Thr Lys Ser Lys Val Asp Arg Pro Ser Gly Leu Lys Tyr
            260                 265                 270

Leu Gly Phe Gly Phe Tyr Phe Asp Pro Arg Ala His Gln Phe Lys Ala
        275                 280                 285

Lys Pro His Ala Lys Ser Val Ala Lys Phe Lys Lys Arg Met Lys Glu
    290                 295                 300

Leu Thr Cys Arg Ser Trp Gly Val Ser Asn Ser Tyr Lys Val Glu Lys
305                 310                 315                 320

Leu Asn Gln Leu Ile Arg Gly Trp Ile Asn Tyr Phe Lys Ile Gly Ser
                325                 330                 335

Met Lys Thr Leu Cys Lys Glu Leu Asp Ser Arg Ile Arg Tyr Arg Leu
            340                 345                 350

Arg Met Cys Ile Trp Lys Gln Trp Lys Thr Pro Gln Asn Gln Glu Lys
        355                 360                 365

Asn Leu Val Lys Leu Gly Ile Asp Arg Asn Thr Ala Arg Arg Val Ala
    370                 375                 380

Tyr Thr Gly Lys Arg Ile Ala Tyr Val Cys Asn Lys Gly Ala Val Asn
385                 390                 395                 400

Val Ala Ile Ser Asn Lys Arg Leu Ala Ser Phe Gly Leu Ile Ser Met
                405                 410                 415

Leu Asp Tyr Tyr Ile Glu Lys Cys Val Thr Cys
            420                 425

<210> SEQ ID NO 18
<211> LENGTH: 427
<212> TYPE: PRT
<213> ORGANISM: Artificial Sequence
<220> FEATURE:
<223> OTHER INFORMATION: Chemically Synthesized, E.r. maturase mut3

<400> SEQUENCE: 18

Met Asp Thr Ser Asn Leu Met Glu Gln Ile Leu Ser Ser Asp Asn Leu
1               5                   10                  15

Asn Arg Ala Tyr Leu Gln Val Val Arg Asn Lys Gly Ala Glu Gly Val 20                  25                  30
Asp Gly Met Lys Tyr Thr Glu Leu Lys Glu His Leu Ala Lys Asn Gly
            35                  40                  45

Glu Thr Ile Lys Gly Gln Leu Arg Thr Arg Lys Tyr Lys Pro Gln Pro
 50                  55                  60

Ala Arg Arg Val Glu Ile Pro Lys Pro Asp Gly Val Arg Asn Leu
 65                  70                  75                  80

Gly Val Pro Thr Val Thr Asp Arg Phe Ile Gln Gln Ala Ile Ala Gln
                    85                  90                  95

Val Leu Thr Pro Ile Tyr Glu Glu Gln Phe His Asp His Ser Tyr Gly
                    100                 105                 110

Phe Arg Pro Asn Arg Cys Ala Gln Gln Ala Ile Leu Thr Ala Leu Asn
                    115                 120                 125

Ile Met Asn Asp Gly Asn Asp Trp Ile Val Asp Ile Asp Leu Glu Lys
                    130                 135                 140

Phe Phe Asp Thr Val Asn His Asp Lys Leu Met Thr Leu Ile Gly Arg
145                 150                 155                 160

Thr Ile Lys Asp Gly Asp Val Ile Ser Ile Val Arg Lys Tyr Leu Val
                    165                 170                 175

Ser Gly Ile Met Ile Asp Asp Glu Tyr Glu Asp Ser Ile Val Gly Thr
                    180                 185                 190

Pro Gln Gly Gly Asn Leu Ser Pro Leu Leu Ala Asn Ile Met Leu Asn
                    195                 200                 205

Glu Leu Asp Lys Glu Met Glu Lys Arg Gly Leu Asn Phe Val Arg Tyr
                    210                 215                 220

Ala Asp Asp Cys Ile Ile Met Val Gly Ser Glu Met Ser Ala Asn Arg
225                 230                 235                 240

Val Met Arg Asn Ile Ser Arg Phe Ile Glu Glu Lys Leu Gly Leu Lys
                    245                 250                 255

Val Asn Met Thr Lys Ser Lys Val Asp Arg Pro Ser Gly Leu Lys Tyr
                    260                 265                 270

Leu Gly Phe Gly Phe Tyr Phe Asp Pro Arg Ala His Gln Phe Lys Ala
                    275                 280                 285

Lys Pro His Ala Lys Ser Val Ala Lys Phe Lys Lys Arg Met Lys Glu
                    290                 295                 300

Leu Thr Cys Arg Ser Trp Gly Val Ser Asn Ser Tyr Lys Val Glu Lys
305                 310                 315                 320

Leu Asn Gln Leu Ile Arg Gly Trp Ile Asn Tyr Phe Lys Ile Gly Ser
                    325                 330                 335

Met Ala Thr Leu Cys Ala Glu Leu Asp Ser Arg Ile Arg Tyr Arg Leu
                    340                 345                 350

Ala Met Cys Ile Trp Lys Gln Trp Lys Thr Pro Gln Asn Gln Glu Lys
                    355                 360                 365

Asn Leu Val Lys Leu Gly Ile Asp Arg Asn Thr Ala Arg Arg Val Ala
                    370                 375                 380

Tyr Thr Gly Lys Arg Ile Ala Tyr Val Cys Asn Lys Gly Ala Val Asn
385                 390                 395                 400

Val Ala Ile Ser Asn Lys Arg Leu Ala Ser Phe Gly Leu Ile Ser Met
                    405                 410                 415

Leu Asp Tyr Tyr Ile Glu Lys Cys Val Thr Cys
                    420                 425

<210> SEQ ID NO 19

<211> LENGTH: 418
<212> TYPE: PRT
<213> ORGANISM: Artificial Sequence
<220> FEATURE:
<223> OTHER INFORMATION: Chemically Synthesized, E.r. maturase delta
      loop

<400> SEQUENCE: 19

```
Met Asp Thr Ser Asn Leu Met Glu Gln Ile Leu Ser Ser Asp Asn Leu
1               5                   10                  15

Asn Arg Ala Tyr Leu Gln Val Val Arg Asn Lys Gly Ala Glu Gly Val
            20                  25                  30

Asp Gly Met Lys Tyr Thr Glu Leu Lys Glu His Leu Ala Lys Asn Gly
        35                  40                  45

Glu Thr Ile Lys Gly Gln Leu Arg Thr Arg Lys Tyr Lys Pro Gln Pro
    50                  55                  60

Ala Arg Arg Val Glu Ile Pro Lys Pro Asp Gly Val Arg Asn Leu
65                  70                  75                  80

Gly Val Pro Thr Val Thr Asp Arg Phe Ile Gln Gln Ala Ile Ala Gln
                85                  90                  95

Val Leu Thr Pro Ile Tyr Glu Glu Gln Phe His Asp His Ser Tyr Gly
            100                 105                 110

Phe Arg Pro Asn Arg Cys Ala Gln Gln Ala Ile Leu Thr Ala Leu Asn
        115                 120                 125

Ile Met Asn Asp Gly Asn Asp Trp Ile Val Asp Ile Asp Leu Glu Lys
    130                 135                 140

Phe Phe Asp Thr Val Asn His Asp Lys Leu Met Thr Leu Ile Gly Arg
145                 150                 155                 160

Thr Ile Lys Asp Gly Asp Val Ile Ser Ile Val Arg Lys Tyr Leu Val
                165                 170                 175

Ser Gly Ile Met Ile Gly Gly Pro Gln Gly Gly Asn Leu Ser Pro Leu
            180                 185                 190

Leu Ala Asn Ile Met Leu Asn Glu Leu Asp Lys Glu Met Glu Lys Arg
        195                 200                 205

Gly Leu Asn Phe Val Arg Tyr Ala Asp Asp Cys Ile Ile Met Val Gly
    210                 215                 220

Ser Glu Met Ser Ala Asn Arg Val Met Arg Asn Ile Ser Arg Phe Ile
225                 230                 235                 240

Glu Glu Lys Leu Gly Leu Lys Val Asn Met Thr Lys Ser Lys Val Asp
                245                 250                 255

Arg Pro Ser Gly Leu Lys Tyr Leu Gly Phe Gly Phe Tyr Phe Asp Pro
            260                 265                 270

Arg Ala His Gln Phe Lys Ala Lys Pro His Ala Lys Ser Val Ala Lys
        275                 280                 285

Phe Lys Lys Arg Met Lys Glu Leu Thr Cys Arg Ser Trp Gly Val Ser
    290                 295                 300

Asn Ser Tyr Lys Val Glu Lys Leu Asn Gln Leu Ile Arg Gly Trp Ile
305                 310                 315                 320

Asn Tyr Phe Lys Ile Gly Ser Met Lys Thr Leu Cys Lys Glu Leu Asp
                325                 330                 335

Ser Arg Ile Arg Tyr Arg Leu Arg Met Cys Ile Trp Lys Gln Trp Lys
            340                 345                 350

Thr Pro Gln Asn Gln Glu Lys Asn Leu Val Lys Leu Gly Ile Asp Arg
        355                 360                 365

Asn Thr Ala Arg Arg Val Ala Tyr Thr Gly Lys Arg Ile Ala Tyr Val
```

```
                370               375               380
Cys Asn Lys Gly Ala Val Asn Val Ala Ile Ser Asn Lys Arg Leu Ala
385               390               395               400

Ser Phe Gly Leu Ile Ser Met Leu Asp Tyr Tyr Ile Glu Lys Cys Val
                405               410               415

Thr Cys

<210> SEQ ID NO 20
<211> LENGTH: 17
<212> TYPE: PRT
<213> ORGANISM: Artificial Sequence
<220> FEATURE:
<223> OTHER INFORMATION: Chemically Synthesized

<400> SEQUENCE: 20

Met Ile Asp Asp Glu Tyr Glu Asp Ser Ile Val Gly Thr Pro Gln Gly
1               5                   10                  15

Gly

<210> SEQ ID NO 21
<211> LENGTH: 11
<212> TYPE: PRT
<213> ORGANISM: Artificial Sequence
<220> FEATURE:
<223> OTHER INFORMATION: Chemically Synthesized

<400> SEQUENCE: 21

Met Ile Asp Asp Glu Tyr Glu Asp Ser Ile Val
1               5                   10

<210> SEQ ID NO 22
<211> LENGTH: 41
<212> TYPE: PRT
<213> ORGANISM: Artificial Sequence
<220> FEATURE:
<223> OTHER INFORMATION: Chemically Synthesized

<400> SEQUENCE: 22

Gly Lys Arg Ile Ala Tyr Val Cys Asn Lys Gly Ala Val Asn Val Ala
1               5                   10                  15

Ile Ser Asn Lys Arg Leu Ala Ser Phe Gly Leu Ile Ser Met Leu Asp
                20                  25                  30

Tyr Tyr Ile Glu Lys Cys Val Thr Cys
            35                  40

<210> SEQ ID NO 23
<211> LENGTH: 70
<212> TYPE: RNA
<213> ORGANISM: Artificial Sequence
<220> FEATURE:
<223> OTHER INFORMATION: Chemically Synthesized

<400> SEQUENCE: 23
gucucguauu gcagaaauga caacaucugc cguaaccaau cggguaaaag guggucaaau      60
caagcgagac                                                            70

<210> SEQ ID NO 24
<211> LENGTH: 463
<212> TYPE: PRT
<213> ORGANISM: Chloroflexi bacterium

<400> SEQUENCE: 24
```

```
Met Ser Gly Gln Arg Gln Lys Asn Arg Pro Glu Gln Glu Val Leu Ala
1               5                   10                  15
Phe Pro Val Glu Gly Arg Ser Asp Ala Pro Lys Ala Ala Glu Lys Gly
                20                  25                  30
Thr Glu Thr Leu Val Ala Lys Arg Lys Thr Glu Ser Leu Ala Gly Thr
            35                  40                  45
Glu Arg Leu Met Glu Glu Val Cys Glu Leu Glu Asn Ser Lys Gln Ala
        50                  55                  60
Leu Gln Arg Val Lys Ala Asn Lys Gly Ser Pro Gly Val Asp Gly Met
65                  70                  75                  80
Thr Val Asp Glu Leu Pro Glu Tyr Leu Lys Gln Tyr Gly Pro Glu Ile
                85                  90                  95
Gly Glu Gln Leu Arg Asn Gly Thr Tyr Gln Pro Gln Pro Val Arg Arg
                100                 105                 110
Val Glu Ile Pro Lys Pro Asp Gly Ser Gly Met Arg Lys Leu Gly Ile
            115                 120                 125
Pro Cys Val Leu Asp Arg Phe Val Gln Ala Val Leu Gln Val Leu
        130                 135                 140
Gln Lys Arg Trp Asp Pro Thr Phe Ser Glu His Ser His Gly Phe Arg
145                 150                 155                 160
Pro Gly His Ser Ala Arg Gln Ala Val His Glu Ala Gln Gln Tyr Ile
                165                 170                 175
Ala Glu Gly His Gly Trp Val Val Leu Asp Leu Asp Glu Lys Phe Phe
                180                 185                 190
Asp Arg Val Asn His Asp Arg Leu Leu Ala Ala Val Ala Glu Arg Val
            195                 200                 205
Ala Asp Lys Arg Met Leu Lys Leu Ile Arg Ala Phe Leu Lys Ala Gly
        210                 215                 220
Val Met Glu Asp Gly Leu Val Ser Pro Val Asp Glu Gly Thr Pro Gln
225                 230                 235                 240
Gly Gly Pro Leu Ser Pro Leu Leu Ser Asn Leu Val Leu Asp Glu Leu
                245                 250                 255
Asp Arg Glu Leu Glu Arg Arg Gly His His Phe Val Arg Tyr Ala Asp
            260                 265                 270
Asp Cys Asn Ile Tyr Val Gly Ser Glu Arg Ala Gly Gln Arg Val Met
        275                 280                 285
Glu Ser Val Thr His Phe Ile Thr His Arg Leu Lys Leu Lys Val Asn
        290                 295                 300
Gln Ala Lys Ser Ala Val Ala Arg Pro Arg Gln Arg Lys Phe Leu Gly
305                 310                 315                 320
Phe Ser Phe Thr Ser Glu Arg Glu Pro Arg Arg Arg Ile Ala Pro Lys
                325                 330                 335
Ala Ile Ala Arg Cys Lys Glu Arg Ile Arg Glu Gln Thr Arg Arg Thr
                340                 345                 350
Arg Gly Ile Ser Leu Ala Gln Met Val Lys Glu Ile Ala Thr Tyr Leu
            355                 360                 365
Arg Gly Trp Leu Gly Tyr Phe Gly Asp Cys Gln Thr Pro Ser Val Leu
        370                 375                 380
Gln Arg Leu Glu Ser Trp Leu Arg Arg Arg Leu Arg Ser Val Val Trp
385                 390                 395                 400
Lys Gln Trp Lys Arg Gly Arg Thr Arg Phe Arg Glu Leu Arg Lys Arg
                405                 410                 415
Gly Ile Arg Lys Asp Leu Ala Ala Gln Thr Ala Gly Ser Pro Gln Gly
```

Pro Trp Arg Ile Ala Asn Ser Pro Ala Leu Ser Ile Ala Leu Ser Asn
                     435                 440                 445

Ala Tyr Phe Ala Glu Leu Gly Leu Pro Pro Met Val Val Arg Ser
        450                 455                 460

<210> SEQ ID NO 25
<211> LENGTH: 419
<212> TYPE: PRT
<213> ORGANISM: Bacillus licheniformis

<400> SEQUENCE: 25

Met Leu Met Asn Met Ile Leu Ser Arg Glu Asn Leu Ile Lys Ala Leu
1               5                   10                  15

Lys Arg Val Glu Lys Asn Lys Gly Ser His Gly Ile Asp Gly Met Ser
            20                  25                  30

Val Lys Ser Leu Arg Arg His Leu Tyr Glu Asn Trp Glu Thr Leu Cys
        35                  40                  45

Asn Ser Leu Arg Asn Gly Thr Tyr Gln Pro Asn Pro Val Arg Arg Val
    50                  55                  60

Glu Ile Pro Lys Pro Asn Gly Gly Val Arg Leu Leu Gly Ile Pro Asn
65                  70                  75                  80

Val Thr Asp Arg Phe Ile Gln Gln Ala Ile Ala Gln Val Leu Thr Pro
                85                  90                  95

Leu Phe Asp Pro Thr Phe Ser Glu His Ser Tyr Gly Phe Arg Pro Asn
            100                 105                 110

Lys Arg Gly His Asp Ala Val Arg Lys Ala Arg Gln Tyr Ile Ser Glu
        115                 120                 125

Gly Tyr Arg Trp Val Ile Asp Met Asp Leu Glu Lys Phe Phe Asp Lys
    130                 135                 140

Val Asn His Asp Lys Leu Met Gly Ile Leu Ala Ser Arg Ile Gln Asp
145                 150                 155                 160

Arg Leu Val Leu Lys Leu Ile Arg Lys Tyr Leu Gln Ala Gly Ile Met
                165                 170                 175

Ile Asn Gly Val Val Tyr Asp Ala Glu Glu Thr Pro Gln Gly Gly
            180                 185                 190

Pro Leu Ser Pro Leu Leu Ser Asn Ile Leu Leu Asp Lys Leu Asp Lys
        195                 200                 205

Glu Leu Glu Ser Arg Gly His Lys Phe Val Arg Tyr Ala Asp Asp Cys
    210                 215                 220

Asn Ile Tyr Met Lys Ser Lys Lys Ala Gly Glu Arg Val Met Asn Ser
225                 230                 235                 240

Ile Thr His Phe Ile Glu Glu Lys Leu Lys Leu Lys Val Asn Lys Glu
                245                 250                 255

Lys Ser Ala Val Asp Arg Pro Trp Arg Arg Lys Phe Leu Gly Phe Ser
            260                 265                 270

Phe Thr Val Asn Lys Lys Pro Lys Val Arg Ile Ala Asn Glu Ser Ile
        275                 280                 285

Lys Arg Leu Lys Ala Lys Ile Arg Glu Phe Thr Ser Arg Ser Lys Pro
    290                 295                 300

Ile Pro Met Asp Val Arg Ile Glu Lys Leu Asn Arg Tyr Leu Thr Gly
305                 310                 315                 320

Trp Cys Gly Tyr Phe Ala Leu Ala Asp Thr Pro Ser Lys Phe Lys Glu
                325                 330                 335

```
Phe Asp Glu Trp Ile Arg Arg Arg Leu Arg Met Ile Glu Trp Lys Gln
            340                 345                 350

Trp Lys Lys Pro Met Thr Arg Val Arg Lys Leu Lys Gly Leu Gly Val
        355                 360                 365

Pro Asp Gln Lys Ala Tyr Glu Trp Gly Asn Ser Arg Lys Lys Tyr Trp
    370                 375                 380

Arg Ile Ala Cys Ser Pro Ile Leu Asn Lys Thr Leu Asp Asn Ser Tyr
385                 390                 395                 400

Trp Ser Asn Arg Gly Leu Lys Ser Leu Tyr Gln Arg Tyr Glu Phe Leu
                405                 410                 415

Arg Gln Thr

<210> SEQ ID NO 26
<211> LENGTH: 419
<212> TYPE: PRT
<213> ORGANISM: Geobacillus stearothermophilus

<400> SEQUENCE: 26

Met Trp Met Lys Gln Val Leu Ser Arg Glu Asn Leu Leu Arg Ala Leu
1               5                   10                  15

Lys Gln Val Glu Lys Asn Lys Gly Ser His Gly Thr Asp Gly Met Ser
            20                  25                  30

Val Lys Asp Leu Arg Arg His Leu Val Glu His Trp Asp Ala Ile Arg
        35                  40                  45

His Ala Leu Glu Glu Gly Thr Tyr Glu Pro Cys Pro Val Arg Arg Val
    50                  55                  60

Glu Ile Pro Lys Pro Asn Gly Gly Val Arg Leu Gly Ile Pro Thr
65                  70                  75                  80

Val Thr Asp Arg Phe Ile Gln Gln Ala Ile Ala Gln Val Leu Thr Pro
                85                  90                  95

Ile Phe Asp Pro Ser Phe Leu Glu His Ser Tyr Gly Phe Arg Pro Gly
            100                 105                 110

Arg Arg Gly His Asp Ala Val Lys Lys Ala Lys Gln Tyr Ile Gln Glu
        115                 120                 125

Gly Tyr Thr Trp Val Val Asp Ile Asp Leu Glu Lys Phe Phe Asp Arg
    130                 135                 140

Val Asn His Asp Lys Leu Met Gly Ile Leu Ala Lys Arg Ile Pro Asp
145                 150                 155                 160

Lys Ile Leu Leu Lys Leu Ile Arg Lys Tyr Leu Gln Ala Gly Val Met
                165                 170                 175

Ile Asn Gly Val Val Met Glu Thr Gln Glu Gly Thr Pro Gln Gly Gly
            180                 185                 190

Pro Leu Ser Pro Leu Leu Ser Asn Ile Leu Leu Asp Glu Leu Asp Lys
        195                 200                 205

Glu Leu Glu Lys Arg Gly His Lys Phe Val Arg Tyr Ala Asp Asp Cys
    210                 215                 220

Asn Ile Tyr Val Arg Thr Gln Lys Ala Gly Glu Arg Val Met Lys Ser
225                 230                 235                 240

Ile Thr Ala Phe Ile Glu Lys Lys Leu Arg Leu Lys Val Asn Glu Thr
                245                 250                 255

Lys Ser Ala Val Asp Arg Pro Trp Arg Arg Lys Phe Leu Gly Phe Ser
            260                 265                 270

Phe Thr Pro Ser Lys Glu Pro Lys Ile Arg Ile Ala Arg Glu Ser Ile
        275                 280                 285
```

-continued

```
Arg Arg Met Lys Gln Arg Ile Arg Thr Met Thr Ser Arg Ser Lys Pro
    290                 295                 300

Ile Pro Met Pro Glu Arg Ile Glu Gln Leu Asn Gln Tyr Ile Leu Gly
305                 310                 315                 320

Trp Cys Gly Tyr Phe Ser Leu Ala Glu Thr Pro Ser Val Phe Lys Glu
                325                 330                 335

Leu Asp Gly Trp Ile Arg Arg Leu Arg Met Cys Gln Trp Lys Glu
                340                 345                 350

Trp Lys Leu Pro Arg Thr Arg Val Arg Lys Leu Gln Ser Leu Gly Val
                355                 360                 365

Pro Lys Gln Lys Ala Tyr Glu Trp Gly Asn Thr Arg Lys Lys Tyr Trp
370                 375                 380

Arg Val Ala Ala Ser Pro Ile Leu His Lys Ala Leu Gly Asn Ser Tyr
385                 390                 395                 400

Trp Glu Ser Gln Gly Leu Lys Ser Leu Tyr Gln Arg Tyr Glu Ser Leu
                405                 410                 415

Arg Gln Thr

<210> SEQ ID NO 27
<211> LENGTH: 434
<212> TYPE: PRT
<213> ORGANISM: Chloroflexus aurantiacus

<400> SEQUENCE: 27

Met Leu Val Phe Pro Arg Tyr Ser Gly Pro Ser Leu Ile Glu Gln Val
1               5                   10                  15

Cys Thr Val Glu Asn Leu Thr Asn Ala Trp Arg Arg Val Arg Ser Asn
                20                  25                  30

Ile Lys Val Ser Arg Arg Thr Arg Ser Ala Gly Ile Asp Gln Ile Thr
            35                  40                  45

Leu His Asp Phe Ala Ala Asp Trp Pro Asn Gln Met Val Arg Leu Ala
        50                  55                  60

Glu Glu Leu Arg Asp Gly Ser Tyr Arg Pro Leu Pro Pro Arg Arg Val
65                  70                  75                  80

Ala Ile Ala Lys Ala Ser Gly Gly Glu Arg Ala Ile Ala Ile Leu Thr
                85                  90                  95

Ile Arg Asp Arg Ile Ala Gln Arg Ala Val Gln Gln Val Leu Thr Pro
            100                 105                 110

Leu Phe Glu Pro Leu Phe Leu Asp Cys Ser Tyr Gly Ser Arg Leu Ala
        115                 120                 125

Val Gly Val Pro Glu Ala Ile Glu Arg Val Val Arg Tyr Thr Glu Gln
    130                 135                 140

Gly Leu Ile Trp Val Ile Asp Gly Asp Ile Arg Ala Tyr Phe Asp Ser
145                 150                 155                 160

Ile Asp His Gly Ile Leu Leu Gly Leu Arg Gln Arg Ile Asp Glu
                165                 170                 175

Pro Ala Ile Leu His Leu Ile Ala Gln Trp Leu Ala Val Gly Ser Val
            180                 185                 190

His Thr Glu Thr Pro Asp Glu Thr Leu Pro Asp Ser Pro Leu Val Ala
        195                 200                 205

Leu Leu Arg Arg Ser Gly Glu Leu Ile His Glu Ala Leu Asn Ala Pro
    210                 215                 220

Ser Asp Pro Leu Pro Thr Ala Tyr Asp Tyr Pro Asp Leu Ser Arg Pro
225                 230                 235                 240
```

```
Ala Ser Pro His Ser Gly Ile Pro Thr Gly Leu Phe Ala Ala Leu Ser
            245                 250                 255

Leu Ala Gln Pro Ala Phe Glu Ile Ala Arg Gln Leu Thr Pro Leu Leu
            260                 265                 270

Lys Arg Ile Gly Ala Gln Arg Leu Ala Val Gly Gly Ala Leu Ala Val
            275                 280                 285

Gly Thr Val Leu Leu Ser Glu Leu Val His Arg Ala Gln Ala Ser His
            290                 295                 300

Asp Arg Arg Gly Thr Leu Gln Gly Gly Pro Leu Ser Pro Leu Leu Ala
305                 310                 315                 320

Asn Ile Tyr Leu His Pro Phe Asp Leu Ala Met Thr Ala His Gly Ala
            325                 330                 335

Arg Met Val Arg Phe Val Asp Asp Phe Val Val Met Cys Pro Asp Arg
            340                 345                 350

Thr Thr Ala Glu His Thr Leu Val Leu Val Glu Arg Gln Leu Ala Thr
            355                 360                 365

Leu Arg Leu Thr Leu Asn Pro Gln Lys Thr Arg Ile Val Ala Tyr Ala
            370                 375                 380

Gly Gly Ile Glu Phe Leu Gly Gln Ala Leu Ala Pro Arg Arg Arg Gln
385                 390                 395                 400

Gly Phe Leu His Gly Ile Ser Asp Phe His Ser Ala Glu Gln Arg Leu
            405                 410                 415

Arg Glu His Val Glu Arg Leu Arg Arg Pro Asp Lys Pro Pro Thr Ser
            420                 425                 430

Asp Arg

<210> SEQ ID NO 28
<211> LENGTH: 13
<212> TYPE: RNA
<213> ORGANISM: Artificial Sequence
<220> FEATURE:
<223> OTHER INFORMATION: Chemically Synthesized

<400> SEQUENCE: 28
cguaaccaau cgg                                                          13

<210> SEQ ID NO 29
<211> LENGTH: 15
<212> TYPE: RNA
<213> ORGANISM: Artificial Sequence
<220> FEATURE:
<223> OTHER INFORMATION: Chemically Synthesized

<400> SEQUENCE: 29
ccguaaccaa ucggg                                                        15

<210> SEQ ID NO 30
<211> LENGTH: 22
<212> TYPE: RNA
<213> ORGANISM: Artificial Sequence
<220> FEATURE:
<223> OTHER INFORMATION: Chemically Synthesized

<400> SEQUENCE: 30
ugccguaacc aaucggguaa aa                                                22
```